US006974672B2

(12) United States Patent
Powers et al.

(10) Patent No.: US 6,974,672 B2
(45) Date of Patent: Dec. 13, 2005

(54) GENE AMPLIFICATION IN CANCER

(75) Inventors: Scott Powers, Greenlawn, NY (US);
Jianxin Yang, Commack, NY (US)

(73) Assignee: Amgen Inc., Thousand Oaks, CA (US)

( * ) Notice: Subject to any disclaimer, the term of this patent is extended or adjusted under 35 U.S.C. 154(b) by 118 days.

(21) Appl. No.: 10/390,191

(22) Filed: Mar. 18, 2003

(65) Prior Publication Data

US 2004/0005596 A1 Jan. 8, 2004

Related U.S. Application Data

(60) Provisional application No. 60/365,206, filed on Mar. 19, 2002, and provisional application No. 60/365,192, filed on Mar. 19, 2002.

(51) Int. Cl.$^7$ ............................. C12Q 1/68; C12P 19/34; C12M 1/34; C07H 21/02
(52) U.S. Cl. ........................... 435/6; 435/91.1; 435/91.2; 435/187; 435/287.2; 536/23.1; 536/24.31; 536/24.33; 436/94
(58) Field of Search ........................... 435/6, 91.1, 91.2, 435/183, 287.2; 436/94; 536/23.1, 24.3, 24.31, 24.33

(56) References Cited

U.S. PATENT DOCUMENTS

| 4,109,496 | A | 8/1978 | Allemann et al. |
| 4,376,110 | A | 3/1983 | David et al. |
| 4,816,567 | A | 3/1989 | Cabilly et al. |
| 4,946,778 | A | 8/1990 | Ladner et al. |
| 5,093,246 | A | 3/1992 | Cech et al. |
| 5,225,539 | A | 7/1993 | Winter |
| 5,783,434 | A | 7/1998 | Tung et al. |
| 5,804,177 | A | 9/1998 | Humphries |
| 5,849,711 | A | 12/1998 | Tung et al. |
| 5,858,982 | A | 1/1999 | Tung et al. |
| 6,146,628 | A | 11/2000 | Uckun et al. |
| 6,232,068 | B1 | 5/2001 | Linsley et al. |
| 2003/0159168 | A1 | 8/2003 | Wisotzkey et al. |
| 2003/0224511 | A1 | 12/2003 | Dobie |

FOREIGN PATENT DOCUMENTS

| EP | 1 033 401 | 2/2000 |
| JP | 2000-50885 | 6/1999 |
| WO | WO 96/39194 | 4/1996 |
| WO | WO 99/31256 | 6/1999 |
| WO | WO 99/53040 | 10/1999 |
| WO | WO 99/54447 | 10/1999 |
| WO | WO 01/22920 | 4/2001 |
| WO | WO 0164835 | 9/2001 |

OTHER PUBLICATIONS

Mahlamaki et al., Genes, Chromosomes & Cancer 35: 353–358 (2002).
Aigner, et al., Blood, 89(9):3385–3395 (1997).
Albertson, Embro J. 3(6):1227–1234 (1984).
Altschul et al., Nucleic Acids Res. 25(17):3389–3402 (1997).
Ambros et al., RNA, 9:277–279 (2003).
Andratschke et al., Anticancer Res. 21:3541–3550(2001).
Angerer et al., Methods in Enzymology, 152:649–661.
Ausubel et al., Eds., Greene Publishing and Wiley–Interscience, New York, 1995.
Ausubel et al., Current Protocols in Molecular Biology, eds. 1995 supplement.
Barringer et al., Gene, 89:117–122.
Bass, Nature 411:428–429 (2001).
Batzer et al., Nucleic Acids Res. 19(18):5081 (1991).
Benkerrou et al., Blood, 92(9):3137–3147 (1998).
Bird et al., Science, 242:423–426 (1988).
Boring et al., CA Cancer J. Clini, 43(1):7–26 (1993).
Butler, Methods in Enzymology, 13:482–523 (1981).
Chien et al., Proc. Natl. Acad. Sci. 88:9578–9582 (1991).
Claveriet et al., Computers Chem, 17(2):191–201 (1993).
Colas et al., Nature, 380:548–550 (1996).
Cole et al., Monoclonal Antibodies and Cancer Therapy, 77–96 (1985).
Corpet, F., Nucleic Acids Res, 16(22):10881–10890 (1988).
Cote et al., Proc. Natl. Acad. Sci., 80:2026–2030 (1983).
Couzin, Science, 298:2296–2297 (2002).
Creighton, W.H. Freeman & Co., 34–49 (1983).
Dennis, Nature, 420(6917):732 (2002).
Drebin et al., Cell, 41 Θ695–706 (1985).
Drebin et al., Proc. Natl. Acad. Sci., 83:9129–9133 (1986).
Elbashir et al., Nature, 411:494–498 (2001).
Ellington et al., Nature, 346:818–821 (1990).
Finegan et al., Current Biol. 13(3):236–240 (2003).
Fire et al., Nature, 391:806–811 (1998).
Fogel et al., Cancer Letters 143:87–94 (1999).
Friederichs et al., Cancer Res. 60:6714–6722 (2000).
Fynan et al., Proc. Natl. Acad. Sci., 90:11478–11482 (1993).
Gibson et al., Genome Research, 6:995–1001 (1996).
Goding, Plademic Press, 56–97 (1983).
Graham, EMBRO J. 3:2917 (1984).
Guatelli et al., Proc. Natl. Acad. Sci., 87:1874–1878 (1990).
Harlow et al., Cold Spring Harbor Lab. (1988).
Heid et al., Genome Research, 6:986–994 (1996).
Higgins et al., Gen 73:237–244 (1988).
Houghten et al., Nature, 354:84–86 (1991).
Huang et al., Cancer Res. 55:4717–4721 (1995).
Huang et al., CABIOS, 8(2):155–165 (1992).
Hunter, Cell, 64:249–270 (1991).
Huse et al., Science, 246:1275–1281 (1989).
Huston et al., Proc. Natl. Acad. Sci., 85:5879–5883 (1988).

(Continued)

Primary Examiner—Bradley L. Sisson
(74) Attorney, Agent, or Firm—Banner & Witcoff, Ltd.

(57) ABSTRACT

There are disclosed methods and compositions for the diagnosis, prevention, and treatment of tumors and cancers in mammals, for example, humans, utilizing the CTSZ and CD24 genes, which are amplified colon cancer and/or ovarian cancer and/or breast cancer genes. The CTSZ and CD24 genes, their expressed protein products and antibodies are used diagnostically or as targets for cancer therapy or vaccine; they also are used to identify compounds and reagents useful in cancer diagnosis, prevention, and therapy.

10 Claims, 2 Drawing Sheets

OTHER PUBLICATIONS

Isikawa et al., Igaku–Shoin, Tokyo—New York (1981).
Jackson et al., Cancer Research, 52(19)5264–70 (1992).
James, Current Opinion in Pharmacology 1:540–546 (2001).
Jopling et al., Journal of Biological Chem., 277(9):6864–673 (2002).
Kanakaraj et al., J. Exp. Med. 187(12):2073–2079 (1998).
Kidner et al., Trends in Genetics, 19(1):13–16 (2003).
Knappik et al., J. Mol. Biol. 296:57–86 (2000).
Knuutila et al., Cancer Genet Cytogenet 100:25–30 (1998).
Knuutila et al., American Journ of Pathology, 152(5):1107–1123 (1998).
Kohler et al., Nature, 338:327–328 (1997).
Kozbor et al., Immunology Today, 4(3):72–79 (1983).
Kwoh et al., Proc. Natl. Acad. Sci., 86:1173–1177 (1989).
Lam et al., Nature, 354:82–84 (1991).
Land et al., Science, 222:771–777 (1983).
Landegren et al., Science, 241:1077–1080 (1988).
Langauer et al., Nature, 396:643–649 (1998).
Levrero et al., Gene, 101:195–202 (1991).
Maggio, Enzyme–Immunoassay, CRC Press, Inc., (1980).
Marasco et al., Proc. Natl. Acad. Sci., 90:7889–7893 (1993).
Marks et al., Biotechnology, 10(7):779–783 (1992).
Masui et al., Cancer Res., 44:1002–1007 (1984).
McCafferty et al., Nature, 348:552–554 (1990).
Mendelsohn et al., Trans Assoc Am Physicians, 100:173–8 (1987).
Mischiati et al., Intl Journal of Molecular Medicine 9:633–639 (2002).
Molling, J Mol Med, 75:242–246 (1997).
Morishita et al., Annals NY Acad. Sci., 947:296–303 (2001).
Morrison et al., Proc. Natl. Acad. Sci. 81:6851–6855 (1984).
Morrison, Science, 229:1202–1207 (1985).
Murphy et al., Methods in Molecular Biology, 18: (1993).
Myers et al., CABIOS, 4(1):11–17 (1988).
Nabel et al., Proc. Natl. Acad. Sci., 90:11307–11311 (1993).
Needleman et al., J. Mol. Biol. 48:443–453 (1970).
Neuberger et al., Nature, 312:604–608 (1984).
Nishimura et al., Cancer Res., 47:999–1005 (1987).
Ohtsuka et al., J. Biol. Chem, 260:2605–2608 (1985).
Oi et al., Bio Techniques, 4(3):214 (1986).
Old, Scientific America, 136–143 (1996).
Paddison et al., Genes & Dev. 16:948–958 (2002).
Pearson et al., Proc. Natl. Acad. Sci. 85:2444–2448 (1988).
Pearson, Methods in Molecular Biology, 24:307–331 (1997).
Pinkel et al., Proc. Natl. Acad. Sci., 85:9138–9142 (1988).
Pinkert, Academic Press (1994).
Pollack et al., Nature Genetics 23:41–46 (1999).
Puhler, Ed..Genetic Engineering of Animals, VCH Pub (1993).
Reddy et al., Science, 214:445–450 (1981).
Rossi, Current Biology, 4:469–471 (1994).
Rossolini et al., Molecular and Cellular, 8:91–98 (1994).
Ruley, Nature, 4:602 (1983).
Rylova et al., Cancer Res. 62(3).
Sambrook et al., Molecular Cloning, A Laboratory Manual 2d Ed. 1–3.
Santamaria et al., Journal of Biol. Chem, 273(27):16816–16823 (1998).
Santamaria et al., Cancer Res. 58:1624–1630 (1998).
Shaw et al., J. Natl. Cancer Inst. 80:155–153 (1988).
Shim et al., Int. J. Cancer 94:6–15 (1001).
Smith et al., Adv. Appied Mathematics, 2:482–489 (1981).
Songyang et al., Cell, 72:767–778 (1993).
Stahel, Lung Cancer 11 Suppl 3:531–538 (1994).
Takeda et al., Nature, 314:452–454 (1995).
Tang et al., Nature, 356:152–154 (1992).
Thomas et al., Immunol, 163:978–984 (1999).
Thomas et al., Cell Processing—Purging and Depletion, 252a:997 (Abstract).
Tijssen, Elsevier, Laboratory Techniques in Biochemistry . . . ; 24(2)19–77 (1993).
Tuerk et al., Science 249:505–510 (1990).
Voller et al., Journal of Clinical Pathology, 31:507–520 (1978).
Ward et al., Nature, 341:544–546 (1989).
Wood et al., Nature, 314:446–449 (1985).
Wooton et al., Computers Chem, 17(2):149–163 (1993).
Wu et al., Genomics, 4:560–569 (1989).
Yeh et al., Immunity, 7:715–725 (1997).
Yoshimoto et al., J. Cancer Res., 77:540–545 (1986).
Zeng et al., RNA,9:112–123 (2003).

CTSZ

GENE AMPLIFICATION IN CANCER

This application claims priority to U.S. provisional application Ser. Nos. 60/365,192, filed Mar. 19, 2002, and 60/365,206, filed Mar. 19, 2002, the entireties of which are hereby incorporated by reference.

BACKGROUND OF THE INVENTION

1. Field of the Invention

The invention relates to oncogenes and to cancer diagnostics and therapeutics. More specifically, the present invention relates to amplified and/or overexpressed Cathepsin Z (CTSZ) and CD24 genes that are involved in certain types of cancers. The invention pertains to the amplified genes, their encoded proteins, and antibodies, inhibitors, activators and the like and their use in cancer diagnostics, vaccines, and anti-cancer therapy, including colon cancer, ovarian cancer and breast cancer.

2. Background of the Invention

Cancer and Gene Amplification:

Cancer is the second leading cause of death in the United States, after heart disease (Boring, et al., *CA Cancer J. Clin.,* 43:7, 1993), and it develops in one in three Americans. One of every four Americans dies of cancer. Cancer features uncontrolled cellular growth, which results either in local invasion of normal tissue or systemic spread of the abnormal growth. A particular type of cancer or a particular stage of cancer development may involve both elements.

The division or growth of cells in various tissues functioning in a living body normally takes place in an orderly and controlled manner. This is enabled by a delicate growth control mechanism, which involves, among other things, contact, signaling, and other communication between neighboring cells. Growth signals, stimulatory or inhibitory, are routinely exchanged between cells in a functioning tissue. Cells normally do not divide in the absence of stimulatory signals, and will cease dividing when dominated by inhibitory signals. However, such signaling or communication becomes defective or completely breaks down in cancer cells. As a result, the cells continue to divide; they invade adjacent structures, break away from the original tumor mass, and establish new growth in other parts of the body. The latter progression to malignancy is referred to as "metastasis."

Cancer generally refers to malignant tumors, rather than benign tumors. Benign tumor cells are similar to normal, surrounding cells. These types of tumors are almost always encapsulated in a fibrous capsule and do not have the potential to metastasize to other parts of the body. These tumors affect local organs but do not destroy them; they usually remain small without producing symptoms for many years. Treatment becomes necessary only when the tumors grow large enough to interfere with other organs. Malignant tumors, by contrast, grow faster than benign tumors, and they penetrate and destroy local tissues. Some malignant tumors may spread throughout the body via blood or the lymphatic system. The unpredictable and uncontrolled growth makes malignant cancers dangerous, and fatal in many cases. These tumors are not morphologically typical of the original tissue and are not encapsulated. Malignant tumors commonly recur after surgical removal.

Accordingly, treatment ordinarily is directed towards malignant cancers or malignant tumors. The intervention of malignant growth is most effective at the early stage of the cancer development. It is thus exceedingly important to discover sensitive markers for early signs of cancer formation and to identify potent growth suppression agents associated therewith. The development of such diagnostic and therapeutic agents involves an understanding of the genetic control mechanisms for cell division and differentiation, particularly in connection with tumorigenesis.

Cancer is caused by inherited or acquired mutations in cancer genes, which have normal cellular functions and which induce or otherwise contribute to cancer once mutated or expressed at an abnormal level. Certain well-studied tumors carry several different independently mutated genes, including activated oncogenes and inactivated tumor suppressor genes. Each of these mutations appears to be responsible for imparting some of the traits that, in aggregate, represent the full neoplastic phenotype (Land et al., *Science,* 222:771, 1983; Ruley, *Nature,* 4:602, 1983; Hunter, *Cell,* 64:249, 1991).

One such mutation is gene amplification. Gene amplification involves a chromosomal region bearing specific genes undergoing a relative increase in DNA copy number, thereby increasing the copies of any genes that are present. In general, gene amplification often results in increased levels of transcription and translation, producing higher amounts of the corresponding gene mRNA and protein. Amplification of genes causes deleterious effects, which contribute to cancer formation and proliferation (Lengauer et al. *Nature,* 396:643–649,1999).

It is commonly appreciated by cancer researchers that whole collections of genes are demonstrably overexpressed or differentially expressed in a variety of different types of tumor cells. Yet, only a very small number of these overexpressed genes are likely to be causally involved in the cancer phenotype. The remaining overexpressed genes likely are secondary consequences of more basic primary events, for example, overexpression of a cluster of genes, involved in DNA replication. On the other hand, gene amplification is established as an important genetic alteration in solid tumors (Knuutila et al., *Am. J. Pathol.,* 152(5):1107–23, 1998; Knuutila et al., *Cancer Genet. Cytogenet.,* 100(1):25–30, 1998).

The overexpression of certain well known genes, for example, c-myc, has been observed at fairly high levels in the absence of gene amplification (Yoshimoto et al., *JPN J. Cancer Res.,* 77(6):540–5, 1986), although these genes are frequently amplified (Knuutila et al., *Am. J. Pathol.,* 152(5): 1107–23, 1998) and thereby activated. Such a characteristic is considered a hallmark of oncogenes. Overexpression in the absence of amplification may be caused by higher transcription efficiency in those situations. In the case of c-myc, for example, Yoshimoto et al. showed that its transcriptional rate was greatly increased in the tested tumor cell lines. The characteristics and interplay of overexpression and amplification of a gene in cancer tissues, therefore, provide significant indications of the gene's role in cancer development. That is, increased DNA copies of certain genes in tumors, along with and beyond its overexpression, may point to their functions in tumor formation and progression.

It must be remembered that overexpression and amplification are not the same phenomenon. Overexpression can be obtained from a single, unamplified gene, and an amplified gene does not always lead to greater expression levels of mRNA and protein. Thus, it is not possible to predict whether one phenomenon will result in, or is related to, the other. However, in situations where both amplification of a gene and overexpression of the gene product occur in cells or tissues that are in a precancerous or cancerous state, then that gene and its product present both a diagnostic target and a therapeutic opportunity for intervention. Because some genes are sometimes amplified as a consequence of their location next to a true oncogene, it is also beneficial to determine the DNA copy number of nearby genes in a panel of tumors so that amplified genes that are in the epicenter of the amplification unit can be distinguished from amplified genes that are occasionally amplified due to their proximity to another, more relevant amplified gene.

Thus, discovery and characterization of amplified cancer genes, along with and in addition to their features of overexpression or differential expression, will be a promising avenue that leads to novel targets for diagnostic, vaccines, and therapeutic applications.

Additionally, the completion of the working drafts of the human genome and the paralleled advances in genomics technologies offer new promises in the identification of effective cancer markers and the anti-cancer agents. The high-throughput microarray detection and screening technology, computer-empowered genetics and genomics analysis tools, and multi-platform functional genomics and proteomics validation systems, all assist in applications in cancer research and findings. With the advent of modern sequencing technologies and genomic analyses, many unknown genes and genes with unknown or partially known functions can be revealed.

*Homo sapiens* CTSZ: Cysteine proteases belonging to the papain family represent a major component of the lysosomal proteolytic system and play an essential role in protein degradation and turnover. To date, ten human cysteine proteases of the papain family have been isolated and characterized at the amino acid sequence level: cathepsin B, cathepsin L, cathepsin H, cathepsin S, cathepsin C, cathepsin O, cathepsin K, cathepsin W, cathepsin L2 and cathepsin Z (CTSZ). Existence of additional cysteine proteases including cathepsins M, N, and T, have been documented. These proteases have been originally identified because of their degrading activity on specific substrates such as aldolase, collagen, proinsulin, or tyrosine aminotransferase (Santamaria, et al., *Cancer Res,* 58:624–1630, 1998).

CTSZ is also named as cathepsin X or cathepsin P. A full-length cDNA for CTSZ was first cloned in 1998 by Santamaria et al. from a human brain cDNA library (*J Biol Chem,* 273(27):16816–16823, 1998). The CTSZ DNA of 1501 nucleotides encodes a protein of 303 amino acids. The amino acid sequence encoded by the DNA for CTSZ shows a high degree of identity to cysteine proteases. The human CTSZ gene maps to chromosome 20q13, a location that differs from all cysteine protease genes. On the basis of a series of distinctive structural features, including diverse peptide insertions and an unusual short propeptide, together with its unique chromosomal location among cysteine proteases, CTSZ is regarded as the first representative of a novel subfamily of this class of proteolytic enzymes. Cathepsin Z shares protein sequence identity with other human cysteine proteases of the papain family, including 34% with cathepsin C and 26% with cathepsin B. Cathepsin B at 8p22 is amplified in esophageal adenocarcinoma and overexpressed in esophageal adenocarcinoma, lung, prostate, colon, breast and stomach tumors.

CTSZ is widely expressed in human tissues and therefore the enzyme could be involved in the normal intracellular protein degradation taking place in all cell types. CTSZ is also reported ubiquitously distributed in cancer cell lines and in primary tumors. Recombinant CTSZ exhibited enzymatic activity with substrate specificity and sensitivity toward inhibitors characteristic of cysteine proteases. Therefore, CTSZ has the potential of invasion through its protease activity, and participation in tumor progression like other cathepsins (see WO 99/31256; U.S. Pat. Nos. 5,783,434; 5,849,711; 5,858,982; JP2000-50885).

*Homo sapiens* CD24: *Homo sapiens* CD24 antigen (small cell lung carcinoma cluster 4 antigen) (CD24) is located on the human chromosome 6q21. CD24 is a cell surface antigen, a sialoglycoprotein, that is anchored to the cell surface by a glycosyl phosphatidylinositol linkage. It is expressed in many B-lineage cells and on mature granulocytes. Studies with monoclonal antibodies, however, indicate that most other hematopoietic cells, including T cells, monocytes, red blood cells, and platelets, seem not to express the CD24 antigen. The CD24 DNA is approximately 2.1 kb in length with a coding region of 243 (see SEQ ID NO:4, encoding region 57–299) nucleotides (see SEQ ID NO:6), which encodes a protein of 80 amino acids (see SEQ ID NO:5) (Huang et al., Cancer Res, 55(20):4717–21, 1995; Jackson et al., *Cancer Res,* 52(19):5264–70, 1992).

CD24 has been identified as a ligand for P-selectin in both mouse and human cells. It has been reported that the P-selectin-CD24 binding pathway is important for the binding of the breast carcinoma cell line KS to platelets and the rolling of these cells on endothelial P-selectin (Fogel et al., *Cancer Lett,* 143(1):87–94, 1999; Frienderichs et al., *Cancer Res,* 60:6714–6722, 2000). Since CD24 binds P-selectin that is found on blood vessels, it has been speculated that its expression could help the cells to reach blood vessels (Aigner et al., *Blood,* 89(9):3385–95, 1997). This, however, was highly speculative and the investigators failed to show that-CD24 expression is functionally important in tumor formation.

CD24 has been suggested as a cellular marker (U.S. Pat. Nos. 5,804,177; 6,146,628) and also as a marker in breast and lung carcinomas (Fogel et al., *Cancer Lett,* 143(1): 87–94, 1999; Jackson et al., *Cancer Res,* 52(19):5264–70, 1992). Anti-CD24 antibody also has been suggested to treat B-cell disorder after transplantation (Benkerrou et al., *Blood,* 92(9):3137–3147, 1998). However, its role in tumorogenesis, amplification and overexpression of the CD24 gene in cancers has not been discussed.

Additionally, the possibility to treat tumors with antibodies that block the oncogenic function of CD24, as opposed to antibodies that bind to tumor cells expressing CD24 and thereby mediate tumor-cell killing by mechanisms unrelated to the disclosed oncogenic CD24 function, was not known until the present invention. Therefore, there is a need in the art for an understanding of CTSZ and CD24 gene regulation. Understanding the physiological role of human CTSZ and CD24 genes will facilitate early diagnosis of abnormalities associated therewith and lead to appropriate therapies to treat such abnormalities.

SUMMARY OF THE INVENTION

The present invention relates to isolation, characterization, overexpression and implication of genes, including amplified genes, in cancers, methods and compositions for use in diagnosis, vaccines, prevention, and treatment of tumors and cancers, for example, colon cancer, ovarian cancer, or breast cancer, in mammals, for example, humans. The invention is based on the finding of novel traits of CTSZ and CD24. Specifically, amplification and/or overexpression of CTSZ and/or CD24 genes in tumors, including colon tumors, ovarian tumors, and breast tumors, and their role in oncogenesis were not known until the instant invention.

These novel traits include the overexpression of the CTSZ and/or CD24 genes in certain cancers, for example, colon cancer and/or ovarian cancer and/or breast cancer, and the frequent amplification of CTSZ and/or CD24 genes in cancer cells. The CTSZ and/or CD24 genes and their expressed protein products can thus be used diagnostically or as targets for cancer therapy; and they also can be used to identify and design compounds useful in the diagnosis, prevention, and therapy of tumors and cancers.

Human cDNA sequences for CTSZ gene and CD24 gene, have been previously submitted to GenBank (Accession Nos. NM_001336, and NM_013230, respectively).

Until the present invention, certain utilities of the CTSZ and CD24 genes, associated with diagnostics and therapeutics in various cancers, were not known. Moreover, until the present invention, CTSZ and CD24 genes have not been fully characterized to allow their role in tumor development to be completely understood.

According to one aspect of the present invention, the use of CTSZ and/or CD24 genes in gene therapy, development of small molecule inhibitors, small interfering RNAs (siRNAs), microRNAs (miRNAs), and antisense nucleic acids, and development of immunodiagnostics or immunotherapies are provided. The present invention includes production and the use of antibodies, for example, monoclonal, polyclonal, single-chain and engineered antibodies (including humanized antibodies) and fragments, which specifically bind CTSZ and/or CD24 proteins and/or polypeptides. The invention also features antagonists and inhibitors of CTSZ and CD24 that can inhibit one or more of the functions or activities of CTSZ and/or CD24. Suitable antagonists can include small molecules (molecular weight below about 500 Daltons), large molecules (molecular weight above about 500 Daltons), antibodies, including fragments and single chain antibodies, that bind and interfere or neutralize CTSZ and/or CD24 proteins, polypeptides which compete with a native form of CTSZ and/or CD24 proteins for binding to a protein that naturally interacts with CTSZ and/or CD24 proteins, and nucleic acid molecules that interfere with transcription and/or translation of the CTSZ and/or CD24 gene(s) (for example, antisense nucleic acid molecules, triple helix forming molecules, ribozymes, microRNAs (miRNAs), and small interfering RNAs (siRNAs)). The present invention also includes useful compounds that influence or attenuate activities of CTSZ and/or CD24.

In addition, the present invention provides an inhibitor of CTSZ and/or CD24 activity, wherein the inhibitor is an antibody that blocks the oncogenic function or anti-apoptotic activity of CTSZ and/or CD24, respectively.

The present invention also provides an inhibitor of CTSZ and/or CD24 activity, wherein the inhibitor is an antibody that binds to a cell over-expressing CTSZ and/or CD24 protein, respectively, thereby resulting in suppression or death of the cell.

The present invention further features molecules that can decrease the expression of CTSZ and/or CD24 by affecting transcription or translation. Small molecules (molecular weight below about 500 Daltons), large molecules (molecular weight above about 500 Daltons), and nucleic acid molecules, for example, ribozymes, miRNAs, siRNAs and antisense molecules, including antisense RNA, antisense DNA or DNA decoy or decoy molecules (for example, Morishita et al, *Ann. N Y Acad. Sci.,* 947:294–301, 2001; Andratschke et al, *Anticancer Res.,* 21:(5)3541–3550, 2001), may all be utilized to inhibit the expression or amplification.

As mentioned above, the CTSZ and CD24 gene sequences also can be employed in an RNA interference context. The phenomenon of RNA interference is described and discussed in Bass, *Nature,* 411: 428–29 (2001); Elbashir et al., *Nature,* 411: 494–98 (2001); and Fire et al., *Nature,* 391: 806–11 (1998), where methods of making interfering RNA also are discussed.

In one aspect, the present invention provides methods for diagnosing a cancer, for example, a colon cancer, an ovarian cancer, or a breast cancer, in a mammal, which comprises, in any practical order, obtaining a biological test sample from a region in the tissue that is suspected to be precancerous or cancerous; and comparing the number of CTSZ and CD24 gene copies measured (for example, quantitatively) in the sample to a control or a known value, thereby determining whether the CTSZ or CD24 gene is amplified in the biological test subject, wherein amplification of the CTSZ or CD24 gene indicates a cancer in the tissue.

In another aspect, the present invention provides methods for diagnosing a cancer, for example, a colon cancer, an ovarian cancer, or a breast cancer, in a mammal, which comprises, in any practical order, obtaining a biological test sample from a region in the tissue that is suspected to be precancerous or cancerous; obtaining a biological control sample from a region in the tissue or other tissues in the mammal that is normal; and detecting or measuring in both the biological test sample and the biological control sample the level of CTSZ or CD24 mRNA transcripts, wherein a level of the transcripts higher in the biological subject than that in the biological control sample indicates a cancer in the tissue. In another aspect the biological control sample may be obtained from a different individual or be a normalized value based on baseline data obtained from a population.

In another aspect, the present invention provides methods for diagnosing a cancer, for example, a colon cancer, an ovarian cancer, or a breast cancer, in a mammal, which comprises, in any practical order, obtaining a biological test sample from a region in the tissue that is suspected to be precancerous or cancerous; and comparing the number of CTSZ or CD24 DNA copies detected (for example, qualitatively) in the sample to a control or a known value, thereby determining whether the CTSZ or CD24 gene is amplified in the biological test subject, wherein amplification of the CTSZ or CD24 gene indicates a cancer in the tissue.

Another aspect of the present invention provides methods for diagnosing a cancer, for example, a colon cancer, an ovarian cancer, or a breast cancer, in a mammal, which comprises, in any practical order, obtaining a biological test sample from a region in the tissue that is suspected to be precancerous or cancerous; contacting the sample with anti-CTSZ or anti-CD24, and detecting in the biological subject the level of CTSZ or CD24 expression, wherein an increased level of the CTSZ or CD24 expression in the biological subject as compared to a biological control sample or a known value indicates a precancerous or cancerous condition in the tissue. In an alternative aspect, the biological control sample may be obtained from a different individual or be a normalized value based on baseline data obtained from a population.

In another aspect, the present invention relates to methods for comparing and compiling data wherein the data is stored in electronic or paper format. Electronic format can be selected from the group consisting of electronic mail, disk, compact disk (CD), digital versatile disk (DVD), memory card, memory chip, ROM or RAM, magnetic optical disk, tape, video, video clip, microfilm, internet, shared network, shared server and the like; wherein data is displayed, transmitted or analyzed via electronic transmission, video display, telecommunication, or by using any of the above stored formats; wherein data is compared and compiled at the site of sampling specimens or at a location where the data is transported following a process as described above.

In another aspect, the present invention provides methods for preventing, controlling, or suppressing cancer growth in a mammalian organ and tissue, for example, in the colon, ovary, or breast, which comprises administering an inhibitor of CTSZ or CD24 protein to the organ or tissue, thereby inhibiting CTSZ or CD24 protein activities, respectively. Such inhibitors may be, among other things, an antibody to CTSZ or CD24 protein or polypeptide portions thereof, an antagonist to CTSZ or CD24 protein, respectively, or other small molecules.

In a further aspect, the present invention provides methods for preventing, controlling, or suppressing cancer growth in a mammalian organ and tissue, for example, in the colon, ovary, or breast, which comprises administering to the organ or tissue a nucleotide molecule that is capable of interacting with CTSZ or CD24 DNA or RNA and thereby blocking or interfering the CTSZ or CD24 gene functions, respectively. Such nucleotide molecule can be an antisense nucleotide of the CTSZ or CD24 gene, a ribozyme of CTSZ or CD24 RNA; a small interfering RNA (siRNA); a microRNA (miRNA); or it may be a molecule capable of forming a triple helix with the CTSZ or CD24 gene, respectively.

In still a further aspect, the present invention provides methods for determining the efficacy of a therapeutic treatment regimen for treating a cancer, for example, a colon cancer, an ovarian cancer, or a breast cancer, in a patient, for example, in a clinical trial or other research studies, which comprises, in any practical order, obtaining a first biological sample from the patient; administering the treatment regimen to the patient; obtaining a second biological sample from the patient after a time period; and detecting in both the first and the second biological samples the level of CTSZ or CD24 mRNA transcripts, wherein a level of the transcripts lower in the second biological sample than that in the first biological sample indicates that the treatment regimen is effective in the patient.

In another aspect, the present invention provides methods for determining the efficacy of a compound to suppress a cancer, for example, a colon cancer, an ovarian cancer, or a breast cancer, in a patient, for example, in a clinical trial or other research studies, which comprises, in any practical order, obtaining a first biological sample from the patient; administering the treatment regimen to the patient; obtaining the second biological sample from the patient after a time period; and detecting in both the first and the second biological samples the level of CTSZ or CD24 mRNA transcripts, wherein a level of the transcripts lower in the second biological sample than that in the first biological sample indicates that the compound is effective to suppress such a cancer.

In another aspect, the present invention provides methods for determining the efficacy of a therapeutic treatment regimen for treating a cancer, for example, a colon cancer, an ovarian cancer, or a breast cancer, in a patient, for example, in a clinical trial or other research studies, which comprises, in any practical order, obtaining a first biological sample from the patient; administering the treatment regimen to the patient; obtaining a second biological sample from the patient after a time period; and detecting in both the first and the second biological samples the number of CTSZ or CD24 DNA copies, thereby determining the overall or average CTSZ or CD24 gene amplification state in the first and second biological samples, wherein a lower number of CTSZ or CD24 DNA copies in the second biological sample than that in the first biological sample indicates that the treatment regimen is effective.

In yet another aspect, the present invention provides methods for determining the efficacy of a therapeutic treatment regimen for treating a cancer, for example, a colon cancer, an ovarian cancer, or a breast cancer, in a patient, which comprises, in any practical order, obtaining a first biological sample from the patient; administering the treatment regimen to the patient; obtaining a second biological sample from the patient after a time period; contacting the samples with anti-CTSZ or anti-CD24 antibodies, and detecting the level of CTSZ or CD24 expression, in both the first and the second biological samples. A lower level of the CTSZ or CD24 expression in the second biological sample than that in the first biological sample indicates that the treatment regimen is effective to the patient.

Yet, in another aspect, the invention provides methods for determining the efficacy of a therapeutic treatment regimen for treating a cancer, for example, a colon cancer, an ovarian cancer, or a breast cancer, in a patient, comprising, in any practical order, the steps of: obtaining a first biological sample from the patient; administering the treatment regimen to the patient; obtaining a second biological sample from the patient after a time period; contacting the biological samples with anti-CTSZ or anti-CD24 antibodies, determining the expression level of CTSZ or CD24, in both the first and the second biological samples by determining the overall expression divided by the number of cells present in each sample; and comparing the expression level of CTSZ or CD24 in the first and the second biological samples, respectively. A lower level of the CTSZ or CD24 expression in second biological sample than that in the first biological sample indicates that the treatment regimen is effective to the patient, wherein the expression level is determined via a binding assay.

In still another aspect, the present invention provides methods for determining the efficacy of a compound to suppress a cancer, for example, a colon cancer, an ovarian cancer, or a breast cancer, in a patient, for example, in a clinical trial or other research studies, which comprises, in any practical order, obtaining a first biological sample from the patient; administering the treatment regimen to the patient; obtaining a second biological sample from the patient after a time period; and detecting in both the first and the second biological samples the number of CTSZ or CD24 DNA copies, thereby determining the CTSZ or CD24 gene amplification state in the first and second biological samples, wherein a lower number of CTSZ or CD24 DNA copies in the second biological sample than that in the first biological sample indicates that the compound is effective.

In another aspect, the present invention provides methods for monitoring the efficacy of a therapeutic treatment regimen for treating a cancer, for example, a colon cancer, an ovarian cancer, or a breast cancer, in a patient, for example, in a clinical trial or other research studies, which comprises, in any practical order, obtaining a first biological sample from the patient; administering the treatment regimen to the patient; obtaining a second biological sample from the patient after a time period; and detecting in both the first and the second biological samples the level of CTSZ or CD24 mRNA transcripts, wherein a level of the transcripts lower in the second biological sample than that in the first biological sample indicates that the treatment regimen is effective to the patient.

Yet, in another aspect, the invention provides methods for monitoring the efficacy of a therapeutic treatment regimen for treating a cancer, for example, a colon cancer, an ovarian cancer, or a breast cancer, in a patient, for example, in a clinical trial or other research studies, comprising, in any practical order, the steps of: obtaining a first biological sample from the patient; administering the treatment regimen to the patient; obtaining a second biological sample from the patient after a time period; determining in both the first and the second biological samples the level of CTSZ or CD24 mRNA transcripts, by determining the overall level divided by the number of cells present in each sample; and comparing the level of CTSZ or CD24 in the first and the second biological samples, respectively. A lower level of the CTSZ or CD24 mRNA transcripts in second biological sample than that in the first biological sample indicates that the treatment regimen is effective to the patient, wherein the level is determined via a binding assay.

In another aspect, the present invention provides methods for monitoring the efficacy of a compound to suppress a cancer, for example, a colon cancer, an ovarian cancer, or a breast cancer, in a patient, for example, in a clinical trial or other research studies, which comprises, in any practical order, obtaining a first biological sample from the patient; administering the treatment regimen to the patient; obtaining the second biological sample from the patient after a time period; and detecting in both the first and the second biological samples the level of CTSZ or CD24 mRNA transcripts, wherein a level of the transcripts lower in the second biological sample than that in the first biological sample indicates that the compound is effective to suppress such a cancer.

In another aspect, the present invention provides methods for monitoring the efficacy of a therapeutic treatment regimen for treating a cancer, for example, a colon cancer, an ovarian cancer, or a breast cancer, in a patient, for example, in a clinical trial or other research studies, which comprises, in any practical order, obtaining a first biological sample from the patient; administering the treatment regimen to the patient; obtaining a second biological sample from the patient after a time period; and detecting in both the first and the second biological samples the number of CTSZ or CD24 DNA copies, thereby determining the overall or average CTSZ or CD24 gene amplification state in the first and second biological samples, wherein a lower number of CTSZ or CD24 DNA copies in the second biological sample than that in the first biological sample indicates that the treatment regimen is effective.

In yet another aspect, the present invention provides methods for monitoring the efficacy of a therapeutic treatment regimen for treating a cancer, for example, a colon cancer, an ovarian cancer, or a breast cancer, in a patient, which comprises, in any practical order, obtaining a first biological sample from the patient; administering the treatment regimen to the patient; obtaining a second biological sample from the patient after a time period; contacting the samples with anti-CTSZ or anti-CD24 antibodies, and detecting the level of CTSZ or CD24 expression, in both the first and the second biological samples. A lower level of the CTSZ or CD24 expression in the second biological sample than that in the first biological sample indicates that the treatment regimen is effective to the patient.

Yet, in another aspect, the invention provides methods for monitoring the efficacy of a therapeutic treatment regimen for treating a cancer, for example, a colon cancer, an ovarian cancer, or a breast cancer, in a patient, comprising, in any practical order, the steps of: obtaining a first biological sample from the patient; administering the treatment regimen to the patient; obtaining a second biological sample from the patient after a time period; contacting the biological samples with anti-CTSZ or anti-CD24 antibodies, determining the level of CTSZ or CD24 expression, in both the first and the second biological samples by determining the overall expression divided by the number of cells present in each sample; and comparing the expression level of CTSZ or CD24 in the first and the second biological samples, respectively. A lower level of the CTSZ or CD24 expression in second biological sample than that in the first biological sample indicates that the treatment regimen is effective to the patient, wherein the expression level is determined via a binding assay.

In still another aspect, the present invention provides methods for monitoring the efficacy of a compound to suppress a cancer, for example, a colon cancer, an ovarian cancer, or a breast cancer, in a patient, for example, in a clinical trial or other research studies, which comprises, in any practical order, obtaining a first biological sample from the patient; administering the treatment regimen to the patient; obtaining a second biological sample from the patient after a time period; and detecting in both the first and the second biological samples the number of CTSZ or CD24 DNA copies, thereby determining the CTSZ or CD24 gene amplification state in the first and second biological samples, wherein a lower number of CTSZ or CD24 DNA copies in the second biological sample than that in the first biological sample indicates that the compound is effective.

One aspect of the invention provides methods for diagnosing cancer and/or monitoring the efficacy of a cancer therapy by using isolated CTSZ or CD24 gene amplicon, wherein the methods futher comprise, in any practical order, obtaining a biological test sample from a region in the tissue that is suspected to be precancerous or cancerous; obtaining a biological control sample from a region in the tissue or other tissues in the mammal that is normal; and detecting in both the biological test sample and the biological control sample for the presence and extent of CTSZ or CD24 gene amplicons, wherein a level of amplification higher in the biological subject than that in the biological control sample indicates a precancerous or cancer condition in the tissue. In an aspect, the biological control sample may be obtained from a different individual or be a normalized value based on baseline data obtained from a population.

Another aspect of the invention is to provide an isolated CTSZ gene amplicon, wherein the amplicon comprises a completely or partially amplified product of CTSZ gene, including a polynucleotide having at least about 90% sequence identity to CTSZ gene, for example, SEQ ID NO:1, SEQ ID NO:3, a polynucleotide encoding the polypeptide set forth in SEQ ID NO:2 or a polynucleotide that is overexpressed in tumor cells having at least about 90% sequence identity to the polynucleotide of SEQ ID NO:1, SEQ ID NO:3, or the polynucleotide encoding the polypeptide set forth in SEQ ID NO:2.

Another aspect of the invention is to provide an isolated CD24 gene amplicon, wherein the amplicon comprises a completely or partially amplified product of CD24 gene, including a polynucleotide having at least about 90% sequence identity to CD24 gene, for example, SEQ ID NO:4, SEQ ID NO:6, or a polynucleotide encoding the polypeptide set forth in SEQ ID NO:5, or a polynucleotide that is overexpressed in tumor cells having at least about 90% sequence identity to the polynucleotide of SEQ ID NO:4, SEQ ID NO:6, or the polynucleotide encoding the polypeptide set forth in SEQ ID NO:5.

In yet another aspect, the present invention provides methods for modulating CTSZ or CD24 activities by contacting a biological subject from a region that is suspected to be precancerous or cancerous with a modulator of the CTSZ or CD24 protein, wherein the modulator is, for example, a small molecule.

In still another aspect, the present invention provides methods for modulating CTSZ or CD24 activities by contacting a biological subject from a region that is suspected to be precancerous or cancerous with a modulator of the CTSZ or CD24 protein, wherein said modulator partially or completely inhibits transcription of CTSZ or CD24 gene.

Another aspect of the invention is to provide methods of making a pharmaceutical composition comprising: identifying a compound which is an inhibitor of CTSZ or CD24 activity, including the oncogenic function or anti-apoptotic activity of CTSZ or CD24; producing the compound; and optionally mixing the compound with suitable additives.

Still another aspect of the invention is to provide a pharmaceutical composition obtainable by the methods described herein, wherein the composition comprises an antibody that blocks the oncogenic function or anti-apoptotic activity of CTSZ or CD24.

Another aspect of the invention is to provide a pharmaceutical composition obtainable by the methods described herein, wherein the composition comprises an antibody that binds to a cell over-expressing CTSZ or CD24 protein, thereby resulting in death of the cell.

Yet another aspect of the invention is to provide a pharmaceutical composition obtainable by the methods described herein, wherein the composition comprises a CTSZ- or CD24-derived polypeptide or a fragment or a mutant thereof, wherein the polypeptide has inhibitory activity that blocks the oncogenic function or anti-apoptotic activity of CTSZ or CD24.

In still a further aspect, the invention provides methods for inducing an immune response in a mammal comprising contacting the mammal with CTSZ or CD24 polypeptide or polynucleotide, or a fragment thereof, wherein the immune response produces antibodies and/or T cell immune response to protect the mammal from cancers, including a colon cancer, an ovarian cancer, or a breast cancer.

Another aspect of the invention is to provide methods of administering siRNA to a patient in need thereof, wherein the siRNA molecule is delivered in the form of a naked oligonucleotide, sense molecule, antisense molecule, or a vector, wherein the siRNA interacts with CTSZ or CD24 gene or its transcripts, wherein the vector is a plasmid, cosmid, bacteriophage, or a virus, wherein the virus is for example, a retrovirus, an adenovirus, or other suitable viral vector.

Another aspect of the invention is to provide methods of administering miRNA to a patient in need thereof, wherein the miRNA molecule is delivered in the form of a naked oligonucleotide, sense molecule, antisense molecule, or a vector, wherein the miRNA interacts with CTSZ or CD24 gene or its transcripts, wherein the vector is a plasmid, cosmid, bacteriophage, or a virus, wherein the virus is for example, a retrovirus, an adenovirus, or other suitable viral vector.

Still in another aspect, the invention provides methods of administering a decoy molecule to a patient in need thereof, wherein the molecule is delivered in the form of a naked oligonucleotide, sense molecule, antisense molecule, a decoy DNA molecule, or a vector, wherein the molecule interacts with CTSZ or CD24 gene, wherein the vector is a plasmid, cosmid, bacteriophage, or a virus, wherein the virus is for example, a retrovirus, an adenovirus, or other suitable viral vector.

In still a further aspect of the invention, CTSZ or CD24 decoys, antisense, triple helix forming molecules, and ribozymes can be administered concurrently or consecutively in any proportion; for example, two of the above can be administered concurrently or consecutively in any proportion; or they can be administered singly (that is, decoys, triple helix forming molecules, antisense or ribozymes targeting only one of CTSZ or CD24). Additionally, decoys, triple helix forming molecules, antisense and ribozymes having different sequences but directed against a given target (that is, CTSZ and/or CD24) can be administered concurrently or consecutively in any proportion, including equimolar proportions. Thus, as is apparent to the skilled person in view of the teachings herein, one could choose to administer one CTSZ or CD24 decoy molecule, triple helix forming molecules, antisense and/or ribozymes, and/or two different CTSZ or CD24 decoys, triple helix forming molecules, antisense and/or ribozymes, and/or three different CTSZ or CD24 decoys, triple helix forming molecules, antisense and/or ribozymes in any proportion, including equimolar proportions, for example. Of course, other permutations and proportions can be employed by the person skilled in the art.

Still in another aspect, the invention provides methods of administering CTSZ-siRNA and/or CTSZ-miRNA and/or CD24-siRNA and/or CD24-miRNA to a patient in need thereof, wherein one or more of the above siRNA and/or miRNA molecules are delivered in the form of a naked oligonucleotide, sense molecule, antisense molecule or a vector, wherein the siRNA(s) and/or miRNA(s) interact(s) with CTSZ or CD24 activity, wherein the vector is a plasmid, cosmid, bacteriophage or a virus, wherein the virus is for example, a retrovirus, an adenovirus, or other suitable viral vector. In other words, CTSZ and CD24 siRNAs and/or miRNAs can be administered concurrently or consecutively in any proportion; only two of the above can be administered concurrently or consecutively in any proportion; or they can be administered singly (that is, siRNAs or miRNAs targeting only one of CTSZ or CD24). Additionally, siRNAs or miRNAs having different sequences but directed against a given target (that is, CTSZ or CD24) can be administered concurrently or consecutively in any proportion, including equimolar proportions. Thus, as is apparent to the skilled person in view of the teachings herein, one could choose to administer one CTSZ or CD24 siRNA or miRNA and/or two different CTSZ or CD24 siRNAs or miRNAs and/or three different CTSZ or CD24 siRNAs or miRNAs in any proportion, including equimolar proportions, for example. Of course, other permutations and proportions can be employed by the person skilled in the art. Additionally, siRNAs or miRNAs can be employed together with one or more of decoys, triple helix forming molecules, antisense, ribozymes, and other functional molecules.

In another aspect, the present invention provides methods of blocking in vivo expression of a gene by administering a vector containing CTSZ siRNA or miRNA and/or CD24 siRNA or miRNA, wherein the siRNA and/or miRNA interacts with CTSZ and/or CD24 activity, wherein the siRNA and/or miRNA causes post-transcriptional silencing of CTSZ and/or CD24 genes or inhibit translation of RNA into protein, in a mammalian cell, for example, a human cell.

Yet, in another aspect, the present invention provides methods of treating cells ex vivo by administering a vector as described herein, wherein the vector is a plasmid, cosmid, bacteriophage, or a virus, such as a retrovirus or an adenovirus.

In its in vivo or ex vivo therapeutic applications, it is appropriate to administer siRNA and/or shRNA and/or miRNA using a viral or retroviral vector which enters the cell by transfection or infection. In particular, as a therapeutic product according to the invention, a vector can be a defective viral vector such as an adenovirus or a defective retroviral vector such as a murine retrovirus.

Another aspect of the invention provides methods of screening a test molecule for CTSZ or CD24 antagonist activity comprising, in any practical order, the steps of: contacting a cancer cell with the molecule; determining the level of CTSZ and/or CD24 in the cell, thereby generating data for a test level; and comparing the test level to the level of CTSZ and/or CD24 in the cell prior to contacting the test molecule, wherein a decrease in CTSZ and/or CD24 in the test level indicates CTSZ and/or CD24 antagonist activity of the test molecule, wherein the level of CTSZ or CD24 is determined by, for example, reverse transcription and polymerase chain reaction (RT-PCR), Northern hybridization, or microarray analysis.

In another aspect, the invention provides methods of screening a test molecule for CTSZ or CD24 antagonist activity comprising the steps of: contacting the molecule with CTSZ or CD24; and determining the effect of the test molecule on CTSZ or CD24, wherein the effect is determined via a binding assay.

In another aspect, the invention provides methods of determining whether a test molecule has CTSZ antagonist activity, wherein the method comprises, in any practical order, determining the level of CTSZ and/or CD24 in a biological sample containing cancer cells, thereby generating data for a test level; contacting the molecule with the biological sample; and comparing the test level to the CTSZ and/or CD24 level of the biological sample after contacting the test molecule, wherein no decrease in CTSZ and/or CD24 in the test level indicates the test molecule having no CTSZ and/or CD24 antagonist activity.

In another aspect, the invention provides methods for selecting for test molecules having CTSZ and/or CD24 antagonist activity, wherein the method comprises, in any practical order, determining the level of CTSZ and/or CD24 in a biological sample containing cancer cells, thereby generating data for a test level; contacting the molecule with the biological sample; comparing the test level to the CTSZ and/or CD24 level of the biological sample after contacting the test molecule, wherein no decrease in CTSZ and/or CD24 in the test level indicates the test molecule having no CTSZ and/or CD24 antagonist activity; and eliminating the test molecule from further evaluation or study.

Yet, in another aspect, the invention provides methods of screening a test molecule for CTSZ or CD24 antagonist activity comprising, in any practical order, the steps of: contacting a biological sample containing cancer cells with the test molecule; determining the expression level of CTSZ or CD24 in a cell by determining the overall mRNA expression divided by the number of cells present in the sample, thereby generating data for a test level; and comparing the test level to the expression level of CTSZ or CD24 in the cell prior to contacting the test molecule, wherein a decrease in expression of CTSZ or CD24 in the test level indicates CTSZ or CD24 antagonist activity of the test molecule, wherein the expression level of CTSZ or CD24 can be determined by, for example, reverse transcription and polymerase chain reaction (RT-PCR), Northern hybridization, or microarray analysis.

Still in another aspect, the invention provides methods of screening a test molecule for CTSZ or CD24 antagonist activity comprising, in any practical order, the steps of: determining the mRNA expression level of CTSZ and/or CD24 in a biological sample containing cancer cells, thereby generating data for a pre-test level expression of CTSZ or CD24 mRNA; contacting the biological sample with the test molecule; determining the expression level of CTSZ or CD24 mRNA in a cell by determining the overall mRNA expression divided by the number of cells present in the sample, thereby generating data for a test level; and comparing the test level to the pre-test level expression of CTSZ or CD24 mRNA, wherein a decrease in expression of CTSZ and/or CD24 mRNA in the test level indicates CTSZ or CD24 antagonist activity of the test molecule, wherein the expression level of CTSZ or CD24 can be determined by, for example, reverse transcription and polymerase chain reaction (RT-PCR), Northern hybridization, or microarray analysis.

In another aspect, the invention provides methods for determining the level of CTSZ or CD24 in a biological sample for diagnosis of cancer, for example, colon cancer, ovarian cancer, or breast cancer, in a patient, comprising, in any practical order, obtaining a control biological sample; obtaining a biological sample from the patient; contacting the biological samples with anti-CTSZ or anti-CD24 antibodies, determining the level of CTSZ or CD24 in both the control biological sample and the biological samples obtained from the patient, by determining the overall level of CTSZ or CD24 divided by the number of cells present in each sample, respectively; and comparing the level of CTSZ or CD24 in the control biological sample and the biological samples obtained from the patient, respectively. A higher level of the CTSZ or CD24 in the biological sample obtained from the patient than that in the control biological sample indicates a cancer or a precancerous condition, wherein the CTSZ and CD24 level are determined via binding assays.

In another aspect, the invention provides methods for determining the efficacy of a therapeutic treatment regimen in a patient, comprising, in any practical order, measuring at least one of CTSZ and/or CD24 mRNA or CTSZ and/or CD24 expression levels in a first biological sample obtained from the patient, thereby generating data for a test level; administering the treatment regimen to the patient; measuring at least one of CTSZ and/or CD24 mRNA or CTSZ and/or CD24 expression levels in a second biological sample from the patient at a time following administration of the treatment regimen; and comparing at least one of CTSZ and/or CD24 mRNA or CTSZ and/or CD24 expression levels in the first and the second biological samples, wherein data showing no decrease in the levels in the second biological sample relative to the first biological sample indicates that the treatment regimen is not effective in the patient.

In another aspect, the invention provides methods for selecting test molecules having a therapeutic effect in a patient, comprising, in any practical order, measuring at least one of CTSZ and/or CD24 mRNA or CTSZ and/or CD24 expression levels in a first biological sample obtained from the patient, thereby generating data for a test level; administering the test molecule to the patient; measuring at least one of CTSZ and/or CD24 mRNA or CTSZ and/or CD24 expression levels in a second biological sample from the patient at a time following administration of the test molecule; comparing at least one of CTSZ and/or CD24 mRNA or CTSZ and/or CD24 expression levels in the first and the second biological samples, wherein data showing no decrease in the levels in the second biological sample relative to the first biological sample indicates that the test molecule is not effective in the patient; and eliminating the test molecule from further evaluation or study.

Unless otherwise defined, all technical and scientific terms used herein in their various grammatical forms have the same meaning as commonly understood by one of ordinary skill in the art to which this invention belongs. Although methods and materials similar to those described herein can be used in the practice or testing of the present invention, the preferred methods and materials are described below. In case of conflict, the present specification, including definitions, will control. In addition, the materials, methods, and examples are illustrative only and are not limiting.

Further features, objects, and advantages of the present invention are apparent in the claims and the detailed description that follows. It should be understood, however, that the detailed description and the specific examples, while indicating preferred aspects of the invention, are given by way of illustration only, since various changes and modifications within the spirit and scope of the invention will become apparent to those skilled in the art from this detailed description.

DETAILED DESCRIPTION OF THE INVENTION

Figure 1:
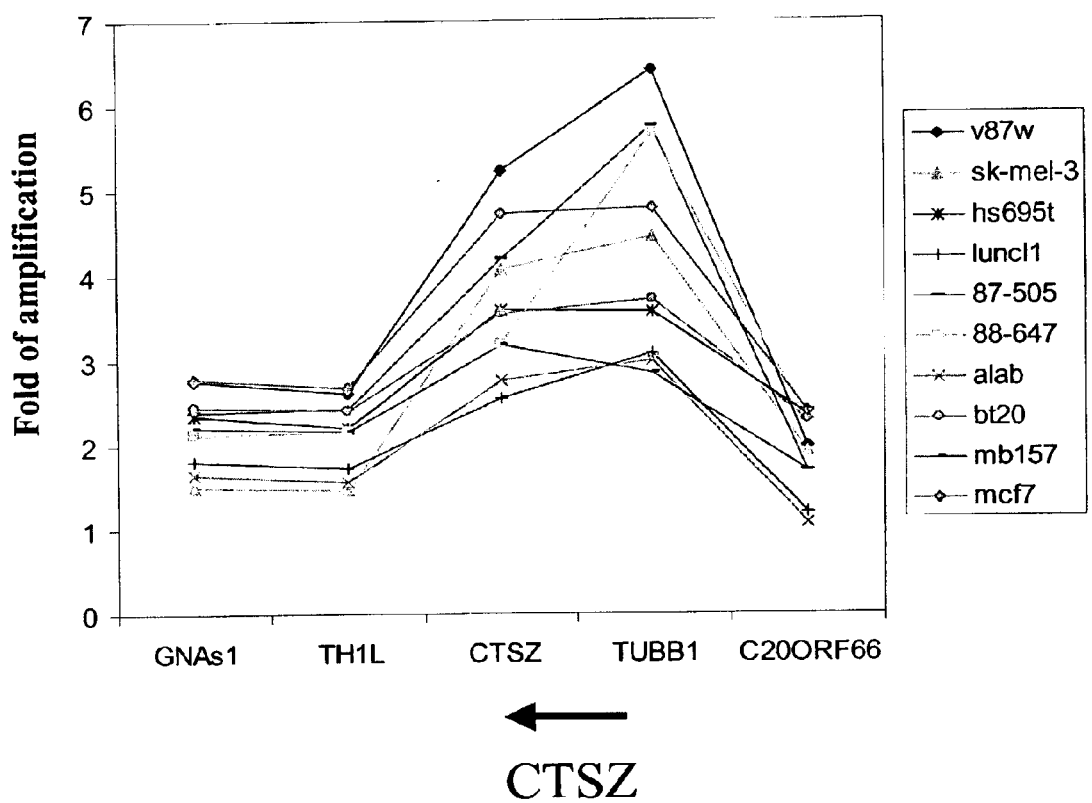
FIG. 1 depicts the epicenter mapping of human chromosome region 20q13 amplicon, which includes CTSZ locus. The number of DNA copies for each sample is plotted on the Y-axis, and the X-axis corresponds to nucleotide position based on Human Genome Project working draft sequence (http://genome.ucsc.edu/goldenPath/aug2001Tracks.html).

The present invention provides methods and compositions for the diagnosis, prevention, and treatment of tumors and cancers, for example, colon cancer, ovarian cancer, or breast cancer, in mammals, for example, humans. The invention is based on the findings of novel traits of the CTSZ and CD24 genes. The CTSZ and/or CD24 genes and their expressed protein products can thus be used diagnostically or as targets for therapy; and, they also can be used to identify compounds useful in the diagnosis, prevention, and therapy of tumors and cancers (for example, a colon cancer, an ovarian cancer, or a breast cancer).

The present invention provides isolated amplified CTSZ and CD24 genes. This invention also provides that the CTSZ and/or CD24 genes are frequently amplified and/or overexpressed in tumor cells, for example, human colon tumor, ovarian tumor, or breast tumor.

Definitions:

A "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells.

The phrase "detecting a cancer" or "diagnosing a cancer" refers to determining the presence or absence of cancer or a precancerous condition in an animal. "Detecting a cancer" also can refer to obtaining indirect evidence regarding the likelihood of the presence of precancerous or cancerous cells in the animal or assessing the predisposition of a patient to the development of a cancer. Detecting a cancer can be accomplished using the methods of this invention alone, in combination with other methods, or in light of other information regarding the state of health of the animal.

A "tumor," as used herein, refers to all neoplastic cell growth and proliferation, whether malignant or benign, and all precancerous and cancerous cells and tissues.

The term "precancerous" refers to cells or tissues having characteristics relating to changes that may lead to malignancy or cancer. Examples include adenomatous growths in colon, ovary, breast, tissues, or conditions, for example, dysplastic nevus syndrome, a precursor to malignant melanoma of the skin. Examples also include, abnormal neoplastic, in addition to dysplastic nevus syndromes, polyposis syndromes, prostatic dysplasia, and other such neoplasms, whether the precancerous lesions are clinically identifiable or not.

A "differentially expressed gene transcript", as used herein, refers to a gene, including an oncogene, transcript that is found in different numbers of copies in different cell or tissue types of an organism having a tumor or cancer, for example, a colon cancer, an ovarian cancer, or a breast cancer, compared to the numbers of copies or state of the gene transcript found in the cells of the same tissue in a healthy organism, or in the cells of the same tissue in the same organism. Multiple copies of gene transcripts may be found in an organism having the tumor or cancer, while fewer copies of the-same gene transcript are found in a healthy organism or healthy cells of the same tissue in the same organism, or vice-versa.

A "differentially expressed gene," can be a target, fingerprint, or pathway gene. For example, a "fingerprint gene", as used herein, refers to a differentially expressed gene whose expression pattern can be used as a prognostic or diagnostic marker for the evaluation of tumors and cancers, or which can be used to identify compounds useful for the treatment of tumors and cancers, for example, colon cancer, ovarian cancer, or breast cancer. For example, the effect of a compound on the fingerprint gene expression pattern normally displayed in connection with tumors and cancers can be used to evaluate the efficacy of the compound as a tumor and cancer treatment, or can be used to monitor patients undergoing clinical evaluation for the treatment of tumors and cancer.

A "fingerprint pattern", as used herein, refers to a pattern generated when the expression pattern of a series (which can range from two up to all the fingerprint genes that exist for a given state) of fingerprint genes is determined. A fingerprint pattern also may be referred to as an "expression profile". A fingerprint pattern or expression profile can be used in the same diagnostic, prognostic, and compound identification methods as the expression of a single fingerprint gene.

A "target gene", as used herein, refers to a differentially expressed gene in which modulation of the level of gene expression or of gene product activity prevents and/or ameliorates tumor and cancer, for example, colon cancer, ovarian cancer, or breast cancer, symptoms. Thus, compounds that modulate the expression of a target gene, the target genes, or the activity of a target gene product can be used in the diagnosis, treatment or prevention of tumors and cancers. A particular target gene of the present invention is the CTSZ or CD24 gene.

In general, a "gene" is a region on the genome that is capable of being transcribed to an RNA that either has a regulatory function, a catalytic function, and/or encodes a protein. An eukaryotic gene typically has introns and exons, which may organize to produce different RNA splice variants that encode alternative versions of a mature protein. The skilled artisan will appreciate that the present invention encompasses all, CTSZ- and CD24-encoding transcripts that may be found, including splice variants, allelic variants and transcripts that occur because of alternative promoter sites or alternative poly-adenylation sites. A "full-length" gene or RNA therefore encompasses any naturally occurring splice variants, allelic variants, other alternative transcripts, splice variants generated by recombinant technologies which bear the same function as the naturally occurring variants, and the resulting RNA molecules. A "fragment" of a gene, including an oncogene, can be any portion from the gene, which may or may not represent a functional domain, for example, a catalytic domain, a DNA binding domain, etc. A fragment may preferably include nucleotide sequences that encode for at least 25 contiguous amino acids, and preferably at least about 30, 40, 50, 60, 65, 70, 75 or more contiguous amino acids or any integer thereabout or therebetween.

"Pathway genes", as used herein, are genes that encode proteins or polypeptides that interact with other gene products involved in tumors and cancers. Pathway genes also can exhibit target gene and/or fingerprint gene characteristics.

A "detectable" RNA expression level, as used herein, means a level that is detectable by standard techniques currently known in the art or those that become standard at some future time, and include for example, differential display, RT (reverse transcriptase)-coupled polymerase chain reaction (PCR), Northern Blot, and/or RNase protection analyses. The degree of differences in expression levels need only be large enough to be visualized or measured via standard characterization techniques.

As used herein, the term "transformed cell" means a cell into which (or into predecessor or an ancestor of which) a nucleic acid molecule encoding a polypeptide of the invention has been introduced, by means of, for example, recombinant DNA techniques or viruses.

The nucleic acid molecules of the invention, for example, the, CTSZ and CD24 genes or their subsequences, can be inserted into a vector, as described below, which will facilitate expression of the insert. The nucleic acid molecules and the polypeptides they encode can be used directly as diagnostic or therapeutic agents, or can be used (directly in the case of the polypeptide or indirectly in the case of a nucleic acid molecule) to generate antibodies that, in turn, are clinically useful as a therapeutic or diagnostic agent. Accordingly, vectors containing the nucleic acids of the invention, cells transfected with these vectors, the polypeptides expressed, and antibodies generated against either the entire polypeptide or an antigenic fragment thereof, are among the aspects of the invention.

A "structural gene" is a DNA sequence that is transcribed into messenger RNA (mRNA) which is then translated into a sequence of amino acids characteristic of a specific polypeptide.

An "isolated DNA molecule" is a fragment of DNA that has been separated from the chromosomal or genomic DNA of an organism. Isolation also is defined to connote a degree of separation from original source or surroundings. For example, a cloned DNA molecule encoding an avidin gene is an isolated DNA molecule. Another example of an isolated DNA molecule is a chemically-synthesized DNA molecule, or enzymatically-produced cDNA, that is not integrated in the genomic DNA of an organism. Isolated DNA molecules can be subjected to procedures known in the art to remove contaminants such that the DNA molecule is considered purified, that is, towards a more homogeneous state.

"Complementary DNA" (cDNA), often referred to as "copy DNA", is a single-stranded DNA molecule that is formed from an mRNA template by the enzyme reverse transcriptase. Typically, a primer complementary to portions of the mRNA is employed for the initiation of reverse transcription. Those skilled in the art also use the term "cDNA" to refer to a double-stranded DNA molecule that comprises such a single-stranded DNA molecule and its complement DNA strand.

The term "expression" refers to the biosynthesis of a gene product. For example, in the case of a structural gene, expression involves transcription of the structural gene into mRNA and the translation of mRNA into one or more polypeptides.

The term "amplification" refers to amplification, duplication, multiplication, or multiple expression of nucleic acids or a gene, in vivo or in vitro, yielding about 2.5 fold or more copies. For example, amplification of the CTSZ or CD24 gene resulting in a copy number greater than or equal to 2.5 is deemed to have been amplified. However, an increase in CTSZ or CD24 gene copy number less than 2.5 fold can still be considered as an amplification of the gene. The 2.5 fold figure is due to current detection limit, rather than a biological state.

The term "amplicon" refers to an amplification product containing one or more genes, which can be isolated from a precancerous or a cancerous cell or a tissue. CTSZ or CD24 amplicon is a result of amplification, duplication, multiplication, or multiple expression of nucleic acids or a gene, in vivo or in vitro. "Amplicon", as defined herein, also includes a completely or partially amplified CTSZ and/or CD24 gene(s). For example, an amplicon comprising a polynucleotide having at least about 90% sequence identity to SEQ ID NO:1 or SEQ ID NO:3 (CTSZ), SEQ ID NO:4 or SEQ ID NO:6 (CD24), or a fragment thereof.

A "cloning vector" is a nucleic acid molecule, for example, a plasmid, cosmid, or bacteriophage that has the capability of replicating autonomously in a host cell. Cloning vectors typically contain (i) one or a small number of restriction endonuclease recognition sites at which foreign DNA sequences can be inserted in a determinable fashion without loss of an essential biological function of the vector, and (ii) a marker gene that is suitable for use in the identification and selection of cells transformed or transfected with the cloning vector. Marker genes include genes that provide tetracycline resistance or ampicillin resistance, for example.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers.

A "recombinant host" may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

"Antisense RNA": In eukaryotes, RNA polymerase catalyzes the transcription of a structural gene to produce mRNA. A DNA molecule can be designed to contain an RNA polymerase template in which the RNA transcript has a sequence that is complementary to that of a preferred mRNA. The RNA transcript is termed an "antisense RNA". Antisense RNA molecules can inhibit mRNA expression (for example, Rylova et al., *Cancer Res,* 62(3):801–8, 2002; Shim et al., *Int. J. Cancer,* 94(1):6–15, 2001).

"Antisense DNA or DNA decoy or decoy molecule": With respect to a first nucleic acid molecule, a second DNA molecule or a second chimeric nucleic acid molecule that is created with a sequence, which is a complementary sequence or homologous to the complementary sequence of the first molecule or portions thereof, is referred to as the "antisense DNA or DNA decoy or decoy molecule" of the first molecule. The term "decoy molecule" also includes a nucleic molecule, which may be single or double stranded, that comprises DNA or PNA (peptide nucleic acid) (Mischiati et al., *Int. J. Mol. Med.,* 9(6):633–9, 2002), and that contains a sequence of a protein binding site, preferably a binding site for a regulatory protein and more preferably a binding site for a transcription factor. Applications of antisense nucleic acid molecules, including antisense DNA and decoy DNA molecules are known in the art, for example, Morishita et al, *Ann. N Y Acad. Sci.,* 947:294–301, 2001; Andratschke et al., *Anticancer Res,* 21:(5)3541–3550, 2001. Antisense DNA or PNA molecules can inhibit, block, or regulate function and/or expression of CTSZ and/or CD24 gene. Antisense and decoys can have different sequences, but can be directed against CTSZ and/or CD24 and can be administered concurrently or consecutively in any proportion, including equimolar proportions.

The term "operably linked" is used to describe the connection between regulatory elements and a gene or its coding region. That is, gene expression is typically placed under the control of certain regulatory elements, including constitutive or inducible promoters, tissue-specific regulatory elements, and enhancers. Such a gene or coding region is said to be "operably linked to" or "operatively linked to" or "operably associated with" the regulatory elements, meaning that the gene or coding region is controlled or influenced by the regulatory element.

"Sequence homology" is used to describe the sequence relationships between two or more nucleic acids, polynucleotides, proteins, or polypeptides, and is understood in the context of and in conjunction with the terms including: (a) reference sequence, (b) comparison window, (c) sequence identity, (d) percentage of sequence identity, and (e) substantial identity or "homologous."

(a) A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

(b) A "comparison window" includes reference to a contiguous and specified segment of a polynucleotide sequence, wherein the polynucleotide sequence may be compared to a reference sequence and wherein the portion of the polynucleotide sequence in the comparison window may comprise additions, substitutions, or deletions (i.e., gaps) compared to the reference sequence (which does not comprise additions, substitutions, or deletions) for optimal alignment of the two sequences. Generally, the comparison window is at least 20 contiguous nucleotides in length, and optionally can be 30, 40, 50, 100, or longer. Those of skill in the art understand that to avoid a misleadingly high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.,* 2: 482, 1981; by the homology alignment algorithm of Needleman and Wunsch, *J. Mol. Biol.,* 48: 443, 1970; by the search for similarity method of Pearson and Lipman, *Proc. Natl. Acad. Sci. USA,* 8: 2444, 1988; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 7 Science Dr., Madison, Wis., USA; the CLUSTAL program is well described by Higgins and Sharp, *Gene,* 73: 237–244, 1988; Corpet, et al., *Nucleic Acids Research,* 16:881–90, 1988; Huang, et al., *Computer Applications in the Biosciences,* 8:1–6, 1992; and Pearson, et al., *Methods in Molecular Biology,* 24:7–331, 1994. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology,* Chapter 19, Ausubel, et al., Eds., Greene Publishing and Wiley-Interscience, New York, 1995. New versions of the above programs or new programs altogether will undoubtedly become available in the future, and can be used with the present invention.

Unless otherwise stated, sequence identity/similarity values provided herein refer to the value obtained using the BLAST 2.0 suite of programs, or their successors, using default parameters. Altschul et al., *Nucleic Acids Res,* 2:3389–3402, 1997. It is to be understood that default settings of these parameters can be readily changed as needed in the future.

As those ordinary skilled in the art will understand, BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163, 1993) and XNU (Claverie and States, *Comput. Chem.*, 17:191–1, 1993) low-complexity filters can be employed alone or in combination.

(c) "Sequence identity" or "identity" in the context of two nucleic acid or polypeptide sequences includes reference to the residues in the two sequences which are the same when aligned for maximum correspondence over a specified comparison window, and can take into consideration additions, deletions and substitutions. When percentage of sequence identity is used in reference to proteins it is recognized that residue positions which are not identical often differ by conservative amino acid substitutions, where amino acid residues are substituted for other amino acid residues with similar chemical properties (for example, charge or hydrophobicity) and therefore do not deleteriously change the functional properties of the molecule. Where sequences differ in conservative substitutions, the percent sequence identity may be adjusted upwards to correct for the conservative nature of the substitution. Sequences which differ by such conservative substitutions are said to have sequence similarity. Approaches for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers and Miller, *Computer Applic. Biol. Sci.*, 4: 11–17, 1988, for example, as implemented in the program PC/GENE (Intelligenetics, Mountain View, Calif., USA).

(d) "Percentage of sequence identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" or "homologous" in their various grammatical forms in the context of polynucleotides means that a polynucleotide comprises a sequence that has a desired identity, for example, at least 60% identity, preferably at least 70% sequence identity, more preferably at least 80%, still more preferably at least 90% and even more preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and even more preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, for example, when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid, although such cross-reactivity is not required for two polypeptides to be deemed substantially identical.

(e) (ii) The term "substantial identity" or "homologous" in their various grammatical forms in the context of peptides indicates that a peptide comprises a sequence that has a desired identity, for example, at least 60% identity, preferably at least 70% sequence identity to a reference sequence, more preferably 80%, still more preferably 85%, even more preferably at least 90% or 95% sequence identity to the reference sequence over a specified comparison window. Preferably, optimal alignment is conducted using the homology alignment algorithm of Needleman and Wunsch, *J. Mol. Biol.*, 48:443, 1970. An indication that two peptide sequences are substantially identical is that one peptide is immunologically reactive with antibodies raised against the second peptide, although such cross-reactivity is not required for two polypeptides to be deemed substantially identical. Thus, a peptide is substantially identical to a second peptide, for example, where the two peptides differ only by a conservative substitution. Peptides which are "substantially similar" share sequences as noted above except that residue positions which are not identical may differ by conservative amino acid changes. Conservative substitutions typically include, but are not limited to, substitutions within the following groups: glycine and alanine; valine, isoleucine, and leucine; aspartic acid and glutamic acid; asparagine and glutamine; serine and threonine; lysine and arginine; and phenylalanine and tyrosine, and others as known to the skilled person.

"Biological subject" as used herein refers to a target biological object obtained, reached, or collected in vivo or in situ, that contains or is suspected of containing nucleic acids or polypeptides of CTSZ and/or CD24. A biological subject is typically of eukaryotic nature, for example, insects, protozoa, birds, fish, reptiles, and preferably a mammal, for example, rat, mouse, cow, dog, guinea pig, or rabbit, and more preferably a primate, for example, chimpanzees, or humans such as a patient in need of diagnostic review, treatment and/or monitoring of therapy.

"Biological sample" as used herein refers to a sample obtained from a biological subject, including sample of biological tissue or fluid origin, obtained, reached, or collected in vivo or in situ, that contains or is suspected of containing nucleic acids or polypeptides of CTSZ and/or CD24. A biological sample also includes samples from a region of a biological subject containing precancerous or cancer cells or tissues. Such samples can be, but are not limited to, organs, tissues, fractions and cells isolated from mammals including, humans such as a patient, mice, and rats. Biological samples also may include sections of the biological sample including tissues, for example, frozen sections taken for histologic purposes. A biological sample is typically of an eukaryotic origin, for example, insects, protozoa, birds, fish, reptiles, and preferably a mammal, for example, rat, mouse, cow, dog, guinea pig, or rabbit, and more preferably a primate, for example, chimpanzees or humans.

"Providing a biological subject or sample" means to obtain a biological subject in vivo or in situ, including tissue or cell sample for use in the methods described in the present invention. Most often, this will be done by removing a sample of cells from an animal, but also can be accomplished in vivo or in situ or by using previously isolated cells (for example, isolated from another person, at another time, and/or for another purpose).

A "control sample" refers to a sample of biological material representative of healthy, cancer-free animals. The level of CTSZ or CD24 in a control sample, or the encoding corresponding gene copy number, is desirably typical of the general population of normal, cancer-free animals of the same species. This sample either can be collected from an animal for the purpose of being used in the methods described in the present invention or it can be any biological material representative of normal, cancer-free animals suitable for use in the methods of this invention. A control sample also can be obtained from normal tissue from the animal that has cancer or is suspected of having cancer. A control sample also can refer to a given level of CTSZ or CD24, representative of the cancer-free population, that has been previously established based on measurements from normal, cancer-free animals. Alternatively, a biological control sample can refer to a sample that is obtained from a different individual or be a normalized value based on baseline data obtained from a population. Further, a control sample can be defined by a specific age, sex, ethnicity or other demographic parameters. In some situations, the control is implicit in the particular measurement. A typical control level for a gene is two copies per cell. An example of an implicit control is where a detection method can only detect CTSZ or CD24, or the corresponding gene copy number, when a level higher than that typical of a normal, cancer-free animal is present. Another example is in the context of an immunohistochemical assay where the control level for the assay is known. Other instances of such controls are within the knowledge of the skilled person.

"Data" includes, but is not limited to, information obtained that relates to "Biological Sample" or "Control Sample", as described above, wherein the information is applied in generating a test level for diagnostics, prevention, monitoring or therapeutic use. The present invention relates to methods for comparing and compiling data wherein the data is stored in electronic or paper formats. Electronic format can be selected from the group consisting of electronic mail, disk, compact disk (CD), digital versatile disk (DVD), memory card, memory chip, ROM or RAM, magnetic optical disk, tape, video, video clip, microfilm, internet, shared network, shared server and the like; wherein data is displayed, transmitted or analyzed via electronic transmission, video display, telecommunication, or by using any of the above stored formats; wherein data is compared and compiled at the site of sampling specimens or at a location where the data is transported following a process as described above.

"Overexpression" of a CTSZ or CD24 gene or an "increased," or "elevated," level of a CTSZ or CD24 polynucleotide or protein refers to a level of CTSZ or CD24 polynucleotide or polypeptide that, in comparison with a control level of CTSZ or CD24, is detectably higher. Comparison may be carried out by statistical analyses on numeric measurements of the expression; or, it may be done through visual examination of experimental results by qualified researchers.

A level of CTSZ or CD24 polypeptide or polynucleotide, that is "expected" in a control sample refers to a level that represents a typical, cancer-free sample, and from which an elevated, or diagnostic, presence of CTSZ or CD24 polypeptide or polynucleotide, can be distinguished. Preferably, an "expected" level will be controlled for such factors as the age, sex, medical history, etc. of the mammal, as well as for the particular biological subject being tested.

The phrase "functional effects" in the context of an assay or assays for testing compounds that modulate CTSZ or CD24 activity includes the determination of any parameter that is indirectly or directly under the influence of CTSZ or CD24, for example, a functional, physical, or chemical effect, for example, CTSZ or CD24 activity, the ability to induce gene amplification or overexpression in cancer cells, and to aggravate cancer cell proliferation. "Functional effects" include in vitro, in vivo, and ex vivo activities.

"Determining the functional effect" refers to assaying for a compound that increases or decreases a parameter that is indirectly or directly under the influence of CTSZ or CD24, for example, functional, physical, and chemical effects. Such functional effects can be measured by any means known to those skilled in the art, for example, changes in spectroscopic characteristics (for example, fluorescence, absorbance, refractive index), hydrodynamic (for example, shape), chromatographic, or solubility properties for the protein, measuring inducible markers or transcriptional activation of CTSZ or CD24; measuring binding activity or binding assays, for example, substrate binding, and measuring cellular proliferation; measuring signal transduction; or measuring cellular transformation.

"Inhibitors," "activators," "modulators," and "regulators" refer to molecules that activate, inhibit, modulate, regulate and/or block an identified function. Any molecule having potential to activate, inhibit, modulate, regulate and/or block an identified function can be a "test molecule," as described herein. For example, referring to oncogenic function or anti-apoptotic activity of CTSZ or CD24, such molecules may be identified using in vitro and in vivo assays of CTSZ or CD24, respectively. Inhibitors are compounds that partially or totally block CTSZ or CD24 activity, respectively, decrease, prevent, or delay their activation, or desensitize its cellular response. This may be accomplished by binding to CTSZ or CD24 proteins directly or via other intermediate molecules. An antagonist or an antibody that blocks CTSZ or CD24 activity, including inhibition of oncogenic function or anti-apoptotic activity of CTSZ or CD24, respectively, is considered to be such an inhibitor. Activators are compounds that bind to CTSZ or CD24 protein directly or via other intermediate molecules, thereby increasing or enhancing its activity, stimulating or accelerating its activation, or sensitizing its cellular response. An agonist of CTSZ or CD24 is considered to be such an activator. A modulator can be an inhibitor or activator. A modulator may or may not bind CTSZ or CD24 or its protein directly; it affects or changes the activity or activation of CTSZ or CD24 or the cellular sensitivity to CTSZ or CD24, respectively. A modulator also may be a compound, for example, a small molecule, that inhibits transcription of CTSZ or CD24 mRNA. A regulator of CTSZ or CD24 gene includes any element, for example, nucleic acid, peptide, polypeptide, protein, peptide nucleic acid or the like, that influence and/or control the transcription/expression of CTSZ or CD24 gene, respectively, or its coding region.

The group of inhibitors, activators, modulators and regulators of this invention also includes genetically modified versions of CTSZ or CD24, for example, versions with altered activity. The group thus is inclusive of the naturally occurring protein as well as synthetic ligands, antagonists, agonists, antibodies, small chemical molecules and the like.

"Assays for inhibitors, activators, modulators, or regulators" refer to experimental procedures including, for example, expressing CTSZ or CD24 in vitro, in cells, applying putative inhibitor, activator, modulator, or regulator compounds, and then determining the functional effects on CTSZ or CD24 activity or transcription, as described above. Samples that contain or are suspected of containing CTSZ or CD24 are treated with a potential activator, inhibitor, or modulator. The extent of activation, inhibition, or change is examined by comparing the activity measurement from the samples of interest to control samples. A threshold level is established to assess activation or inhibition. For example, inhibition of a CTSZ or CD24 polypeptide is considered achieved when the CTSZ or CD24 activity value relative to the control is 80% or lower. Similarly, activation of a CTSZ or CD24 polypeptide is considered achieved when the CTSZ or CD24 activity value relative to the control is two or more fold higher.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified. Various levels of purity may be applied as needed according to this invention in the different methodologies set forth herein; the customary purity standards known in the art may be used if no standard is otherwise specified.

An "isolated nucleic acid molecule" can refer to a nucleic acid molecule, depending upon the circumstance, that is separated from the 5' and 3' coding sequences of genes or gene fragments contiguous in the naturally occurring genome of an organism. The term "isolated nucleic acid molecule" also includes nucleic acid molecules which are not naturally occurring, for example, nucleic acid molecules created by recombinant DNA techniques.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral methyl phosphonates, 2-O-methyl ribonucleotides, and peptide-nucleic acids (PNAs).

Unless otherwise indicated, a particular nucleic acid sequence also implicitly encompasses conservatively modified variants thereof (for example, degenerate codon substitutions) and complementary sequences, as well as the sequence explicitly indicated. Specifically, degenerate codon substitutions may be achieved by generating sequences in which the third position of one or more selected (or all) codons is substituted with suitable mixed base and/or deoxyinosine residues (Batzer et al, *Nucleic Acid Res*, 19:081, 1991; Ohtsuka et al., *J. Biol. Chem.*, 260:2600–2608, 1985; Rossolini et al., *Mol. Cell Probes*, 8:91–98, 1994). The term nucleic acid can be used interchangeably with gene, cDNA, mRNA, oligonucleotide, and polynucleotide.

A "host cell" is a naturally occurring cell or a transformed cell or a transfected cell that contains an expression vector and supports the replication or expression of the expression vector. Host cells may be cultured cells, explants, cells in vivo, and the like. Host cells may be prokaryotic cells, for example, *E. coli*, or eukaryotic cells, for example, yeast, insect, amphibian, or mammalian cells, for example, Vero, CHO, HeLa, and others.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, γ-carboxyglutamate, and O-phosphoserine, phosphothreonine. "Amino acid analogs" refer to compounds that have the same basic chemical structure as a naturally occurring amino acid, i.e., a carbon that is bound to a hydrogen, a carboxyl group, an amino group, and an R group, for example, homoserine, norleucine, methionine sulfoxide, methionine methyl sulfonium. Such analogs have modified R groups (for example, norleucine) or modified peptide backbones, but retain the same basic chemical structure as a naturally occurring amino acid. "Amino acid mimetics" refers to chemical compounds that have a structure that is different from the general chemical structure of an amino acid, but that function in a manner similar to a naturally occurring amino acid. Amino acids and analogs are well known in the art.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" apply to both amino acid and nucleic acid sequences. With respect to particular nucleic acid sequences, conservatively modified variants refers to those nucleic acids which encode identical or similar amino acid sequences and include degenerate sequences. For example, the codons GCA, GCC, GCG and GCU all encode alanine. Thus, at every amino acid position where an alanine is specified, any of these codons can be used interchangeably in constructing a corresponding nucleotide sequence. The resulting nucleic acid variants are conservatively modified variants, since they encode the same protein (assuming that is the only alternation in the sequence). One skilled in the art recognizes that each codon in a nucleic acid, except for AUG (sole codon for methionine) and UGG (tryptophan), can be modified conservatively to yield a functionally-identical peptide or protein molecule.

As to amino acid sequences, one skilled in the art will recognize that substitutions, deletions, or additions to a polypeptide or protein sequence which alter, add or delete a single amino acid or a small number (typically less than about ten) of amino acids is a "conservatively modified variant" where the alteration results in the substitution of an amino acid with a chemically similar amino acid. Conservative substitutions are well known in the art and include, for example, the changes of: alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine. Other conservative and semi-conservative substitutions are known in the art and can be employed in practice of the present invention.

The terms "protein", "peptide" and "polypeptide" are used herein to describe any chain of amino acids, regardless of length or post-translational modification (for example, glycosylation or phosphorylation). Thus, the terms can be used interchangeably herein to refer to a polymer of amino acid residues. The terms also apply to amino acid polymers in which one or more amino acid residue is an artificial chemical mimetic of a corresponding naturally occurring amino acid. Thus, the term "polypeptide" includes full-length, naturally occurring proteins as well as recombinantly or synthetically produced polypeptides that correspond to a full-length naturally occurring protein or to particular domains or portions of a naturally occurring protein. The term also encompasses mature proteins which have an added amino-terminal methionine to facilitate expression in prokaryotic cells.

The polypeptides of the invention can be chemically synthesized or synthesized by recombinant DNA methods; or, they can be purified from tissues in which they are naturally expressed, according to standard biochemical methods of purification.

Also included in the invention are "functional polypeptides," which possess one or more of the biological functions or activities of a protein or polypeptide of the invention. These functions or activities include the ability to bind some or all of the proteins which normally bind to CTSZ or CD24 protein.

The functional polypeptides may contain a primary amino acid sequence that has been modified from that considered to be the standard sequence of CTSZ or CD24 protein described herein. Preferably these modifications are conservative amino acid substitutions, as described herein.

A "label" or a "detectable moiety" is a composition that when linked with the nucleic acid or protein molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens. A "labeled nucleic acid or oligonucleotide probe" is one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe may be detected by detecting the presence of the label bound to the nucleic acid or probe.

As used herein a "nucleic acid or oligonucleotide probe" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target gene of interest.

The phrase "selectively (or specifically) hybridizes to" refers to the binding, duplexing, or hybridizing of a molecule only to a particular nucleotide sequence under stringent hybridization conditions when that sequence is present in a complex mixture (for example, total cellular or library DNA or RNA).

The phrase "stringent hybridization conditions" refers to conditions under which a probe will hybridize to its target complementary sequence, typically in a complex mixture of nucleic acids, but to no other sequences. Stringent conditions are sequence-dependent and circumstance-dependent; for example, longer sequences can hybridize with specificity at higher temperatures. An extensive guide to the hybridization of nucleic acids is found in Tijssen, *Techniques in Biochemistry and Molecular Biology-Hybridization with Nucleic Probes*, "Overview of principles of hybridization and the strategy of nucleic acid assays" (1993). In the context of the present invention, as used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other.

Generally, stringent conditions are selected to be about 5 to 10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (for example, 10 to 50 nucleotides) and at least about 60° C. for long probes (for example, greater than 50 nucleotides). Stringent conditions also may be achieved with the addition of destabilizing agents, for example, formamide. For selective or specific hybridization, a positive signal is at least two times background, preferably 1 times background hybridization.

Exemplary stringent hybridization conditions can be as following, for example: 50% formamide, 5×SSC and 1% SDS, incubating at 42° C., or 5×SSC and 1% SDS, incubating at 65° C., with wash in 0.2×SSC and 0.1% SDS at 65° C. Alternative conditions include, for example, conditions at least as stringent as hybridization at 68° C. for 20 hours, followed by washing in 2×SSC, 0.1% SDS, twice for 30 minutes at 55° C. and three times for 15 minutes at 60° C. Another alternative set of conditions is hybridization in 6×SSC at about 45° C., followed by one or more washes in 0.2×SSC, 0.1% SDS at 50–65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C. to 95° C. for 30 sec. to 2 min., an annealing phase lasting 30 sec. to 2 min., and an extension phase of about 72° C. for 1 to 2 min.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The terms "about" or "approximately" in the context of numerical values and ranges refers to values or ranges that approximate or are close to the recited values or ranges such that the invention can perform as intended, such as having a desired amount of nucleic acids or polypeptides in a reaction mixture, as is apparent to the skilled person from the teachings contained herein. This is due, at least in part, to the varying properties of nucleic acid compositions, age, race, gender, anatomical and physiological variations and the inexactitude of biological systems. Thus, these terms encompass values beyond those resulting from systematic error.

"Antibody" refers to a polypeptide comprising a framework region encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 2 kDa) and one "heavy" chain (up to about 70 kDa). Antibodies exist, for example, as intact immunoglobulins or as a number of well-characterized fragments produced by digestion with various peptidases. While various antibody fragments are defined in terms of the digestion of an intact antibody, one of skill in the art will appreciate that such fragments may be synthesized de novo chemically or via recombinant DNA methodologies. Thus, the term antibody, as used herein, also includes antibody fragments produced by the modification of whole antibodies, those synthesized de novo using recombinant DNA methodologies (for example, single chain Fv), humanized antibodies, and those identified using phage display libraries (see, for example, Knappik et al., *J. Mol. Biol.*, 296:57–86, 2000; McCafferty et al., *Nature*, 348:2–4, 1990), for example. For preparation of antibodies—recombinant, monoclonal, or polyclonal antibodies—any technique known in the art can be used with this invention (see, for example, Kohler & Milstein, *Nature*, 256(5517):495–497, 1975; Kozbor et al., *Immunology Today*, 4:72, 1983; Cole et al., pp. 77–96 in *Monoclonal Antibodies* and *Cancer Therapy*, Alan R. Liss, Inc., 1998).

Techniques for the production of single chain antibodies (See U.S. Pat. No. 4,946,778) can be adapted to produce antibodies to polypeptides of this invention. Transgenic mice, or other organisms, for example, other mammals, may be used to express humanized antibodies. Phage display technology also can be used to identify antibodies and heteromeric Fab fragments that specifically bind to selected antigens (see, for example, McCafferty et al., *Nature*, 348:2–4, 1990; Marks et al., *Biotechnology*, 10(7):779–783, 1992).

The term antibody is used in the broadest sense including agonist, antagonist, and blocking or neutralizing antibodies.

"Blocking antibody" is a type of antibody, as described above, that refers to a polypeptide comprising variable and framework regions encoded by an immunoglobulin gene or fragments, homologues, analogs or mimetics thereof that specifically binds and blocks biological activities of an antigen; for example, a blocking antibody to CTSZ or CD24 blocks the oncogenic function. or anti-apoptotic activity of CTSZ or CD24 gene, respectively. A blocking antibody binds to critical regions of a polypeptide and thereby inhibits its function. Critical regions include protein-protein interaction sites, such as active sites, functional domains, ligand binding sites, and recognition sites. Blocking antibodies may be induced in mammals, for example in human, by repeated small injections of antigen, too small to produce strong hypersensitivity reactions. See Bellanti J A, *Immunology*, W B Saunders Co., p.131–368 (1971). Blocking antibodies play an important role in blocking the function of a marker protein and inhibiting tumorigenic growth. See, for example, Jopling et al., *J. Biol. Chem.*, 277(9):6864–73 (2002); Drebin et al., *Cell*, 41(3):697–706 (1985); Drebin et al., *Proc. Natl. Acad. Sci. USA*, 83(23):9129–33 (1986).

The term "tumor-cell killing" by anti-CTSZ or anti-CD24 blocking antibodies herein is meant any inhibition of tumor cell proliferation by means of blocking a function or binding to block a pathway related to tumor-cell proliferation. For example, anti-epidermal growth factor receptor monoclonal antibodies inhibit A431 tumor cell proliferation by blocking an autocrine pathway. See Mendelsohn et al., *Trans Assoc Am Physicians*, 100:173–8 (1987); Masui et al, *Cancer Res*, 44(3):1002–7 (1984).

The term "CTSZ- or CD24-oncogenic function-blocking antibody" herein is meant an anti-human CTSZ- or CD24- antibody whose interaction with the CTSZ or CD24 protein, respectively, inhibits the oncogenic function or anti-apoptotic activity of the protein, mediates tumor-cell killing mechanisms, or inhibits tumor-cell proliferation. In contrast to antibodies that merely bind to tumor cells expressing CTSZ or CD24, blocking antibodies against CTSZ or CD24 mediate tumor-cell killing by mechanisms related to the oncogenic function or anti-apoptotic activity of CTSZ or CD24. See Drebin et al., *Proc. Natl. Acad. Sci. USA*, 83(23):9129–33 (1986) for inhibition of tumorigenic growth; and Mendelsohn et al., *Trans Assoc Am Physicians*, 100:173–8 (1987), for an example of antibody-mediated anti-proliferative activity.

An "anti-CTSZ" antibody is an antibody or antibody fragment that specifically binds a polypeptide encoded by an CTSZ gene, mRNA, cDNA, or a subsequence thereof. Anti-CTSZ antibody also includes a blocking antibody that inhibits oncogenic function or anti-apoptotic activity of CTSZ. These antibodies can mediate anti-proliferative activity on tumor-cell growth.

An "anti-CD24" antibody is an antibody or antibody fragment that specifically binds a polypeptide encoded by an CD24 gene, mRNA, cDNA, or a subsequence thereof. Anti-CD24 antibody also includes a blocking antibody that inhibits oncogenic function or anti-apoptotic activity of CD24. These antibodies can mediate anti-proliferative activity on tumor-cell growth. "Cancer Vaccines" are substances that are designed to stimulate the immune system to launch an immune response against a specific target associated with a cancer. For a general overview on immunotherapy and vaccines for cancers, see Old L. J., *Scientific American*, September, 1996.

Vaccines may be preventative or therapeutic. Typically, preventative vaccines (for example, the flu vaccine) generally contain parts of polypeptides that stimulate the immune system to generate cells and/or other substances (for example, antibodies) that fight the target of the vaccines. Preventative vaccines must be given before exposure, concurrent with exposure, or shortly thereafter to the target (for example, the flu virus) in order to provide the immune system with enough time to activate and make the immune cells and substances that can attack the target. Preventative vaccines stimulate an immune response that can last for years or even an individual's lifetime.

Therapeutic vaccines are used to combat existing disease. Thus, the goal of a therapeutic cancer vaccine is not just to prevent disease, but rather to stimulate the immune system to attack existing cancerous cells. Because of the many types of cancers and because it is often unpredictable who might get cancer, among other reasons, the cancer vaccines currently being developed are therapeutic. As discussed further below, due to the difficulties associated with fighting an established cancer, most vaccines are used in combination with cytokines or adjuvants that help stimulate the immune response and/or are used in conjunction with conventional cancer therapies.

The immune system must be able to tolerate normal cells and to recognize and attack abnormal cells. To the immune system, a cancer cell may be different in very small ways from a normal cell. Therefore, the immune system often tolerates cancer cells rather than attacking them, which allows the cancer to grow and spread. Therefore, cancer vaccines must not only provoke an immune response, but also stimulate the immune system strongly enough to overcome this tolerance. The most effective anti-tumor immune responses are achieved by stimulating T cells, which can recognize and kill tumor cells directly. Therefore, most current cancer vaccines try to activate T cells directly, try to enlist antigen presenting cells (APCs) to activate T cells, or both. By way of example, researchers are attempting to enhance T cell activation by altering tumor cells so molecules that are normally only on APCs are now on the tumor cell, thus enabling the molecules to give T cells a stronger activating signal than the original tumor cells, and by evaluating cytokines and adjuvants to determine which are best at calling APCs to areas they are needed.

Cancer vaccines can be made from whole tumor cells or from substances contained by the tumor (for example, antigens). For a whole cell vaccine, tumor cells are removed from a patient(s), grown in the laboratory, and treated to ensure that they can no longer multiply and are incapable of infecting the patient. When whole tumor cells are injected into a person, an immune response against the antigens on the tumor cells is generated. There are two types of whole cell cancer vaccines: 1) autologous whole cell vaccines made with a patient's own whole, inactivated tumor cells; and 2) allogenic whole cell vaccines made with another individual's whole, inactivated tumor cells (or the tumor cells from several individuals). Antigen vaccines are not made of whole cells, but of one or more antigens contained by the tumor. Some antigens are common to all cancers of a particular type, while some are unique to an individual. A few antigens are shared between tumors of different types of cancer.

Antigens in an antigen vaccine may be delivered in several ways. For example, proteins or fragments thereof from the tumor cells can be given directly as the vaccine. Nucleic acids coding for those proteins can be given (for example, RNA or DNA vaccines). Furthermore, viral vectors can be engineered so that when they infect a human cell and the cell will make and display the tumor antigen on its surface. The viral vector should be capable of infecting only a small number of human cells in order to start an immune response, but not enough to make a person sick. Viruses also can be engineered to make cytokines or to display proteins on their surface that help activate immune cells. These can be given alone or with a vaccine to help the immune response. Finally, antibodies themselves may be used as antigens in a vaccine (anti-idiotype vaccines). In this way, an antibody to a tumor antigen is administered, then the B cells make antibodies to that antibody that also recognize the tumor cells.

Cancer vaccines frequently contain components to help boost the immune response. Cytokines (for example, IL-2), which are chemical messengers that recruit other immune cells to the site of attack and help killer T cells perform their function, are frequently employed. Similarly, adjuvants, substances derived from a wide variety of sources, including bacteria, have been shown to elicit immune cells to an area where they are needed. In some cases, cytokines and adjuvants are added to the cancer vaccine mixture, in other cases they are given separately.

Cancer vaccines are most frequently developed to target tumor antigens normally expressed on the cell surface (for example, membrane-bound receptors or subparts thereof). However, cancer vaccines also may be effective against intracellular antigens that are, in a tumor-specific manner, exposed on the cell surface. Many tumor antigens are intracellular proteins that are degraded and expressed on the cell surface complexed with, for example, HLA. Frequently, it is difficult to attack these antigens with antibody therapy because they are sparsely dispersed on the cell surface. However, cancer vaccines are a viable alternative therapeutic approach.

Cancer vaccines may prove most useful in preventing cancer recurrence after surgery, radiation or chemotherapy has reduced or eliminated the primary tumor.

The term "immunoassay" is an assay that utilizes the binding interaction between an antibody and an antigen. Typically, an immunoassay uses the specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at a level at least two times the background and do not substantially bind in a significant amount to other proteins present in the sample. Specific binding to an antibody under such conditions may require an antibody that is selected for its specificity for a particular protein. For example, antibodies raised to a particular CTSZ or CD24 polypeptide can be selected to obtain only those antibodies that are specifically immunoreactive with the CTSZ or CD24 polypeptide, respectively, and not with other proteins, except for polymorphic variants, orthologs, and alleles of the specific CTSZ or CD24 polypeptide. In addition, antibodies raised to a particular CTSZ or CD24 polypeptide ortholog can be selected to obtain only those antibodies that are specifically immunoreactive with the CTSZ or CD24 polypeptide ortholog, respectively, and not with other orthologous proteins, except for polymorphic variants, mutants, and alleles of the CTSZ or CD24 polypeptide ortholog. This selection may be achieved by subtracting out antibodies that cross-react with desired CTSZ or CD24 molecules, as appropriate. A variety of immunoassay formats may be used to select antibodies specifically immunoreactive with a particular protein. For example, solid-phase ELISA immunoassays are routinely used to select antibodies specifically immunoreactive with a protein. See, for example, Harlow & Lane, *Antibodies, A Laboratory Manual*, 1988, for a description of immunoassay formats and conditions that can be used to determine specific immunoreactivity.

The phrase "selectively associates with" refers to the ability of a nucleic acid to "selectively hybridize" with another as defined supra, or the ability of an antibody to "selectively (or specifically) bind" to a protein, as defined supra.

"siRNA" refers to small interfering RNAs, which also include short hairpin RNA (shRNA) (Paddison et al., *Genes & Dev.* 16: 948–958, 2002), that are capable of causing interference and can cause post-transcriptional silencing of specific genes in cells, for example, mammalian cells (including human cells) and in the body, for example, mammalian bodies (including humans). The phenomenon of RNA interference is described and discussed in Bass, *Nature*, 411:428–29, 2001; Elbashir et al., *Nature*, 411:494–98, 2001; and Fire et al., *Nature*, 391:806–11, 1998, wherein methods of making interfering RNA also are discussed. The siRNAs based upon the sequence disclosed herein (for example, GenBank Accession Nos. NM_001336 and NM_013230 for CTSZ and CD24, respectively) is typically less than 100 base pairs ("bps") in length and constituency and preferably is about 30 bps or shorter, and can be made by approaches known in the art, including the use of complementary DNA strands or synthetic approaches. The siRNAs are capable of causing interference and can cause post-transcriptional silencing of specific genes in cells, for example, mammalian cells (including human cells) and in the body, for example, mammalian bodies (including humans). Exemplary siRNAs according to the invention could have up to 30 bps, 29 bps, 25 bps, 22 bps, 21 bps, 20 bps, 15 bps, 10 bps, 5 bps or any integer thereabout or therebetween. According to the invention, siRNA having different sequences but directed against CTSZ or CD24 can be administered concurrently or consecutively in any proportion, including equimolar proportions.

The term "miRNA" refers to microRNA, a class of small RNA molecules or a small noncoding RNA molecules, that are capable of causing interference, inhibition of RNA translation into protein, and can cause post-transcriptional silencing of specific genes in cells, for example, mammalian cells (including human cells) and in the body, for example, mammalian bodies (including humans) (see, Zeng and Cullen, *RNA*, 9(1):112–123, 2003; Kidner and Martienssen *Trends Genet*, 19(1):13–6, 2003; Dennis C, *Nature*, 420 (6917):732, 2002; Couzin J, *Science* 298(5602):2296–7, 2002). Previously, the miRNAs were known as small temporal RNAs (stRNAs) belonged to a class of non-coding microRNAs, which have been shown to control gene expression either by repressing translation or by degrading the targeted mRNAs (see Couzin J, *Science* 298(5602):2296–7, 2002), which are generally 20–28 nt in length (see Finnegan et al., *Curr Biol*, 13(3):236–40, 2003; Ambros et al., *RNA* 9(3):277–279, 2003; Couzin J, *Science* 298(5602):2296–7, 2002). Unlike other RNAs (for example, siRNAs or shRNAs), miRNAs or stRNAs are not encoded by any microgenes, are generated from aberrant (probably double-stranded) RNAs by an enzyme called Dicer, which chops double-stranded RNA into little pieces (see Couzin J, *Science* 298(5602):2296–7, 2002). According to the invention, miRNA having different sequences but directed against CTSZ or CD24 can be administered concurrently or consecutively in any proportion, including equimolar proportions.

The term "transpene" refers to a nucleic acid sequence encoding, for example, one of the CTSZ or CD24 polypeptides, or an antisense transcript thereto, which is partly or entirely heterologous, i.e., foreign, to the transgenic organism or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (for example, it is inserted at a location which differs from that of the natural gene or its insertion results in a knockout). A transgene can include one or more transcriptional regulatory sequences and any other nucleic acid, (for example, an intron), that may be necessary for optimal expression of a selected nucleic acid.

By "transgenic" is meant any organism that includes a nucleic acid sequence, which is inserted into a cell and becomes a part of the genome of the animal that develops from that cell. Such a transgene may be partly or entirely heterologous to the transgenic animal.

Thus, for example, substitution of the naturally occurring CTSZ or CD24 gene for a gene from a second species results in an animal that produces the protein of the second species. Substitution of the naturally occurring gene for a gene having a mutation results in an animal that produces the mutated protein. A transgenic mouse, see below, expressing the human CTSZ or CD24 protein can be generated by direct replacement of the mouse CTSZ or CD24 subunit with the human gene. These transgenic animals can be critical for drug antagonist studies on animal models for human diseases, and for eventual treatment of disorders or diseases associated with the respective genes. Transgenic mice carrying these mutations will be extremely useful in studying this disease.

A "transgenic animal" refers to any animal, preferably a non-human mammal, that is chimeric, and is achievable with most vertebrate species. Such species include, but are not limited to, non-human mammals, including rodents, for example, mice and rats; rabbits; birds or amphibians; ovines, for example, sheep and goats; porcines, for example, pigs; and bovines, for example, cattle and buffalo; in which one. or more of the cells of the animal contains heterologous nucleic acid introduced by way of human intervention, for example, by transgenic techniques well known in the art. The nucleic acid is introduced into the cell, directly or indirectly by introduction into a precursor of the cell, by way of deliberate genetic manipulation, for example, by microinjection or by infection with a recombinant virus. The term genetic manipulation does not include classical crossbreeding, or sexual fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the CTSZ or CD24 proteins, for example, either agonistic or antagonistic forms. However, transgenic animals in which the recombinant CTSZ or CD24 gene is silent also are contemplated. Moreover, "transgenic animal" also includes those recombinant animals in which gene disruption of one or more CTSZ or CD24 gene is caused by human intervention, including both recombination and antisense techniques. The transgene can be limited to somatic cells or be placed into the germline.

Methods of obtaining transgenic animals are described in, for example, Puhler, A., Ed., *Genetic Engineering of Animals,* VCH Pub., 1993; Murphy and Carter, Eds., *Transgenesis Techniques: Principles and Protocols* (*Methods in Molecular Biology*, Vol. 18), 1993; and Pinkert, Calif., Ed., *Transgenic Animal Technology: A Laboratory Handbook*, Academic Press, 1994.

The term "knockout construct" refers to a nucleotide sequence that is designed to decrease or suppress expression of a polypeptide encoded by an endogenous gene in one or more cells of a mammal. The nucleotide sequence used as the knockout construct is typically comprised of (1) DNA from some portion of the endogenous gene (one or more exon sequences, intron sequences, and/or promoter sequences) to be suppressed and (2) a marker sequence used to detect the presence of the knockout construct in the cell. The knockout construct can be inserted into a cell containing the endogenous gene to be knocked out. The knockout construct can then integrate with one or both alleles of an endogenous gene, for example, CTSZ or CD24 gene, and such integration of the knockout construct can prevent or interrupt transcription of the full-length endogenous gene. Integration of the knockout construct into the cellular chromosomal DNA is typically accomplished via homologous recombination (i.e., regions of the knockout construct that are homologous or complementary to endogenous DNA sequences can hybridize to each other when the knockout construct is inserted into the cell; these regions can then recombine so that the knockout construct is incorporated into the corresponding position of the endogenous DNA).

A transgenic animal carrying a "knockout" of CTSZ or CD24 gene, would be useful for the establishment of a non-human model for diseases involving such proteins, and to distinguish between the activities of the different CTSZ or CD24 proteins in an in vivo system. "Knockout mice" refers to mice whose native or endogenous CTSZ or CD24 allele or alleles have been disrupted by homologous recombination or the like and which produce no functional CTSZ or CD24 of its own. Knockout mice may be produced in accordance with techniques known in the art, for example, Thomas, et al., *Immunol,* 163:978–84, 1999; Kanakaraj, et al., *J Exp Med.* 187:2073–9, 1998; or Yeh et al., *Immunity,* 7:715–725, 1997.

Aptamers: An aptamer is a peptide, a peptide-like, a nucleic acid, or a nucleic acid-like molecule that is capable of binding to a specific molecule (for example, CTSZ or CD24) of interest with high affinity and specificity. An aptamer also can be a peptide or a nucleic acid molecule that mimics the three dimensional structure of active portions of the peptides or the nucleic acid molecules of the invention. (see, for example, James W., *Current Opinion in Pharmacology,* 1:540–546 (2001); Colas et al., *Nature* 380:548–550 (1996); Tuerk and Gold, *Science* 249:505 (1990); Ellington and Szostak, *Nature* 346:818 (1990)). The specific binding molecule of the invention may be a chemical mimetic; for example, a synthetic peptide aptamer or peptidomimetic. It is preferably a short oligomer selected for binding affinity and bioavailability (for example, passage across the plasma and nuclear membranes, resistance to hydrolysis of oligomeric linkages, adsorbance into cellular tissue, and resistance to metabolic breakdown). The chemical mimetic may be chemically synthesized with at least one non-natural analog of a nucleoside or amino acid (for example, modified base or ribose, designer or non-classical amino acid, D or L optical isomer). Modification also may take the form of acylation, glycosylation, methylation, phosphorylation, sulfation, or combinations thereof. Oligomeric linkages may be phosphodiester or peptide bonds; linkages comprised of a phosphorus, nitrogen, sulfur, oxygen, or carbon atom (for example, phosphorothionate, disulfide, lactam, or lactone bond); or combinations thereof. The chemical mimetic may have significant secondary structure (for example, a ribozyme) or be constrained (for example, a cyclic peptide).

Peptide Aptamer: A peptide aptamer is a polypeptide or a polypeptide-like molecule that is capable of binding to a specific molecule (for example, CTSZ or CD24) of interest with high affinity and specificity. A peptide aptamer also can be a polypeptide molecule that mimics the three dimensional structure of active portions of the polypeptide molecules of the invention. A peptide-aptamer can be designed to mimic the recognition function of complementarity determining regions of immunoglobulins, for example. The aptamer can recognize different epitopes on the protein surface (for example, CTSZ or CD24) with dissociation equilibrium constants in the nanomolar range; those inhibit the protein (for example, CTSZ or CD24, respectively) activity. Peptide aptamers are analogous to monoclonal antibodies, with the advantages that they can be isolated together with their coding genes, that their small size facilitates solution of their structures, and that they can be designed to function inside cells.

An peptide aptamer is typically between about 3 and about 100 amino acids or the like in length. More commonly, an aptamer is between about 10 and about 35 amino acids or the like in length. Peptide-aptamers may be prepared by any known method, including synthetic, recombinant, and purification methods (James W., *Current Opinion in Pharmacology,* 1:540–546 (2001); Colas et al., *Nature* 380:548–550 (1996)).

The instant invention also provides aptamers of CTSZ and CD24 peptides. In one aspect, the invention provides aptamers of isolated polypeptides comprising at least one active fragment having substantially homologous sequence of CTSZ or CD24 peptides (for example, SEQ ID NO:2 or SEQ ID NO:5, respectively, or any fragment thereof). The instant aptamers are peptide molecules that are capable of binding to a protein or other molecule, or mimic the three dimensional structure of the active portion of the peptides of the invention.

Nucleic Acid Aptamer: A nucleic acid aptamer is a nucleic acid or a nucleic acid-like molecule that is capable of binding to a specific molecule (for example, CTSZ or CD24) of interest with high affinity and specificity. A nucleic acid aptamer also can be a nucleic acid molecule that mimics the three dimensional structure of active portions of the nucleic acid molecules of the invention. A nucleic acid-aptamer is typically between about 9 and about 300 nucleotides or the like in length. More commonly, an aptamer is between about 30 and about 100 nucleotides or the like in length. Nucleic acid-aptamers may be prepared by any known method, including synthetic, recombinant, and purification methods (James W., Current Opinion in Pharmacology, 1:540–546 (2001); Colas et al., Nature 380:548–550 (1996)).

According to one aspect of the invention, aptamers of the instant invention include non-modified or chemically modified RNA, DNA, PNA or polynucleotides. The method of selection may be by, but is not limited to, affinity chromatography and the method of amplification by reverse transcription (RT) or polymerase chain reaction (PCR). Aptamers have specific binding regions which are capable of forming complexes with an intended target molecule in an environment wherein other substances in the same environment are not complexed to the nucleic acid.

The instant invention also provides aptamers of CTSZ and CD24 polynucleotides. In another aspect, the invention provides aptamers of isolated polynucleotides comprising at least one active fragment having substantially homologous sequence of CTSZ and CD24 polynucleotides (for example, SEQ ID NO:1 or SEQ ID NO:3 and SEQ ID NO:4 or SEQ ID NO:6, respectively, or any fragment thereof). The instant aptamers are nucleic acid molecules that are capable of binding to a nucleic acid or other molecule, or mimic the three dimensional structure of the active portion of the nucleic acids of the invention.

The invention also provides nucleic acids (for example, mRNA molecules) that include an aptamer as well as a coding region for a regulatory polypeptide. The aptamer is positioned in the nucleic acid molecule such that binding of a ligand to the aptamer prevents translation of the regulatory polypeptide.

CTSZ: The term "CTSZ" refers to CTSZ nucleic acid (DNA and RNA) or protein (or polypeptide), and can include their polymorphic variants, alleles, mutants, and interspecies homologs that have (i) substantial nucleotide sequence homology (for example, at least 60% identity, preferably at least 70% sequence identity, more preferably at least 80%, still more preferably at least 90% and even more preferably at least 95%) with the nucleotide sequence of the GenBank Accession No. NM_001336 (protein ID. NP_001327.2), Homo sapiens Cathepsin Z (CTSZ) (Accession Nos. for Homo sapiens CTSZ: NM_001336, AF136273, AF136276, AL109840, AF073890, AF009923, XM_030699; and AF032906); or (ii) at least 65% sequence homology with the amino acid sequence of the GenBank protein_id NP_001327.2 (CTSZ); or (iii) substantial nucleotide sequence homology (for example, at least 60% identity, preferably at least 70% sequence identity to a reference sequence, more preferably 80%, still more preferably 85%, even more preferably at least 90% or 95%) with the nucleotide sequence as set forth in SEQ ID NO:1 or SEQ ID NO:3; or (iv) substantial sequence homology with the encoded amino acid sequence (for example, SEQ ID NO:2).

CTSZ polynucleotides or polypeptides are typically from a mammal including, but not limited to, human, rat, mouse, hamster, cow, pig, horse, sheep, or any mammal. A "CTSZ polynucleotide" and a "CTSZ polypeptide," may be either naturally occurring, recombinant, or synthetic (for example, via chemical synthesis).

CTSZ DNA sequence contains 1501 base pairs (see SEQ ID NO:1), encoding a protein of 303 amino acids (see SEQ ID NO:2). CTSZ coding-sequence contains 912 base pairs (see SEQ ID NO:3)

GenBank Accessions Nos. for Homo sapiens CTSZ: NM_001336, AF136273, AF136276, AL109840, AF073890, AF009923, XM_030699, and AF032906.

GenBank Accessions Nos. for Mouse CTSZ: AK004095, NM_022325, AJ242663, AF136277, AF136278, AK002710, AK008370, AK010912, BC008619, AF197479.

According to an aspect of the present invention, it has been determined that CTSZ is amplified and overexpressed in human cancers, including colon cancer, ovarian cancer, or breast cancer. Human chromosome region 20q13 is one of the most frequently amplified regions in human cancers including colon cancer, ovarian cancer, or breast cancer. More than one gene is located in this region. In a process of characterizing one of the 20q13 amplicons, CTSZ was found amplified in human colon cancer, ovarian cancer, and breast cancer, and other tumor samples. Studies have shown that such amplification is usually associated with aggressive histologic types. Therefore, amplification of tumor-promoting gene(s) located on 20q13 can play an important role in the development and/or progression of cancers including primary colon cancer, ovarian cancer, or breast cancer, particularly those of the invasive histology.

CTSZ was found by DNA Microarray analysis of human tumor cell lines for DNA amplification. See, for example, U.S. Pat. No. 6,232,068; Pollack et al, Nat. Genet. 23(1): 41–46, (1999) and other approaches known in the art. Further analysis provided evidence that CTSZ gene is present at the epicenter.

The overexpression of CTSZ was found amplified in over 23% (9/38 samples) of colon tumor samples, in over 23% (10/42 samples) in breast tumors samples and in over 12% (3/24 samples) in ovarian tumor samples (see Table 1). Studies have shown that this amplification is usually associated with aggressive histologic types. Amplification of tumor-promoting gene(s) located on 20q13 may play an important role in the development and/or progression of a substantial proportion of primary colon cancer, particularly those of the invasive histology.

Amplified cell lines or tumors (for example, colon, breast, or ovarian) were examined for DNA copy number of nearby genes and DNA sequences that map to the boundaries of the amplified regions. TaqMan epicenter data for CTSZ is shown in FIG. 1.

Quantitative RT-PCR analysis with TaqMan probes showed that CTSZ was found overexpressed in over 40% (13/32 samples tested) of human colon tumor samples, over 33% (4/12 samples tested) of human breast tumor samples, and over 23% (4/17 samples tested) of human ovarian tumor samples (see Tables 1). All amplified colon tumors overexpress CTSZ mRNA (see Table 1).

The folds of amplification and folds of overexpression were measured by TaqMan and RT-TaqMan respectively using CTSZ specific fluorogenic TaqMan probes. There is a good correlation between and amplification and overexpression (see Table 1).

CD24: The term "CD24" refers to CD24 nucleic acid (DNA and RNA) or protein (or polypeptide), and can include their polymorphic variants, alleles, mutants, and interspecies homologs that have (i) substantial nucleotide sequence homology (for example, at least 60% identity, preferably at least 70% sequence identity, more preferably at least 80%, still more preferably at least 90% and even more preferably at least 95%) with the nucleotide sequence of the GenBank Accession No. NM_013230 (protein ID. NP_037362.1), Homo sapiens CD24 (Accession No.: NM_013230); or (ii) at least 65% sequence homology with the amino acid sequence of the GenBank protein_id NP_037362.1 (sialoglycoprotein CD24); or (iii) substantial nucleotide sequence homology (for example, at least 60% identity, preferably at least 70% sequence identity to a reference sequence, more preferably 80%, still more preferably 85%, even more preferably at least 90% or 95%) with the nucleotide sequence as set forth in SEQ ID NO:4 or SEQ ID NO:6; or (iv) substantial sequence homology with the encoded amino acid sequence (for example, SEQ ID NO:5).

CD24 polynucleotides or polypeptides are typically from a mammal including, but not limited to, human, rat, mouse, hamster, cow, pig, horse, sheep, or any mammal. A "CD24 polynucleotide" and a "CD24 polypeptide," may be either naturally occurring, recombinant, or synthetic (for example, via chemical synthesis).

CD24 DNA sequence contains 2116 base pairs (see SEQ ID NO:4), CD24 coding sequence contains 243 base pairs (see SEQ ID NO:6), encoding a protein of 80 amino acids (see SEQ ID NO:5).

GenBank Accession No. for Homo sapiens CD24: NM_013230; Protein ID. NP_037362.1; and Protein Sequence PID:g7019343.

Unigene clusters for Homo sapiens CD24 antigen: Hs.286124.

The present invention utilizes CD24. According to one aspect of the present invention, it has been determined that CD24 is amplified and overexpressed in human cancers, including breast cancer. Human chromosome region 6q21 is one of the most frequently amplified regions in human cancers including breast cancer. More than one gene is located in this region. In a process of characterizing one of the 6q21 amplicons, CD24 was found amplified in human breast and other tumor samples. Studies have shown that such amplification is usually associated with aggressive histologic types. Therefore, amplification of tumor-promoting gene(s) located on 6q21 can play an important role in the development and/or progression of cancers including breast cancer, particularly those of the invasive histology.

CD24 was found by DNA Microarray analysis of human tumor cell lines for DNA amplification. See, for example, U.S. Pat. No. 6,232,068; Pollack et al., Nat. Genet. 23(1): 41–46, (1999) and other approaches known in the art. Further analysis provided evidence that CD24 gene is present at the epicenter.

Figure 2:
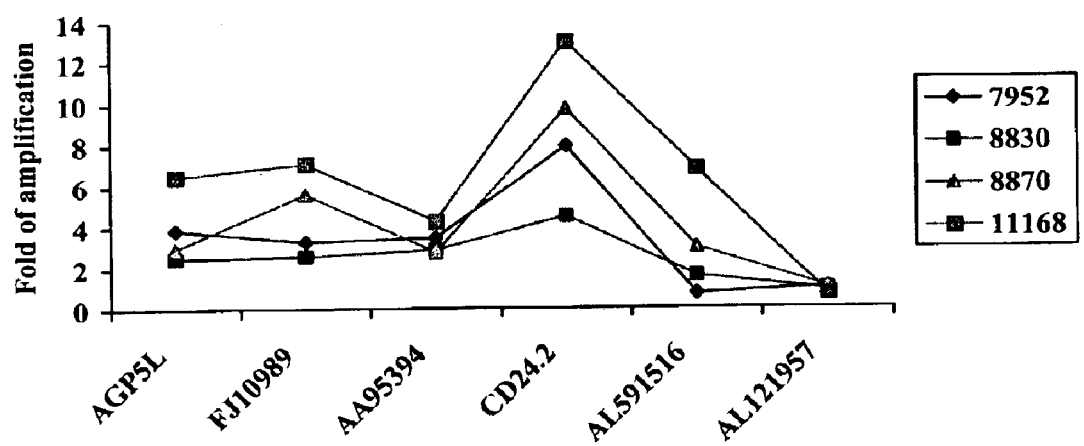
FIG. 2 depicts the epicenter mapping of human chromosome region 6q21 amplicon, which includes the CD24 locus. The number of DNA copies for each sample is plotted on the Y-axis, and the X-axis corresponds to nucleotide position based on Human Genome Project working draft sequence (http://genome.ucsc.edu/goldenPath/aug2001Tracks.html).

CD24 was found amplified in over 26% (9/34 samples) of breast tumor samples. Amplified cell lines or tumors (for example, breast) were examined for DNA copy number of nearby genes and DNA sequences that map to the boundaries of the amplified regions. TaqMan epicenter data for CD24 is shown in FIG. 2.

Quantitative RT-PCR analysis with TaqMan probes showed that CD24 was found overexpressed in 22% of human breast tumors (7/32 samples). All amplified breast tumors overexpress CD24 mRNA.

The folds of amplification and folds of overexpression were measured by TaqMan and RT-TaqMan respectively using CD24 specific fluorogenic TaqMan probes. There is a good correlation between and amplification and overexpression (see Table 2).

Detection of amplification of CTSZ or CD24 and/or overexpression of the corresponding mRNA or overproduction of the corresponding proteins, can be used to distinguish a malignant tumor biopsy from a benign biopsy. Therefore, the invention provides specific diagnostic and therapeutic uses for the CTSZ or CD24 gene and/or the protein that each encodes.

Amplification, overexpression, or overproduction of gene or gene products can influence the clinical outcome of the disease or its response to specific treatments. Detection of amplification of CTSZ or CD24 and/or overexpression of the corresponding mRNA or overproduction of the corresponding proteins, can be used to provide prognostic information or guide therapeutic treatment.

Small molecule inhibitors against CTSZ and/or CD24 activity also can be developed for the treatment of cancers.

More details on the role of CTSZ and CD24 in tumorigenesis are discussed in the sections below.

Amplification of CTSZ and CD24 Genes in Tumors:

The presence of a target gene that has undergone amplification in tumors is evaluated by determining the copy number of the target genes, i.e., the number of DNA sequences in a cell encoding the target protein. Generally, a normal diploid cell has two copies of a given autosomal gene. The copy number can be increased, however, by gene amplification or duplication, for example, in cancer cells, or reduced by deletion. Methods of evaluating the copy number of a particular gene are well known in the art, and include, inter alia, hybridization and amplification based assays.

Any of a number of hybridization based assays can be used to detect the copy number of the CTSZ or CD24 gene in the cells of a biological sample. One such method is Southern blot (see Ausubel et al., or Sambrook et al., supra), where the genomic DNA is typically fragmented, separated electrophoretically, transferred to a membrane, and subsequently hybridized to a CTSZ or CD24 specific probe. Comparison of the intensity of the hybridization signal from the probe for the target region with a signal from a control probe from a region of normal nonamplified, single-copied genomic DNA in the same genome provides an estimate of the relative CTSZ or CD24 copy number, corresponding to the specific probe used. An increased signal compared to control represents the presence of amplification.

A methodology for determining the copy number of the CTSZ or CD24 gene in a sample is in situ hybridization, for example, fluorescence in situ hybridization (FISH) (see Angerer, 1987 Meth. Enzymol., 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions.

Another alternative methodology for determining number of DNA copies is comparative genomic hybridization (CGH). In comparative genomic hybridization methods, a "test" collection of nucleic acids is labeled with a first label, while a second collection (for example, from a normal cell or tissue) is labeled with a second label. The ratio of hybridization of the nucleic acids is determined by the ratio of the first and second labels binding to each fiber in an array. Differences in the ratio of the signals from the two labels, for example, due to gene amplification in the test collection, is detected and the ratio provides a measure of the CTSZ or CD24 gene copy number, corresponding to the specific probe used. A cytogenetic representation of DNA copy-number variation can be generated by CGH, which provides fluorescence ratios along the length of chromosomes from differentially labeled test and reference genomic DNAs.

Hybridization protocols suitable for use with the methods of the invention are described, for example, in Albertson (1984) *EMBO J.* 3:1227–1234; Pinkel (1988) *Proc. Natl. Acad. Sci. USA*, 85:9138–9142; EPO Pub. No. 430:402; Methods in Molecular Biology, Vol. 33: In Situ Hybridization Protocols, Choo, ed., Humana Press, Totowa, N.J. (1994).

Amplification-based assays also can be used to measure the copy number of the CTSZ or CD24 gene. In such assays, the corresponding CTSZ or CD24 nucleic acid sequences act as a template in an amplification reaction (for example, Polymerase Chain Reaction or PCR). In a quantitative amplification, the amount of amplification product will be proportional to the amount of template in the original sample. Comparison to appropriate controls provides a measure of the copy number of the CTSZ or CD24 gene, corresponding to the specific probe used, according to the principles discussed above. Methods of real-time quantitative PCR using TaqMan probes are well known in the art. Detailed protocols for real-time quantitative PCR are provided, for example, for RNA in: Gibson et al., 1996, A novel method for real time quantitative RT-PCR. *Genome Res.*, 10:995–1001; and for DNA in: Heid et al., 1996, Real time quantitative PCR. *Genome Res.*, 10:986–994.

A TaqMan-based assay also can be used to quantify CTSZ or CD24 polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification (see, for example, http://www2.perkin-elmer.com).

Other suitable amplification methods include, but are not limited to, ligase chain reaction (LCR) (see, Wu and Wallace, *Genomics*, 4: 560, 1989; Landegren et al., *Science*, 241: 1077, 1988; and Barringer et al., *Gene*, 89:117, 1990), transcription amplification (Kwoh et al., *Proc. Natl. Acad. Sci. USA*, 86:1173, 1989), self-sustained sequence replication (Guatelli et al., *Proc Nat Acad Sci, USA* 87:1874, 1990), dot PCR, and linker adapter PCR, for example.

One powerful method for determining DNA copy numbers uses microarray-based platforms. Microarray technology may be used because it offers high resolution. For example, the traditional CGH generally has a 20 Mb limited mapping resolution; whereas in microarray-based CGH, the fluorescence ratios of the differentially labeled test and reference genomic DNAs provide a locus-by-locus measure of DNA copy-number variation, thereby achieving increased mapping resolution. Details of various microarray methods can be found in the literature. See, for example, U.S. Pat. No. 6,232,068; Pollack et al., *Nat. Genet.*, 23(1):41–6, (1999), and others.

As demonstrated in the Examples set forth herein, the CTSZ and/or CD24 genes are frequently amplified in certain cancers, particularly colon cancer, ovarian cancer, or breast cancer. Results showing a good correlation between CTSZ and CD24 DNA copy number increase and CTSZ or CD24 mRNA overexpression, respectively (see Tables 1–2). The CTSZ and CD24 genes have the characteristic features of overexpression, amplification, and the correlation between the two, and these features are shared with other well studied oncogenes (Yoshimoto et al., *JPN J Cancer Res*, 77(6): 540–5, 1986; Knuutila et al., *Am. J. Pathol.*, 152(5): 1107–23, 1998). The CTSZ and CD24 genes are accordingly used in the present invention as a target for cancer diagnosis, prevention, and treatment.

Frequent Overexpression of CTSZ and CD24 Genes in Tumors:

The expression levels of the CTSZ or CD24 gene in tumors cells were examined. As demonstrated in the examples infra, CTSZ and/or CD24 gene is overexpressed in cancers, including colon cancer, ovarian cancer, and breast cancer (See, Tables 1 and 2). Detection and quantification of the CTSZ or CD24 gene expression may be carried out through direct hybridization based assays or amplification based assays. The hybridization based techniques for measuring gene transcript are known to those skilled in the art (Sambrook et al., *Molecular Cloning: A Laboratory Manual*, 2d Ed. vol. 1–3, Cold Spring Harbor Press, NY, 1989). For example, one method for evaluating the presence, absence, or quantity of the CTSZ or CD24 gene is by Northern blot. Isolated mRNAs from a given biological sample are electrophoresed to separate the mRNA species, and transferred from the gel to a membrane, for example, a nitrocellulose or nylon filter. Labeled CTSZ or CD24 probes are then hybridized to the membrane to identify and quantify the respective mRNAs. The example of amplification based assays include RT-PCR, which is well known in the art (Ausubel et al., *Current Protocols in Molecular Biology*, eds. 1995 supplement). Quantitative RT-PCR is used preferably to allow the numerical comparison of the level of respective CTSZ or CD24 mRNAs in different samples.

Cancer Diagnosis, Therapies, and Vaccines Using CTSZ and CD24:

A. Overexpression and Amplification of the CTSZ and CD24 Genes:

The CTSZ and CD24 genes and their expressed gene products can be used for diagnosis, prognosis, rational drug design, and other therapeutic intervention of tumors and cancers (for example, a colon cancer, an ovarian cancer, or a breast cancer).

Detection and measurement of amplification and/or overexpression of the CTSZ and CD24 gene in a biological sample taken from a patient indicates that the patient may have developed a tumor. Particularly, the presence of amplified CTSZ and/or CD24 DNA leads to a diagnosis of cancer or precancerous condition, for example, a colon cancer, an ovarian cancer, or a breast cancer, with high probability of accuracy. The present invention therefore provides, in one aspect, methods for diagnosing or characterizing a cancer or tumor in a mammalian tissue by measuring the levels of CTSZ or CD24 mRNA expression in samples taken from the tissue of suspicion, and determining whether CTSZ or CD24 is overexpressed in the tissue. The various techniques, including hybridization based and amplification based methods, for measuring and evaluating mRNA levels are provided herein as discussed supra. The present invention, also provides, in other aspects, methods for diagnosing a cancer or tumor in a mammalian tissue by measuring the numbers of CTSZ and/or CD24 DNA copy in samples taken from the tissue of suspicion, and determining whether the CTSZ and/or CD24 gene is amplified in the tissue. The various techniques, including hybridization based and amplification based methods, for measuring and evaluating DNA copy numbers are provided herein as discussed supra. The present invention thus provides methods for detecting amplified genes at the DNA level and increased expression at the RNA level, wherein both the results are indicative of tumor progression.

B. Detection of the CTSZ or CD24 Protein:

According to the present invention, the detection of increased CTSZ and/or CD24 protein level in a biological subject also may suggest the presence of a precancerous or cancerous condition in the tissue source of the sample. Protein detection for tumor and, cancer diagnostics and prognostics can be carried out by immunoassays, for example, using antibodies directed against a target gene, for example, CTSZ or CD24. Any methods that are known in the art for protein detection and quantitation can be used in the methods of this invention, including, inter alia, electrophoresis, capillary electrophoresis, high performance liquid chromatography (HPLC), thin layer chromatography (TLC), hyperdiffusion chromatography, immunoelectrophoresis, radioimmunoassay (RIA), enzyme-linked immunosorbent assays (ELISAs), immuno-flouorescent assays, Western Blot, etc. Protein from the tissue or cell type to be analyzed may be isolated using standard techniques, for example, as described in Harlow and Lane, *Antibodies. A Laboratory Manual* (Cold Spring Harbor Laboratory Press, Cold Spring Harbor, N.Y. 1988).

The antibodies (or fragments thereof) useful in the present invention can, additionally, be employed histologically, as in immunofluorescence or immunoelectron microscopy, for in situ detection of target gene peptides. In situ detection can be accomplished by removing a histological specimen from a patient, and applying thereto a labeled antibody of the present invention. The antibody (or its fragment) is preferably applied by overlaying the labeled antibody (or fragment) onto a biological sample. Through the use of such a procedure, it is possible to determine not only the presence of the target gene product, for example, CTSZ or CD24 protein, but also its distribution in the examined tissue. Using the present invention, a skilled artisan will readily perceive that any of a wide variety of histological methods (for example, staining procedures) can be modified to achieve such in situ detection.

The biological sample that is subjected to protein detection can be brought in contact with and immobilized on a solid phase support or carrier, for example, nitrocellulose, or other solid support which is capable of immobilizing cells, cell particles, or soluble proteins. The support can then be washed with suitable buffers followed by treatment with the detectably labeled fingerprint gene specific antibody. The solid phase support can then be washed with the buffer a second time to remove unbound antibody. The amount of bound label on the solid support can then be detected by conventional means.

A target gene product-specific antibody, for example, an CTSZ or a CD24 antibody can be detectably labeled, in one aspect, by linking the same to an enzyme, for example, horseradish peroxidase, alkaline phosphatase, or glucoamylase, and using it in an enzyme immunoassay (EIA) (see, for example, Voller, A., 1978, The Enzyme Linked Immunosorbent Assay (ELISA), *Diagnostic Horizons*, 2:1–7; Voller et al., *J. Clin. Pathol.*, 31:507–520, 1978; Butler, J. E., *Meth. Enzymol.*, 73:482–523, 1981; Maggio, E. (ed.), *Enzyme Immunoassay*, CRC Press, Boca Raton, Fla., 1980; and Ishikawa et al. (eds), Enzyme Immunoassay, Kgaku Shoin, Tokyo, 1981). The enzyme bound to the antibody reacts with an appropriate substrate, preferably a chromogenic substrate, in such a manner as to produce a chemical moiety that can be detected, for example, by spectrophotometric or fluorimetric means, or by visual inspection.

In a related aspect, therefore, the present invention provides the use of CTSZ or CD24 antibodies in cancer diagnosis and intervention. Antibodies that specifically bind to CTSZ or CD24 protein and polypeptides can be produced by a variety of methods. Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

Such antibodies can be used, for example, in the detection of the target gene, CTSZ or CD24, or its fingerprint or pathway genes involved in a particular biological pathway, which may be of physiological or pathological importance. These potential pathways or fingerprint genes, for example, may interact with CTSZ or CD24 activity and be involved in tumorigenesis. The CTSZ or CD24 antibodies also can be used in a method for the inhibition of CTSZ or CD24 activity, respectively. Thus, such antibodies can be used in treating tumors and cancers (for example, colon cancer, ovarian cancer, or breast cancer); they also may be used in diagnostic procedures whereby patients are tested for abnormal levels of CTSZ or CD24 protein, and/or fingerprint or pathway gene product associated with CTSZ or CD24, and for the presence of abnormal forms of such protein.

To produce antibodies to CTSZ or CD24 protein, a host animal is immunized with the protein, or a portion thereof. Such host animals can include, but are not limited to, rabbits, mice, and rats. Various adjuvants can be used to increase the immunological response, depending on the host species, including but not limited to Freund's (complete and incomplete), mineral gels, for example, aluminum hydroxide, surface active substances, for example, lysolecithin, pluronic polyols, polyanions, peptides, oil emulsions, keyhole limpet hemocyanin (KLH), dinitrophenol (DNP), and potentially useful human adjuvants, for example, BCG (*Bacille Calmette-Guerin*) and *Corynebacterium parvum*.

Monoclonal antibodies, which are homogeneous populations of antibodies to a particular antigen, for example, CTSZ or CD24 as in the present invention, can be obtained by any technique which provides for the production of antibody molecules by continuous cell lines in culture. These include, but are not limited to the hybridoma technique of Kohler and Milstein, (*Nature*, 256:495–497, 1975; and U.S. Pat. No. 4,376,110), the human B-cell hybridoma technique (Kosbor et al., *Immunology Today*, 4:72, 1983; Cole et al., *Proc. Natl. Acad. Sci. USA*, 80:2026–2030, 1983), and the BV-hybridoma technique (Cole et al., *Monoclonal Antibodies And Cancer Therapy* (Alan R. Liss, Inc. 1985), pp. 77–96. Such antibodies can be of any immunoglobulin class including IgG, IgM, IgE, IgA, IgD and any subclass thereof. The hybridoma producing the mAb of this invention can be cultivated in vitro or in vivo. Production of high titers of mAbs in vivo makes this the presently preferred method of production.

In addition, techniques developed for the production of "chimeric antibodies" can be made by splicing the genes from a mouse antibody molecule of appropriate antigen specificity together with genes from a human antibody molecule of appropriate biological activity (see, Morrison et al., *Proc. Natl. Acad. Sci. USA,* 81:6851–6855, 1984; Neuberger et al., *Nature,* 312:604–608, 1984; Takeda et al., *Nature,* 314:452–454, 1985; and U.S. Pat. No. 4,816,567). A chimeric antibody is a molecule in which different portions are derived from different animal species, for example, those having a variable region derived from a murine mAb and a container region derived from human immunoglobulin.

Alternatively, techniques described for the production of single chain antibodies (for example, U.S. Pat. No. 4,946,778; Bird, *Science,* 242:423–426, 1988; Huston et al., *Proc. Natl. Acad. Sci. USA,* 85:5879–5883, 1988; and Ward et al., *Nature,* 334:544–546, 1989), and for making humanized monoclonal antibodies (U.S. Pat. No. 5,225,539), can be used to produce anti-differentially expressed or anti-pathway gene product antibodies.

Antibody fragments that recognize specific epitopes can be generated by known techniques. For example, such fragments include but are not limited to: the F(ab')$_2$ fragments that can be produced by pepsin digestion of the antibody molecule, and the Fab fragments that can be generated by reducing the disulfide bridges of the F(ab')$_2$ fragments. Alternatively, Fab expression libraries can be constructed (Huse et al., *Science,* 246:1275–1281, 1989) to allow rapid and easy identification of monoclonal Fab fragments with the desired specificity.

C. Use of CTSZ and CD24 Modulators in Cancer Diagnostics:

In addition to antibodies, the present invention provides, in another aspect, the diagnostic and therapeutic utilities of other molecules and compounds that interact with CTSZ or CD24 protein. Specifically, such compounds can include, but are not limited to proteins or peptides, comprising extracellular portions of transmembrane proteins of the target, if they exist. Exemplary peptides include soluble peptides, for example, Ig-tailed fusion peptides. Such compounds also can be obtained through the generation and screening of random peptide libraries (see, for example, Lam et al., *Nature,* 354:82–84, 1991; Houghton et al., *Nature,* 354:84–86, 1991), made of D- and/or L-configuration amino acids, phosphopeptides (including, but not limited to, members of random or partially degenerate phosphopeptide libraries; see, for example, Songyang et al., *Cell,* 72:767–778, 1993), and small organic or inorganic molecules. In this aspect, the present invention provides a number of methods and procedures to assay or identify compounds that bind to target, i.e., CTSZ or CD24 protein, or to any cellular protein that may interact with the target, and compounds that may interfere with the interaction of the target with other cellular proteins.

In vitro assay systems are provided that are capable of identifying compounds that specifically bind to the target gene product, for example, CTSZ or CD24 protein. The assays all involve the preparation of a reaction mixture of the target gene product, for example, CTSZ or CD24 protein and a test compound under conditions and for a time sufficient to allow the two components to interact and bind, thus forming a complex that can be removed and/or detected in the reaction mixture. These assays can be conducted in a variety of ways. For example, one method involves anchoring the target protein or the test substance to a solid phase, and detecting target protein—test compound complexes anchored to the solid phase at the end of the reaction. In one aspect of such a method, the target protein can be anchored onto a solid surface, and the test compound, which is not anchored, can be labeled, either directly or indirectly. In practice, microtiter plates can be used as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

To conduct the assay, the non-immobilized component is added to the coated surface containing the anchored component. After the reaction is complete, unreacted components are removed, for example, by washing, and complexes anchored on the solid surface are detected. Where the previously immobilized component is pre-labeled, the detection of label immobilized on the surface indicates that complexes were formed. Where the previously non-immobilized component is not pre-labeled, an indirect label can be used to detect complexes anchored on the surface; for example, using a labeled antibody specific for the immobilized component (the antibody, in turn, can be directly labeled or indirectly labeled with a labeled anti-Ig antibody). Alternatively, the reaction can be conducted in a liquid phase, the reaction products separated from unreacted components, and complexes detected, for example, using an immobilized antibody specific for a target gene or the test compound to anchor any complexes formed in solution, and a labeled antibody specific for the other component of the possible complex to detect anchored complexes.

Assays also are provided for identifying any cellular protein that may interact with the target protein, i.e., CTSZ or CD24 protein. Any method suitable for detecting protein-protein interactions can be used to identify novel interactions between target protein and cellular or extracellular proteins. Those cellular or extracellular proteins may be involved in certain cancers, for example, colon cancer, ovarian cancer, or breast cancer, and represent certain tumorigenic pathways including the target, for example, CTSZ or CD24. They may thus be denoted as pathway genes.

Methods, for example, co-immunoprecipitation and co-purification through gradients or chromatographic columns, can be used to identify protein-protein interactions engaged by the target protein. The amino acid sequence of the target protein, i.e., CTSZ or CD24 protein or a portion thereof, is useful in identifying the pathway gene products or other proteins that interact with CTSZ or CD24 protein. The amino acid sequence can be derived from the nucleotide sequence, or from published database records (SWISS-PROT, PIR, EMBL); it also can be ascertained using techniques well known to a skilled artisan, for example, the Edman degradation technique (see, for example, Creighton, *Proteins: Structures and Molecular Principles,* 1983, W. H. Freeman & Co., N.Y., 34–49). The nucleotide subsequences of the target gene, for example, CTSZ or CD24, can be used in a reaction mixture to screen for pathway gene sequences. Screening can be accomplished, for example, by standard hybridization or PCR techniques. Techniques for the generation of oligonucleotide mixtures and the screening are well known (see, for example, Ausubel, supra, and Innis et al. (eds.), *PCR Protocols: A Guide to Methods and Applications,* 1990, Academic Press, Inc., New York).

By way of example, the yeast two-hybrid system which is often used in detecting protein interactions in vivo is discussed herein. Chien et al. has reported the use of a version of the yeast two-hybrid system (*Proc. Natl. Acad. Sci. USA,* 1991, 88:9578–9582); it is commercially available from Clontech (Palo Alto, Calif.). Briefly, utilizing such a system, plasmids are constructed that encode two hybrid proteins: the first hybrid protein comprises the DNA-binding domain of a transcription factor, for example, activation protein, fused to a known protein, in this case, a protein known to be involved in a tumor or cancer, and the second hybrid protein comprises the transcription factor's activation domain fused to an unknown protein that is encoded by a cDNA which has been recombined into this plasmid as part of a cDNA library. The plasmids are transformed into a strain of the yeast *Saccharomyces cerevisiae* that contains a reporter gene, for example, lacZ, whose expression is regulated by the transcription factor's binding site. Either hybrid protein alone cannot activate transcription of the reporter gene. The DNA binding hybrid protein cannot activate transcription because it does not provide the activation domain function, and the activation domain hybrid protein cannot activate transcription because it lacks the domain required for binding to its target site, i.e., it cannot localize to the transcription activator protein's binding site. Interaction between the DNA binding hybrid protein and the library encoded protein reconstitutes the functional transcription factor and results in expression of the reporter gene, which is detected by an assay for the reporter gene product.

The two-hybrid system or similar methods can be used to screen activation domain libraries for proteins that interact with a known "bait" gene product. The CTSZ or CD24 gene product, involved in a number of tumors and cancers, is such a bait according to the present invention. Total genomic or cDNA sequences are fused to the DNA encoding an activation domain. This library and a plasmid encoding a hybrid of the bait gene product, i.e., CTSZ or CD24 protein or polypeptides, fused to the DNA-binding domain are co-transformed into a yeast reporter strain, and the resulting transformants are screened for those that express the reporter gene. For example, the bait gene CTSZ or CD24 can be cloned into a vector such that it is translationally fused to the DNA encoding the DNA-binding domain of the GAL4 protein. The colonies are purified and the plasmids responsible for reporter gene expression are isolated. The inserts in the plasmids are sequenced to identify the proteins encoded by the cDNA or genomic DNA.

A cDNA library of a cell or tissue source that expresses proteins predicted to interact with the bait gene product, for example, CTSZ or CD24, can be made using methods routinely practiced in the art. According to the particular system described herein, the library is generated by inserting the cDNA fragments into a vector such that they are translationally fused to the activation domain of GAL4. This library can be cotransformed along with the bait gene-GAL4 fusion plasmid into a yeast strain which contains a lacZ gene whose expression is controlled by a promoter which contains a GAL4 activation sequence. A cDNA encoded protein, fused to GAL4 activation domain, that interacts with the bait gene product will reconstitute an active GAL4 transcription factor and thereby drive expression of the lacZ gene. Colonies that express lacZ can be detected by their blue color in the presence of X-gal. Plasmids from such a blue colony can then be purified and used to produce and isolate the CTSZ- or CD24-interacting protein using techniques routinely practiced in the art.

In another aspect, the present invention also provides assays for compounds that interfere with gene and cellular protein interactions involving the target CTSZ or CD24. The target gene product, for example, CTSZ or CD24 protein, may interact in vivo with one or more cellular or extracellular macromolecules, for example, proteins and nucleic acid molecules. Such cellular and extracellular macromolecules are referred to as "binding partners." Compounds that disrupt such interactions can be used to regulate the activity of the target gene product, for example, CTSZ or CD24 protein, especially mutant target gene product. Such compounds can include, but are not limited to, molecules, for example, antibodies, peptides and other chemical compounds.

The assay systems all involve the preparation of a reaction mixture containing the target gene product CTSZ or CD24 protein, and the binding partner under conditions and for a time sufficient to allow the two products to interact and bind, thus forming a complex. To test a compound for inhibitory activity, the reaction mixture is prepared in the presence and absence of the test compound. The test compound can be initially included in the reaction mixture, or can be added at a time subsequent to the addition of a target gene product and its cellular or extracellular binding partner. Control reaction mixtures are incubated without the test compound or with a placebo. The formation of complexes between the target gene product CTSZ or CD24 protein and the cellular or extracellular binding partner is then detected. The formation of a complex in the control reaction, but not in the reaction mixture containing the test compound, indicates that the compound interferes with the interaction of the target gene product CTSZ or CD24 protein and the interactive binding partner. Additionally, complex formation within reaction mixtures containing the test compound and normal target gene product can be compared to complex formation within reaction mixtures containing the test compound and mutant target gene product. This comparison can be important in the situation where it is desirable to identify compounds that disrupt interactions of mutant but not normal target gene product.

The assays can be conducted in a heterogeneous or homogeneous format. Heterogeneous assays involve anchoring either the target gene product CTSZ or CD24 protein or the binding partner to a solid phase and detecting complexes anchored to the solid phase at the end of the reaction, as described above. In homogeneous assays, the entire reaction is carried out in a liquid phase, as described below. In either approach, the order of addition of reactants can be varied to obtain different information about the compounds being tested. For example, test compounds that interfere with the interaction between the target gene product CTSZ or CD24 protein and the binding partners, for example, by competition, can be identified by conducting the reaction in the presence of the test substance; i.e., by adding the test substance to the reaction mixture prior to or simultaneously with the target gene product CTSZ or CD24 protein and interactive cellular or extracellular binding partner. Alternatively, test compounds that disrupt preformed complexes, for example, compounds with higher binding constants that displace one of the components from the complex, can be tested by adding the test compound to the reaction mixture after complexes have been formed.

In a homogeneous assay, a preformed complex of the target gene product and the interactive cellular or extracellular binding partner product is prepared in which either the target gene products or their binding partners are labeled, but the signal generated by the label is quenched due to complex formation (see, for example, Rubenstein, U.S. Pat. No. 4,109,496). The addition of a test substance that competes with and displaces one of the species from the preformed complex will result in the generation of a signal above background. The test substances that disrupt the interaction between the target gene product CTSZ or CD24 protein and cellular or extracellular binding partners can thus be identified.

In one aspect, the target gene product CTSZ or CD24 protein can be prepared for immobilization using recombinant DNA techniques. For example, the target CTSZ or CD24 coding region can be fused to a glutathione-S-transferase (GST) gene using a fusion vector, for example, pGEX-5X-1, in such a manner that its binding activity is maintained in the resulting fusion product. The interactive cellular or extracellular binding partner product is purified and used to raise a monoclonal antibody, using methods routinely practiced in the art. This antibody can be labeled with the radioactive isotope $^{125}$I, for example, by methods routinely practiced in the art.

In a heterogeneous assay, the GST-Target gene fusion product is anchored, for example, to glutathione-agarose beads. The interactive cellular or extracellular binding partner is then added in the presence or absence of the test compound in a manner that allows interaction and binding to occur. At the end of the reaction period, unbound material is washed away, and the labeled monoclonal antibody can be added to the system and allowed to bind to the complexed components. The interaction between the target gene product CTSZ or CD24 protein and the interactive cellular or extracellular binding partner is detected by measuring the corresponding amount of radioactivity that remains associated with the glutathione-agarose beads. A successful inhibition of the interaction by the test compound will result in a decrease in measured radioactivity. Alternatively, the GST-target gene fusion product and the interactive cellular or extracellular binding partner can be mixed together in liquid in the absence of the solid glutathione-agarose beads. The test compound is added either during or after the binding partners are allowed to interact. This mixture is then added to the glutathione-agarose beads and unbound material is washed away. Again, the extent of inhibition of the binding partner interaction can be detected by adding the labeled antibody and measuring the radioactivity associated with the beads.

In other aspects of the invention, these same techniques are employed using peptide fragments that correspond to the binding domains of the target gene product, for example, CTSZ or CD24 protein and the interactive cellular or extracellular binding partner (where the binding partner is a product), in place of one or both of the full-length products. Any number of methods routinely practiced in the art can be used to identify and isolate the protein's binding site. These methods include, but are not limited to, mutagenesis of one of the genes encoding one of the products and screening for disruption of binding in a co-immunoprecipitation assay.

Additionally, compensating mutations in the gene encoding the second species in the complex can be selected. Sequence analysis of the genes encoding the respective products will reveal mutations that correspond to the region of the product involved in interactive binding. Alternatively, one product can be anchored to a solid surface using methods described above, and allowed to interact with and bind to its labeled binding partner, which has been treated with a proteolytic enzyme, for example, trypsin. After washing, a short, labeled peptide comprising the binding domain can remain associated with the solid material, which can be isolated and identified by amino acid sequencing. Also, once the gene coding for the cellular or extracellular binding partner product is obtained, short gene segments can be engineered to express peptide fragments of the product, which can then be tested for binding activity and purified or synthesized.

D. Methods for Cancer Treatment Using CTSZ and CD24 Modulators:

In another aspect, the present invention provides methods for treating or controlling a cancer or tumor and the symptoms associated therewith. Any of the binding compounds, for example, those identified in the aforementioned assay systems, can be tested for the ability to prevent and/or ameliorate symptoms of tumors and cancers (for example, colon cancer, ovarian cancer, or breast cancer). As used herein, inhibit, control, ameliorate, prevent, treat, and suppress collectively and interchangeably mean stopping or slowing cancer formation, development, or growth and eliminating or reducing cancer symptoms. Cell-based and animal model-based trial systems for evaluating the ability of the tested compounds to prevent and/or ameliorate tumors and cancer symptoms are used according to the present invention.

For example, cell based systems can be exposed to a compound suspected of ameliorating colon, ovarian, or breast tumor or cancer symptoms, at a sufficient concentration and for a time sufficient to elicit such an amelioration in the exposed populations of cells. After exposure, the population cells are examined to determine whether one or more tumor or cancer phenotypes representation in the populations has been altered to resemble a more normal or more wild-type, non-cancerous phenotype. Further, the levels of CTSZ or CD24 mRNA expression and DNA amplification within these cells may be determined, according to the methods provided herein. A decrease in the observed level of expression and amplification would indicate to a certain extent the successful intervention of tumors and cancers (for example, colon cancer, ovarian cancer, or breast cancer).

In addition, animal models can be used to identify compounds for use as drugs and pharmaceuticals that are capable of treating or suppressing symptoms of tumors and cancers. For example, animal models can be exposed to a test compound at a sufficient concentration and for a time sufficient to elicit such an amelioration in the exposed animals. The response of the animals to the exposure can be monitored by assessing the reversal of symptoms associated with the tumor or cancer, or by evaluating the changes in DNA copy number in cell populations and levels of mRNA expression of the target gene, for example, CTSZ or CD24. Any treatments which reverse any symptom of tumors and cancers, and/or which reduce overexpression and amplification of the target CTSZ or CD24 gene may be considered as candidates for therapy in humans. Dosages of test agents can be determined by deriving dose-response curves.

Moreover, fingerprint patterns or gene expression profiles can be characterized for known cell states, for example, normal or known pre-neoplastic, neoplastic, or metastatic states, within the cell- and/or animal-based model systems. Subsequently, these known fingerprint patterns can be compared to ascertain the ability of a test compound to modify such fingerprint patterns, and to cause the pattern to more closely resemble that of a normal fingerprint pattern. For example, administration of a compound which interacts with and affects CTSZ or CD24 gene expression and amplification may cause the fingerprint pattern of a precancerous or cancerous model system to more closely resemble a control, normal system; such a compound thus will have therapeutic utilities in treating the cancer. In other situations, administration of a compound may cause the fingerprint pattern of a control system to begin to mimic tumors and cancers (for example, colon cancer, ovarian cancer, or breast cancer); such a compound therefore acts as a tumorigenic agent, which in turn can serve as a target for therapeutic interventions of the cancer and its diagnosis.

E. Methods for Monitoring Efficacy of Cancer Treatment:

In a further aspect, the present invention provides methods for monitoring the efficacy of a therapeutic treatment regimen of cancer and methods for monitoring the efficacy of a compound in clinical trials or other research studies for inhibition of tumors. The monitoring can be accomplished by detecting and measuring, in the biological samples taken from a patient at various time points during the course of the application of a treatment regimen for treating a cancer or a clinical trial or other research studies, the changed levels of expression or amplification of the target gene, for example, CTSZ and/or CD24 in the cell population or sample. A level of expression and/or amplification that is lower in samples taken at the later time of the treatment or trial or a research study then those at the earlier date indicates that the treatment regimen is effective to control the cancer in the patient, or the compound is effective in inhibiting the tumor. The time course studies should be so designed that sufficient time is allowed for the treatment regimen or the compound to exert its effect.

Therefore, the influence of compounds on tumors and cancers can be monitored both in a clinical trial or other research studies and in a basic drug screening. In a clinical trial or other research studies, for example, tumor cells can be isolated from colon, ovarian, or breast tumor removed by surgery, and RNA prepared and analyzed by Northern blot analysis or TaqMan RT-PCR as described herein, or alternatively by measuring the amount of protein produced. The fingerprint expression profiles thus generated can serve as putative biomarkers for colon, ovarian, or breast tumor or cancer. Particularly, the expression of CTSZ or CD24 serves as one such biomarker. Thus, by monitoring the level of expression of the differentially or over-expressed genes, for example, CTSZ or CD24, an effective treatment protocol can be developed using suitable chemotherapeutic anticancer drugs.

F. Use of Additional Modulators to CTSZ and CD24 Nucleotides in Cancer Treatment:

In another further aspect of this invention, additional compounds and methods for treatment of tumors are provided. Symptoms of tumors and cancers can be controlled by, for example, target gene modulation, and/or by a depletion of the precancerous or cancerous cells. Target gene modulation can be of a negative or positive nature, depending on whether the target resembles a gene (for example, tumorigenic) or a tumor suppressor gene (for example, tumor suppressive). That is, inhibition, i.e., a negative modulation, of an oncogene-like target gene or stimulation, i.e., a positive modulation, of a tumor suppressor-like target gene will control or ameliorate the tumor or cancer in which the target gene is involved. More precisely, "negative modulation" refers to a reduction in the level and/or activity of target gene or its product, for example, CTSZ or CD24, relative to the level and/or activity of the target gene product in the absence of the modulatory treatment. "Positive modulation" refers to an increase in the level and/or activity of target gene product, for example, CTSZ or CD24, relative to the level and/or activity of target gene or its product in the absence of modulatory treatment. Particularly because CTSZ or CD24 shares many features with well known oncogenes as discussed supra, inhibition of the CTSZ or CD24 gene, its protein, or its activities will control or ameliorate precancerous or cancerous conditions, for example, colon cancer, ovarian cancer, or breast cancer.

The techniques to inhibit or suppress a target gene, for example, CTSZ or CD24 that are involved in cancers, i.e., the negative modulatory techniques are provided in the present invention. For example, compounds that exhibit negative modulatory activity on CTSZ and/or CD24 can be used in accordance with the invention to prevent and/or ameliorate symptoms of tumors and cancers (for example, colon cancer, ovarian cancer, or breast cancer). Such molecules can include, but are not limited to, peptides, phosphopeptides, small molecules (molecular weight below about 500 Daltons), large molecules (molecular weight above about 500 Daltons), or antibodies (including, for example, polyclonal, monoclonal, humanized, anti-idiotypic, chimeric or single chain antibodies, and Fab, F(ab')$_2$ and Fab expression library fragments, and epitope-binding fragments thereof), and nucleic acid molecules that interfere with replication, transcription, or translation of the CTSZ or CD24 gene (for example, antisense RNA, Antisense DNA, DNA decoy or decoy molecule, siRNAs, miRNA, triple helix forming molecules, and ribozymes, which can be administered in any combination).

Antisense, siRNAs, miRNAs, and ribozyme molecules that inhibit expression of a target gene, for example, CTSZ or CD24, can be used to reduce the level of the functional activities of the target gene and its product, for example, reduce the catalytic potency of CTSZ or CD24, respectively. Triple helix forming molecules, can be used in reducing the level of target gene activity. These molecules can be designed to reduce or inhibit either wild type, or if appropriate, mutant target gene activity.

For example, anti-sense RNA and DNA molecules act to directly block the translation of mRNA by hybridizing to targeted mRNA and preventing protein translation. With respect to antisense DNA or DNA decoy, oligodeoxyribonucleotides derived from the translation initiation site, for example, between the −10 and +10 regions of the target gene nucleotide sequence of interest, are preferred.

Ribozymes are enzymatic RNA molecules capable of catalyzing the specific cleavage of RNA. A review is provided in Rossi, *Current Biology*, 4:469–471 (1994). The mechanism of ribozyme action involves sequence-specific hybridization of the ribozyme molecule to complementary target RNA, followed by an endonucleolytic cleavage. A composition of ribozyme molecules must include one or more sequences complementary to the target gene mRNA, and must include a well-known catalytic sequence responsible for mRNA cleavage (U.S. Pat. No. 5,093,246). Engineered hammerhead motif ribozyme molecules that may specifically and efficiently catalyze internal cleavage of RNA sequences encoding target protein, for example, CTSZ or CD24 may be used according to this invention in cancer intervention.

Specific ribozyme cleavage sites within any potential RNA target are initially identified by scanning the molecule of interest, for example, CTSZ or CD24 RNA, for ribozyme cleavage sites which include the following sequences, GUA, GUU and GUC. Once identified, short RNA sequences of between 15 and 20 ribonucleotides corresponding to the region of the target gene, for example, CTSZ or CD24 containing the cleavage site can be evaluated for predicted structural features, for example, secondary structure, that can render an oligonucleotide sequence unsuitable. The suitability of candidate sequences also can be evaluated by testing their accessibility to hybridization with complementary oligonucleotides, using ribonuclease protection assays.

The CTSZ or CD24 gene sequences also can be employed in an RNA interference context. The phenomenon of RNA interference is described and discussed in Bass, Nature, 411: 428–29 (2001); Elbashir et al., Nature, 411: 494–98 (2001); and Fire et al., Nature, 391: 806–11 (1998), where methods of making interfering RNA also are discussed. The double-stranded RNA based upon the sequence disclosed herein (for example, GenBank Accession Nos. NM_001336, and NM_013230 for CTSZ and CD24, respectively) is typically less than 100 base pairs ("bps") in length and constituency and preferably is about 30 bps or shorter, and can be made by approaches known in the art, including the use of complementary DNA strands or synthetic approaches. The RNAs that are capable of causing interference can be referred to as small interfering RNAs (siRNA), microRNAs (miRNAs), and can cause post-transcriptional silencing of specific genes in cells, for example, mammalian cells (including human cells) and in the body, for example, mammalian bodies (including humans). Exemplary siRNAs according to the invention could have up to 30 bps, 29 bps, 25 bps, 22 bps, 21 bps, 20 bps, 15 bps, 10 bps, 5 bps or any number thereabout or therebetween.

Nucleic acid molecules that can associate together in a triple-stranded conformation (triple helix) and that thereby can be used to inhibit transcription of a target gene, should be single helices composed of deoxynucleotides. The base composition of these oligonucleotides must be designed to promote triple helix formation via Hoogsteen base pairing rules, which generally require sizeable stretches of either purines or pyrimidines on one strand of a duplex. Nucleotide sequences can be pyrimidine-based, which will result in TAT and CGC triplets across the three associated strands of the resulting triple helix. The pyrimidine-rich molecules provide bases complementary to a purine-rich region of a single strand of the duplex in a parallel orientation to that strand. In addition, nucleic acid molecules can be chosen that are purine-rich, for example, those that contain a stretch of G residues. These molecules will form a triple helix with a DNA duplex that is rich in GC pairs, in which the majority of the purine residues are located on a single strand of the targeted duplex, resulting in GGC triplets across the three strands in the triplex. Alternatively, the potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines on one strand of a duplex.

In instances wherein the antisense, ribozyme, siRNA, miRNA, and triple helix molecules described herein are used to reduce or inhibit mutant gene expression, it is possible that they also can effectively reduce or inhibit the transcription (for example, using a triple helix) and/or translation (for example, using antisense, ribozyme molecules) of mRNA produced by the normal target gene allele. These situations are pertinent to tumor suppressor genes whose normal levels in the cell or tissue need to be maintained while a mutant is being inhibited. To do this, nucleic acid molecules which are resistant to inhibition by any antisense, ribozyme or triple helix molecules used, and which encode and express target gene polypeptides that exhibit normal target gene activity, can be introduced into cells via gene therapy methods. Alternatively, when the target gene encodes an extracellular protein, it may be preferable to co-administer normal target gene protein into the cell or tissue to maintain the requisite level of cellular or tissue target gene activity. By contrast, in the case of oncogene-like target genes, for example, CTSZ or CD24, it is the respective normal wild type CTSZ or CD24 gene and its protein that need to be suppressed. Thus, any mutant or variants that are defective in CTSZ or CD24 function or that interferes or completely abolishes its normal function would be desirable for cancer treatment. Therefore, the same methodologies described above to safeguard normal gene alleles may be used in the present invention to safeguard the mutants of the target gene in the application of antisense, ribozyme, and triple helix treatment.

Anti-sense RNA and DNA or DNA decoy, ribozyme, and triple helix molecules of the invention can be prepared by standard methods known in the art for the synthesis of DNA and RNA molecules. These include techniques for chemically synthesizing oligodeoxyribonucleotides and oligoribonucleotides well known in the art, for example, solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which also include suitable RNA polymerase promoters, for example, the T7 or SP6 polymerase promoters. Alternatively, antisense cDNA constructs that synthesize antisense RNA constitutively or inducibly, depending on the promoter used, can be introduced stably into cell lines. Various well-known modifications to the DNA molecules can be introduced as a means for increasing intracellular stability and half-life. Possible modifications include, but are not limited to, the addition of flanking sequences of ribo- or deoxy-nucleotides to the 5' and/or 3' ends of the molecule, or the use of phosphorothioate or 2' O-methyl rather than phosphodiesterase linkages within the oligodeoxyribonucleotide backbone.

In this aspect, the present invention also provides negative modulatory techniques using antibodies. Antibodies can be generated which are both specific for a target gene product and which reduce target gene product activity; they can be administered when negative modulatory techniques are appropriate for the treatment of tumors and cancers, for example, in the case of CTSZ or CD24 antibodies for colon cancer, ovarian cancer, or breast cancer treatment.

In instances where the target gene protein to which the antibody is directed is intracellular, and whole antibodies are used, internalizing antibodies are preferred. However, lipofectin or liposomes can be used to deliver the antibody, or a fragment of the Fab region which binds to the target gene epitope, into cells. Where fragments of an antibody are used, the smallest inhibitory fragment which specifically binds to the binding domain of the protein is preferred. For example, peptides having an amino acid sequence corresponding to the domain of the variable region of the antibody that specifically binds to the target gene protein can be used. Such peptides can be synthesized chemically or produced by recombinant DNA technology using methods well known in the art (for example, see Creighton, 1983, supra; and Sambrook et al., 1989, supra). Alternatively, single chain neutralizing antibodies that bind to intracellular target gene product epitopes also can be administered. Such single chain antibodies can be administered, for example, by expressing nucleotide sequences encoding single-chain antibodies within the target cell population by using, for example, techniques, for example, those described in Marasco et al., *Proc. Natl. Acad. Sci. USA*, 90:7889–7893 (1993). When the target gene protein is extracellular, or is a transmembrane protein, any of the administration techniques known in the art which are appropriate for peptide administration can be used to effectively administer inhibitory target gene antibodies to their site of action. The methods of administration and pharmaceutical preparations are discussed below.

G. Cancer Vaccines Using CTSZ and/or CD24:

One aspect of the invention relates to methods for inducing an immunological response in a mammal which comprises inoculating the mammal with CTSZ and/or CD24 polypeptide, or a fragment thereof, adequate to produce antibody and/or T cell immune response to protect the mammal from cancers, including colon cancer, ovarian cancer, or breast cancer.

In another aspect, the invention relates to peptides derived from the CTSZ or CD24 amino acid sequence (see, for example, SEQ ID NO:2 and SEQ ID NO:5, respectively), where those skilled in the art would be aware that the peptides of the present invention, or analogs thereof, can be synthesized by automated instruments sold by a variety of manufacturers, can be commercially custom ordered and prepared, or can be expressed from suitable expression vectors as described above. The term amino acid analogs has been previously described in the specification and for purposes of describing peptides of the present invention, analogs can further include branched or non-linear peptides.

The present invention therefore provides pharmaceutical compositions comprising CTSZ and/or CD24 protein or peptides derived therefrom for use in vaccines and in immunotherapy methods. When used as vaccines to protect mammals against cancer, the pharmaceutical composition can comprise as an immunogen cell lysate from cells transfected with a recombinant expression vector or a culture supernatant containing the expressed protein. Alternatively, the immunogen is a partially or substantially purified recombinant protein or a synthetic peptide.

Vaccination can be conducted by conventional methods. For example, the immunogen can be used in a suitable diluent such as saline or water, or complete or incomplete adjuvants. Further, the immunogen may or may not be bound to a carrier to make the protein immunogenic. Examples of such carrier molecules include but are not limited to bovine serum albumin (BSA), keyhole limpet hemocyanin (KLH), tetanus toxoid, and the like. The immunogen can be administered by any route appropriate for antibody production such as intravenous, intraperitoneal, intramuscular, subcutaneous, and the like. The immunogen may be administered once or at periodic intervals until a significant titer of anti-CTSZ or anti-CD24 antibody is produced. The antibody may be detected in the serum using an immunoassay.

In another aspect, the present invention provides pharmaceutical compositions comprising nucleic acid sequence capable of directing host organism synthesis of a CTSZ or CD24 protein or of a peptide derived from the CTSZ or CD24 protein sequence. Such nucleic acid sequence may be inserted into a suitable expression vector by methods known to those skilled in the art. Expression vectors suitable for producing high efficiency gene transfer in vivo include, but are not limited to, retroviral, adenoviral and vaccinia viral vectors. Operational elements of such expression vectors are disclosed previously in the present specification and are known to one skilled in the art. Such expression vectors can be administered, for example, intravenously, intramuscularly, subcutaneously, intraperitoneally or orally.

Another aspect of the invention relates to methods for inducing an immunological response in a mammal which comprises inoculating the mammal with naked CTSZ nucleic acid and/or CD24 nucleic acid, or a fragment thereof, adequate to produce an immunogenic polypeptide, which in turn would induce antibodies and/or a T cell immune response to protect the mammal from cancers, including colon cancer, ovarian cancer, or breast cancer.

Naked CTSZ and/or CD24 nucleic acids, as described herein, can be administered as a vaccine via various routes, including, intramuscular, intravenous, intraperitoneal, intranasal (via mucosa), intradermal, subcutaneous (see, for example, Fynan et al. *Proc Natl Acad Sci USA* 90:1147811482 (1993); Molling K., *J Mol Med* 75:242–246 (1997)). For example, naked DNA, when injected intramuscularly, is taken up by cells, transcribed into mRNA, and expressed as protein. This protein is the actual vaccine, and it is produced by the vaccine recipient, which gives a higher chance of natural modifications and correct folding. It is presented to the immune system and induces both humoral and cellular immune responses (see, for example, Tang et al. *Nature* 356:152154 (1992); Molling K., *J Mol Med* 75:242–246 (1997)).

According to the invention, liposome encapsulated CTSZ and/or CD24 nucleic acids also can be administered. For example, clinical trials or other research studies with liposome encapsulated DNA in treating melanoma illustrated that the approach is effective in gene therapy (see, for example, Nabel, J. G., et al., "Direct gene transfer with DNA-liposome complexes in melanoma: Expression, biological activity and lack of toxicity in humans", *Proc. Nat. Acad. Sci. U.S.A.*, 90:11307–11311 (1993)).

Whether the immunogen is an CTSZ or a CD24 protein, a peptide derived therefrom or a nucleic acid sequence capable of directing host organism synthesis of CTSZ or CD24 protein or peptides derived therefrom, the immunogen may be administered for either a prophylactic or therapeutic purposes. Such prophylactic use may be appropriate for, for example, individuals with a genetic predisposition to a particular cancer. When provided prophylactically, the immunogen is provided in advance of the cancer or any symptom due to the cancer. The prophylactic administration of the immunogen serves to prevent or attenuate any subsequent onset of cancer. When provided therapeutically, the immunogen is provided at, or shortly after, the onset of cancer or any symptom associated with the cancer.

The present invention further relates to a vaccine for immunizing a mammal, for example, humans, against cancer comprising CTSZ or CD24 protein or an expression vector capable of directing host organism synthesis of CTSZ or CD24 protein in a pharmaceutically acceptable carrier.

In addition to use as vaccines and in immunotherapy the above compositions can be used to prepare antibodies to CTSZ or CD24 protein. To prepare antibodies, a host animal is immunized using the CTSZ or CD24 protein or peptides derived therefrom or aforementioned expression vectors capable of expressing CTSZ or CD24 protein or peptides derived therefrom. The host serum or plasma is collected following an appropriate time interval to provide a composition comprising antibodies reactive with the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other drugs.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas. Humanized antibodies (i.e., nonimmunogenic in a human) may be produced, for example, by replacing an immunogenic portion of a non-human antibody with a corresponding, but nonimmunogenic portion (i.e., chimeric antibodies). Such chimeric antibodies may contain the reactive or antigen binding portion of an antibody from one species and the Fe portion of an antibody (nonimmunogenic) from a different species. Examples of chimeric antibodies, include but are not limited to, non-human mammal-human chimeras, such as rodent-human chimeras, murine-human and rat-human chimeras (Cabilly et al., *Proc. Natl. Acad. Sci. USA*, 84:3439, 1987; Nishimura et al., *Cancer Res.*, 47:999, 1987; Wood et al., *Nature*, 314:446, 1985; Shaw et al., *J. Natl. Cancer Inst.*, 80:15553, 1988). General reviews of "humanized" chimeric antibodies are provided by Morrison S., *Science*, 229:1202, 1985 and by Oi et al., *BioTechniques*, 4:214, 1986.

Alternatively, anti-CTSZ and/or anti-CD24 antibodies can be induced by administering anti-idiotype antibodies as immunogen. Conveniently, a purified anti-CTSZ or anti-CD24 antibody preparation prepared as described above is used to induce anti-idiotype antibody in a host animal. The composition is administered to the host animal in a suitable diluent. Following administration, usually repeated administration, the host produces anti-idiotype antibody. To eliminate an immunogenic response to the Fc region, antibodies produced by the same species as the host animal can be used or the Fe region of the administered antibodies can be removed. Following induction of anti-idiotype antibody in the host animal, serum or plasma is removed to provide an antibody composition. The composition can be purified as described above for anti-CTSZ or anti-CD24 antibodies, or by affinity chromatography using anti-CTSZ or anti-CD24 antibodies bound to the affinity matrix. The anti-idiotype antibodies produced are similar in conformation to the authentic CTSZ or CD24 antigen and may be used to prepare vaccine rather than using an CTSZ or a CD24 protein.

To induce anti-CTSZ or anti-CD24 antibodies in an animal, the method of administering the CTSZ or CD24 antigen can be the same as used in the case of vaccination, for example, intramuscularly, intraperitoneally, subcutaneously or the like in an effective concentration in a physiologically suitable diluent with or without adjuvant. One or more booster injections may be desirable.

For both in vivo use of antibodies to CTSZ or CD24 proteins and anti-idiotype antibodies and for diagnostic use, it may be preferable to use monoclonal antibodies. Monoclonal anti-CTSZ or anti-CD24 antibodies, or anti-idiotype antibodies can be produced by methods known to those skilled in the art. (Goding, J. W. 1983. *Monoclonal Antibodies: Principles and Practice*, Pladermic Press, Inc., NY, N.Y., pp. 56–97). To produce a human-human hybridoma, a human lymphocyte donor is selected. A donor known to have the CTSZ or CD24 antigen may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides also can be used in the generation of human monoclonal antibodies.

H. Pharmaceutical Applications of Compounds:

The identified compounds that inhibit the expression, synthesis, and/or activity of the target gene, for example, CTSZ and/or CD24 can be administered to a patient at therapeutically effective doses to prevent, treat, or control a tumor or cancer. A therapeutically effective dose refers to an amount of the compound that is sufficient to result in a measurable reduction or elimination of cancer or its symptoms.

Toxicity and therapeutic efficacy of such compounds can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from the cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the method of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC).

Pharmaceutical compositions for use in the present invention can be formulated by standard techniques using one or more physiologically acceptable carriers or excipients. The compounds and their physiologically acceptable salts and solvates can be formulated and administered, for example, orally, intraorally, rectally, parenterally, epicutaneously, topically, transdermally, subcutaneously, intramuscularly, intranasally, sublingually, intradurally, intraocularly, intrarespiratorally, intravenously, intraperitoneally, intrathecal, mucosally, by oral inhalation, nasal inhalation, or rectal administration, for example.

For oral administration, the pharmaceutical compositions can take the form of tablets or capsules prepared by conventional means with pharmaceutically acceptable excipients, for example, binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. The tablets can be coated by methods well known in the art. Liquid preparations for oral administration can take the form of solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations also can contain buffer salts, flavoring, to coloring, and/or sweetening agents as appropriate. Preparations for oral administration can be suitably formulated to give controlled release of the active compound.

For administration by inhalation, the compounds are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use. The compounds also can be formulated in rectal compositions, for example, suppositories or retention enemas, for example, containing conventional suppository bases, for example, cocoa butter or other glycerides.

Furthermore, the compounds also can be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can for example comprise metal or plastic foil, for example, a blister pack. The pack or dispenser device can be accompanied by instructions for administration.

I. Administration of siRNA/shRNA/miRNA:

The invention includes methods of administering siRNA, shRNA, and miRNA, to a patient in need thereof, wherein the siRNA, shRNA, or miRNA molecule is delivered in the form of a naked oligonucleotide or via an expression vector as described herein.

The present invention provides methods of blocking the in vivo expression of CTSZ or CD24 gene by administering a naked DNA or a vector containing siRNA, shRNA, or miRNA as set forth herein (see, for example, Examples VII and VIII), which interacts with the target gene and causes post-transcriptional silencing of specific genes in cells, for example, mammalian cells (including human cells) and in the body, for example, mammalian bodies (including humans).

The invention also provides methods for the treatment of cells ex vivo by administering a naked DNA or a vector according to the invention.

In its in vivo or ex vivo therapeutic applications, it is appropriate to administer siRNA, shRNA, or miRNAs using a viral or retroviral vector, which enters the cell by transfection or infection. In particular, as a therapeutic product according to the invention, a vector can be a defective viral vector, such as an adenovirus, or a defective retroviral vector, such as a murine retrovirus.

The vector used to convey the gene construct according to the invention to its target can be a retroviral vector, which will transport the recombinant construct by a borrower capsid, and insert the genetic material into the DNA of the host cell.

Techniques that use vectors, in particular viral vectors (retroviruses, adenoviruses, adeno-associated viruses), to transport genetic material to target cells can be used to introduce genetic modifications into various somatic tissues, for example, colon, ovarian, or breast cells.

The use of retroviral vectors to transport genetic material necessitates, on the one hand, carrying out the genetic construction of the recombinant retrovirus, and on the other hand having a cell system available which provides for the function of encapsidation of the genetic material to be transported:

i. In a first stage, genetic engineering techniques enable the genome of a murine retrovirus, such as Moloney virus (murine retrovirus belonging to the murine leukemia virus group (Reddy et al., *Science,* 214:445–450 (1981)). The retroviral genome is cloned into a plasmid vector, from which all the viral sequences coding for the structural proteins (genes: Gag, Env) as well as the sequence coding for the enzymatic activities (gene: Pol) are then deleted. As a result, only the necessary sequences "in cis" for replication, transcription and integration are retained (sequences corresponding to the two LTR regions, encapsidation signal and primer binding signal). The deleted genetic sequences may be replaced by non-viral genes such as the gene for resistance to neomycin (selection antibiotic for eukaryotic cells) and by the gene to be transported by the retroviral vector, for example, CTSZ or CD24 siRNA as set forth herein.

ii. In a second stage, the plasmid construct thereby obtained is introduced by transfection into the encapsidation cells. These cells constitutively express the Gag, Pol and Env viral proteins, but the RNA coding for these proteins lacks the signals needed for its encapsidation. As a result, the RNA cannot be encapsidated to enable viral particles to be formed. Only the recombinant RNA emanating from the transfected retroviral construction is equipped with the encapsidation signal and is encapsidated. The retroviral particles produced by this system contain all the elements needed for the infection of the target cells (such as CD34+ cells) and for the permanent integration of the gene of interest into these cells, for example, CTSZ or CD24 siRNA as set forth herein. The absence of the Gag, Pol and Env genes prevents the system from continuing to propagate.

DNA viruses such as adenoviruses also can be suited to this approach although, in this case, maintenance of the DNA in the episomal state in the form of an autonomous replicon is the most likely situation.

Adenoviruses possess some advantageous properties. In particular, they have a fairly broad host range, are capable of infecting quiescent cells and do not integrate into the genome of the infected cell. For these reasons, adenoviruses have already been used for the transfer of genes in vivo. To this end, various vectors derived from adenoviruses have been prepared, incorporating different genes (beta-gal, OTC, alpha-1At, cytokines, etc.). To limit the risks of multiplication and the formation of infectious particles in vivo, the adenoviruses used are generally modified so as to render them incapable of replication in the infected cell. Thus, the adenoviruses used generally have the E1 (E1a and/or E1b) and possibly E3 regions deleted.

The defective recombinant adenoviruses according to the invention may be prepared by any technique known to persons skilled in the art (Levrero et al., Gene, 101:195 (1991), EP 185 573; Graham, EMBO J. 3:2917 (1984)). In particular, they may be prepared by homologous recombination between an adenovirus and a plasmid in a suitable cell line.

According to the present invention, an exogenous DNA sequence, for example, CTSZ or CD24 siRNA as set forth herein, is inserted into the genome of the defective recombinant adenovirus.

Pharmaceutical compositions comprising one or more viral vectors, such as defective recombinants as described above, may be formulated for the purpose of topical, oral, parenteral, intranasal, intravenous, intramuscular, subcutaneous, intraocular, and the like, administration. Preferably, these compositions contain vehicles which are pharmaceutically acceptable for an administrable formulation. These can be, in particular, isotonic, sterile saline solutions (of monosodium or disodium phosphate, sodium, potassium, calcium or magnesium chloride, and the like, or mixtures of such salts), or dry, in particular lyophilized, compositions which, on addition, as appropriate, of sterilized water or of physiological saline, enable particular injectable solutions to be made up.

The doses of defective recombinant virus used for the injection may be adapted in accordance with various parameters, and in particular in accordance with the mode of administration used, the pathology in question, the gene to be expressed or the desired duration of treatment. Generally speaking, the recombinant adenoviruses according to the invention may be formulated and administered in the form of doses of between $10^4$ and $10^{14}$ pfu/ml, and preferably $10^6$ to $10^{10}$ pfu/ml. The term pfu ("plaque forming unit") corresponds to the infectious power of a solution of virus, and is determined by infection of a suitable cell culture and measurement, generally after 48 hours, of the number of plaques of infected cells. The techniques of determination of the pfu titer of a viral solution are well documented in the literature.

The use of genetically modified viruses as a shuttle system for transporting the modified genetic material not only permits the genetic material to enter the recipient cell by the expedient of using a borrower viral capsid, but also allows a large number of cells to be treated simultaneously and over a short period of time, which permits therapeutic treatment applied to the whole body.

The invention is further described by the following examples, which do not limit the invention in any manner.

EXAMPLES

Example I

Amplification of the CTSZ Gene in Human Cancers

DNA microarray-based CGH was used to survey the genome for gene amplification, and discovered that the CTSZ gene is frequently amplified in tumor tissue and cell lines.

Genomic DNAs were isolated from colon cancer, breast cancer, or ovarian cancer samples. DNAs were analyzed, along with the same CTSZ TaqMan probe representing the target and a reference probe representing a normal non-amplified, single copy region in the genome, with a TaqMan 7700 Sequence Detector (Applied Biosystems) following the manufacturer's protocol.

CTSZ was found amplified in over 23% (9/28) of colon tumor, over 23% (10/42) of breast tumor and over 12% (3/24) of ovarian tumor samples tested (see Table 1).

TABLE 1

Amplification and overexpression of CTSZ in human tumors.

| Tumor type | Amplification* | | Tumor type | Overexpression* | |
|---|---|---|---|---|---|
| | Frequency | Maximum Fold | | Frequency | Maximum Fold |
| Colon, n = 38 | >23% (9/38) | 12x | Colon, n = 32 | >40% (13/32) | 52x |
| Breast, n = 42 | >23% (10/42) | 5x | Breast, n = 12 | >33% (4/12) | 10x |
| Ovary, n = 24 | >12% (3/24) | 3x | Ovary, n = 17 | >23% (4/17) | 10x |

*Amplification cutoff: 2.5x; Overexpression cutoff: 3x using β-actin as reference.

Only samples with the CTSZ gene copy number greater than or equal to 2.5-fold are deemed to have been amplified because of current instrumental detection limit. However, an increase in CTSZ gene copy number less than 2.5-fold can still be considered as an amplification of the gene, if detected.

Example II

Overexpression of the CTSZ Gene in Colon Cancer

Reverse transcriptase (RT)-directed quantitative PCR was performed using the TaqMan 7700 Sequence Detector (Applied Biosystems) to determine the CTSZ mRNA level in each sample. Human β-actin mRNA was used as control.

Total RNA was isolated from tumor samples using Trizol Reagent (Invitrogen) and treated with DNAase (Ambion) to eliminate genomic DNA. The reverse transcriptase reaction (at 48° C. for 30 min, for example) was coupled with quantitative PCR measurement of cDNA copy number in a one-tube format according to the manufacturer (Perkin Elmer/Applied Biosystems). CTSZ expression levels in the samples were normalized using human β-actin and overexpression fold was calculated by comparing CTSZ expression in tumor v. normal samples.

The nucleotide sequences of the CTSZ were used to design and make a suitable TaqMan probe set (see GenBank RECORD NM_001336) for CTSZ. The measurements of the mRNA level of each cancer cell line sample were normalized to the mRNA levels in respective normal sample.

The RT-TaqMan showed that CTSZ gene is overexpressed in colon, breast, and ovarian tumors. The overexpression of CTSZ was found in over 40% (13/32) of colon tumors, over 33% (4/12) in breast tumors, and over 23% (4/17) of ovarian tumors analyzed (see Table 1).

Example III

Physical Map of the Amplicon Containing the CTSZ Gene Locus

Cancer cell lines or primary tumors were examined for DNA copy number of genes and markers near CTSZ to map the boundaries of the amplified regions.

DNA was purified from tumor cell lines or primary tumors. The DNA copy number of each marker in each sample was directly measured using PCR and a fluorescence-labeled probe. The number of PCR cycles needed to cross a preset threshold, also known as Ct value, in the sample tumor DNA preparations and a series of normal human DNA preparations at various concentrations was determined for both the target probe and a known single-copy DNA probe using a TaqMan 7700 Sequence Detector (Applied Biosystems). The relative abundance of target sequence to the single-copy probe in each sample was then calculated by statistical analyses of the Ct values of the unknown samples and the standard curve was generated from the normal human DNA preparations at various concentrations.

To determine the DNA copy number for each of the genes, corresponding probes to each marker were designed using PrimerExpress 1.0 (Applied Biosystems) and synthesized by Operon Technologies. Subsequently, the target probe (representing the marker), a reference probe (representing a normal non-amplified, single copy region in the genome), and tumor genomic DNA (10 ng) were subjected to analysis by the TaqMan 7700 Sequence Detector (Applied Biosystems) following the manufacturer's protocol. The epicenter mapping around CTSZ gene was performed using amplified tumor samples. The CTSZ gene is indicated by an arrow. The genetic markers used include: GNAs1, TH1L, CTSZ, TUBB1, and C20ORF66. v87w, sk-mel-3, hs695t, luncl1, 87-505, 88-647, alab, bt20, mbl57, and mcf7 are tumor samples. The number of DNA copies for each sample was plotted against the corresponding marker in FIG. 1. The number of DNA copies for each sample is plotted on the Y-axis, and the X-axis corresponds to nucleotide position based on Human Genome Project working draft sequence (http://genome.ucsc.edu/goldenPath/aug2001Tracks.html). FIG. 1 shows epicenter mapping of 20q13 amplicon, which includes the CTSZ locus. A full-length CTSZ gene was present at the epicenter.

Example IV

Amplification of the CD24 Gene in Human Cancers

DNA microarray-based CGH was used to survey the genome for gene amplification, and discovered that the CD24 gene is frequently amplified in tumor tissue and cell lines.

The genomic DNAs were isolated from breast cancer cell lines, and breast tumor samples. DNAs were analyzed, along with the same CD24 TaqMan probe representing the target and a reference probe representing a normal non-amplified, single copy region in the genome, with a TaqMan 7700 Sequence Detector (Applied Biosystems) following the manufacturer's protocol.

CD24 was found amplified in over 26% (9/34) of breast tumor samples tested. The RT-TaqMan showed that CD24 is amplified up to 13 fold among the breast tumor samples tested (see Table 2).

Only samples with the CD24 gene copy number greater than or equal to 2.5-fold are deemed to have been amplified because of current instrumental detection limit. However, an increase in CD24 gene copy number less than 2.5-fold can still be considered as an amplification of the gene, if detected.

TABLE 2

Amplification and overexpression of CD24 in breast tumors.

| Tumor sample | Fold amplification | Fold of overexpression |
| --- | --- | --- |
| 11168 | 13 | 7.2 |
| 8870 | 10 | 6.9 |
| 7952 | 8 | 8.6 |
| 8830 | 4.5 | 3.2 |
| 11601 | 3 | 2.9 |

Example V

Overexpression of the CD24 Gene in Human Cancers

Reverse transcriptase (RT)-directed quantitative PCR was performed using the TaqMan 7700 Sequence Detector (Applied Biosystems) to determine the CD24 mRNA level in each sample. Human β-actin mRNA was used as control.

Total RNA was isolated from tumor samples using Trizol Reagent (Invitrogen) and treated with DNAase (Ambion) to eliminate genomic DNA. The reverse transcriptase reaction (at 48° C. for 30 min, for example) was coupled with quantitative PCR measurement of cDNA copy number in a one-tube format according to the manufacturer (Perkin Elmer/Applied Biosystems). CD24 expression levels in the samples were normalized using human β-actin and overexpression fold was calculated by comparing CD24 expression in tumor v. normal samples.

The nucleotide sequences of the CD24 were used to design and make a suitable TaqMan probe set (see GenBank RECORD NM_013230) for CD24. The measurements of the mRNA level of each cancer cell line sample were normalized to the mRNA levels in respective normal sample. The RT-TaqMan showed that CD24 is overexpressed up to 8.6 fold among the breast tumor samples tested (see Table 2).

Among the primary breast tumor samples tested, overexpression of CD24 correlated with poor prognosis (see Table 3).

Example VI

Physical Map of the Amplicon Containing the CD24 Gene Locus

Cancer cell lines or primary tumors were examined for DNA copy number of genes and markers near CD24 to map the boundaries of the amplified regions.

DNA was purified from tumor cell lines or primary tumors. The DNA copy number of each marker in each sample was directly measured using PCR and a fluorescence-labeled probe. The number of PCR cycles needed to cross a preset threshold, also known as Ct value, in the sample tumor DNA preparations and a series of normal human DNA preparations at various concentrations was determined for both the target probe and a known single-copy DNA probe using a TaqMan 7700 Sequence Detector (Applied Biosystems). The relative abundance of target sequence to the single-copy probe in each sample was then calculated by statistical analyses of the Ct values of the unknown samples and the standard curve was generated from the normal human DNA preparations at various concentrations.

To determine the DNA copy number for each of the genes, corresponding probes to each marker were designed using PrimerExpress 1.0 (Applied Biosystems) and synthesized by Operon Technologies. Subsequently, the target probe (representing the marker), a reference probe (representing a normal non-amplified, single copy region in the genome), and tumor genomic DNA (10 ng) were subjected to analysis by the TaqMan 7700 Sequence Detector (Applied Biosystems) following the manufacturer's protocol. The epicenter mapping around CD24 gene was performed using amplified tumor samples.

Example VII

Small Interfering RNA (siRNA)

Sense and antisense siRNAs duplexes are made based upon targeted region of a DNA sequence of CTSZ or CD24, as disclosed herein (see, for example, SEQ ID NO:1, SEQ ID NO:3, SEQ ID NO:4, SEQ ID NO:6, or a fragment thereof), are typically less than 100 base pairs ("bps") in length and constituency and preferably are about 30 bps or shorter, and are made by approaches known in the art, including the use of complementary DNA strands or synthetic approaches. SiRNA derivatives employing polynucleic acid modification techniques, such as peptide nucleic acids, also can be employed according to the invention. The siRNAs are capable of causing interference and can cause post-transcriptional silencing of specific genes in cells, for example, mammalian cells (including human cells) and in the body, for example, mammalian bodies (including humans). Exemplary siRNAs according to the invention have up to 29 bps, 25 bps, 22 bps, 21 bps, 20 bps, 15 bps, 10 bps, 5 bps or any integer thereabout or therebetween.

A targeted region is selected from the DNA sequence (for example, SEQ ID NO:1, SEQ ID NO:3, SEQ ID NO:4, SEQ ID NO:6, or a fragment thereof). Various strategies are followed in selecting target regions and designing siRNA oligos, for example, 5' or 3' UTRs and regions nearby the

TABLE 3

Overexpression of CD24 correlates with poor prognosis.

| Primary breast tumor samples | Genomic amplification* | Overexpression* | Status of patient |
|---|---|---|---|
| 7952 | 7.9 | 8.2 | died of disease |
| 8830 | 4.5 | 4.2 | died of disease |
| 8870 | 7.3 | 6.7 | died of disease |
| 8909 | 4.9 | 7.4 | died of disease |
| 8930 | 12.5 | 15.3 | died of disease |
| 9681 | 45.1 | 5.5 | died of disease |
| 9794 | 12.6 | 3.7 | died of disease |
| 10058 | 2.9 | 5.8 | died of disease |
| 10151 | 2.6 | 3.7 | died of disease |
| 10460 | 11.6 | 3.3 | died of disease |
| 10480 | 4.3 | 4.1 | died of disease |
| 10614 | 2.5 | 3.1 | died of disease |
| 11168 | 4.1 | 7.2 | died of disease |
| 11238 | 7.6 | 7.9 | died of disease |
| 8752 | 1.3 | 5.8 | lost to fu |
| 8785 | 1.1 | 3.5 | died unknown cause |
| 8817 | 1.1 | 12.3 | died of disease |
| 9109 | 0.9 | 6.6 | died of disease |
| 9110 | 1.1 | 3.1 | died unknown cause |

*Relative fold of genomic amplification and mRNA expression were measured by Taqman and RT-TaqMan.

DNA copy number was determined using real time quantitative PCR (QPCR). Human genomic DNA clones used include: AGP5L, FJ10989, AA95394, CD24.2, AL591516, and AL121957. The genetic markers used include: 7952, 8830, 8870, and 11168. The number of DNA copies for each sample was plotted against the corresponding marker in FIG. 2. The number of DNA copies for each sample is plotted on the Y-axis, and the X-axis corresponds to nucleotide position based on Human Genome Project working draft sequence (http://genome.ucsc.edu/goldenPath/aug2001Tracks.html). FIG. 2 shows epicenter mapping of 6q21 amplicon, which includes the CD24 locus. A full-length CD24 gene was present at the epicenter.

start codon should be avoided, as these may be richer in regulatory protein binding sites. Designed sequences preferably include AA-(N27 or less nucleotides)-TT and with about 30% to 70% G/C-content. If no suitable sequences are found, the fragment size is extended to sequences AA(N29 nucleotides). The sequence of the sense siRNA corresponds to, for example, (N27 nucleotides)-TT or N29 nucleotides, respectively. In the latter case, the 3' end of the sense siRNA is converted to TT. The rationale for this sequence conversion is to generate a symmetric duplex with respect to the sequence composition of the sense and antisense 3' overhangs. It is believed that symmetric 3' overhangs help to ensure that the small interfering ribonucleoprotein particles (siRNPs) are formed with approximately equal ratios of sense and antisense target RNA-cleaving siRNPs (Elbashir et al. *Genes & Dev.* 15:188–200, 2001).

CTSZ siRNA: Sense or antisense siRNAs are designed based upon targeted regions of a DNA sequence, as disclosed herein (see, for example, SEQ ID NO:3, GenBank Accession No. NM_001336), and include fragments having up to 29 bps, 25 bps, 22 bps, 21 bps, 20 bps, 15 bps, 10 bps, 5 bps or any integer thereabout or therebetween. For example, 29 bps siRNA include:

Targeted region (base position numbers 9–37, SEQ ID NO:7)

5'-GCGCGGGCCAGGGTGGCGGCCGCTTCTGC-3',
the corresponding sense siRNA (SEQ ID NO:8), and
5'-GCGCGGGCCAGGGUGGCGGCCGCUUCUGC-3';

Targeted region (base position numbers 14–42, SEQ ID NO:9)

5'-GGCCAGGGTGGCGGCCGCTTCTGCTGCTC-3', and
the corresponding sense siRNA (SEQ ID NO:10)
5'-GGCCAGGGUGGCGGCCGCUUCUGCUGCUC-3';

Targeted region (base position numbers 21–49, SEQ ID NO:11)

5'-GTGGCGGCCGCTTCTGCTGCTCGTGCTGC-3', and
the corresponding sense siRNA (SEQ ID NO:12)
5'-GUGGCGGCCGCUUCUGCUGCUCGUGCUGC-3';
and continuing in this progression to the end of CTSZ coding sequence, for example, Targeted region (base position numbers 844–872, SEQ ID NO:13)

5'-GATGGGAAGGGCGCCAGATACAACCTTGC-3', and
the corresponding sense siRNA (SEQ ID NO:14)
5'-GAUGGGAAGGGCGCCAGAUACAACCUUGC-3';
and so on as set forth herein.

A set of siRNAs/shRNAs are designed based on CTSZ-coding sequence (see, for example, SEQ ID NO:3, GenBank Accession No. NM_001336).

Example VIII

A PCR-Based Strategy for Cloning siRNA/shRNA Sequences

Oligos are designed based on a set criteria, for example, 29 bps 'sense' sequences (for example, a target region of base position numbers 9–37 of the CTSZ-coding sequence) containing a 'C' at the 3' end are selected from the CTSZ-coding sequence. A termination sequence (for example, AAAAAA, SEQ ID NO:15), the corresponding antisense sequence (for example, the antisense sequence of the base position numbers 9–37 of the CTSZ-coding sequence), a loop (for example, GAAGCTTG, SEQ ID NO:16), and a reverse primer (for example, U6 reverse primer, GGTGTTTCGTCCTTTCCACAA, SEQ ID NO:17) are subsequently added to the 29 bps sense strands to construct PCR primers (Paddison et al., Genes & Dev. 16: 948–958, 2002). Of course, other sense and anti-sense sequences can be selected from a target molecule to develop siRNAs for that molecule.

Several steps are followed in generating hairpin primers. First, a 29 nt "sense" sequence containing a "C" is selected. Second, the actual hairpin is constructed in a 5'-3' orientation with respect to the intended transcript. Third, a few stem pairings are changed to G-U by altering the sense strand sequence. G-U base pairing seems to be beneficial for stability of short hairpins in bacteria and does not interfere with silencing. Finally, the hairpin construct is converted to its "reverse complement" and combined with 21 nt human U6 promoter.

Some base pairings are changed to G-U by altering sense sequence. The final hairpin is converted to its reverse complement. Examples of the hairpin sequences are shown in the following section.

PCR and Cloning: A pGEM1 plasmid (Promega) containing the human U6 locus (G. Hannon, CSHL) is used as the template for the PCR reaction. This vector contains about 500 bp of upstream U6 promoter sequence. Since an SP6 sequence flanks the upstream portion of the U6 promoter, an SP6 oligo is used as the universal primer in U6-hairpin PCR reactions. The PCR product is about 600 bp in length. T-A and directional topoisomerase-mediated cloning kits (Invitrogen, Inc. Catalog No. K2040-10, K2400-20) are used according to the manufacturer's instruction.

To obtain stable siRNAs/shRNAs, some nucleotide bases are modified, therefore, the designed oligo sequences may not match the actual coding sequences.

Examples of oligos designed and the targeted base position numbers of the 29 nt sense sequence of the CTSZ-coding region (see, for example, SEQ ID NO:3, GenBank Accession No. NM_001336) are shown below:

SEQ ID NO:18: Primer containing a target region (starting base position number 9 of the CTSZ-coding sequence):

AAAAAAGCAGAAGCGGCCGCCACCCTGGCCCGCGCCAAGCTTCGCGCGGG
CCAGGGTGGCGGCCGCTTCTGCGGTGTTTCGTCCTTTCCACAA-3',
and the cDNA targeted CTSZ-coding region is (coding region base position numbers 9–37, SEQ ID NO:7) 5'-GCGCGGGCCAGGGTGGCGGCCGCTTCTGC-3';

SEQ ID NO:19: Primer containing a target region (starting base position number 21 of the CTSZ-coding sequence):

AAAAAAGCAGCACGAGCAGCAGAAGCGGCCGCCACCAAGCTTCGTGGCGG
CCGCTTCTGCTGCTCGTGCTGCGGTGTTTCGTCCTTTCCACAA-3',
and the cDNA targeted CTSZ-coding region is (coding region base position numbers 21–49, SEQ ID NO:11) 5'-GTGGCGGCCGCTTCTGCTGCTCGTGCTGC-3'; and SEQ ID NO:20: Primer containing a target region (starting base position number 844 of the CTSZ-coding sequence):

AAAAAAGCAAGGTTGTATCTGGCGCCCTTCCCATCCAAGCTTCGATGGGA
AGGGCGCCAGATACAACCTTGCGGTGTTTCGTCCTTTCCACAA-3',
and the cDNA targeted CTSZ-coding region is (coding region base position numbers 844–872, SEQ ID NO:13) 5'-GATGGGAAGGGCGCCAGATACAACCTTGC-3'.

CD24 siRNA: Sense or antisense siRNAs are designed based upon targeted regions of a DNA sequence, as disclosed herein (see, for example, SEQ ID NO:6, GenBank Accession No. NM_013230), and include fragments having up to 29 bps, 25 bps, 22 bps, 21 bps, 20 bps, 15 bps, 10 bps, 5 bps or any integer thereabout or therebetween. For example, 29 bps siRNA include:

Targeted region (base position numbers 15–43, SEQ ID NO:21)

5'-GGTGGCCAGGCTGGGGCTGGGGCTGCTGC-3', the corresponding sense siRNA (SEQ ID NO:22), and

5'-GGUGGCCAGGCUGGGGCUGGGGCUGCUGC-3';

Targeted region (base position numbers 18–46, SEQ ID NO:23)

5'-GGCCAGGCTGGGGCTGGGGCTGCTGCTGC-3', and the corresponding sense siRNA (SEQ ID NO:24)

5'-GGCCAGGCUGGGGCUGGGGCUGCUGCUGC-3';

Targeted region (base position numbers 34–62, SEQ ID NO:25)

5'-GCTGGGGCTGGGGCTGCTGCTGCTGGCAC-3', and the corresponding sense siRNA (SEQ ID NO:26)

5'-GCUGGGGCUGGGGCUGCUGCUGCUGGCAC-3';
and continuing in this progression to the end of CD24 coding sequence, for example, Targeted region (base position numbers 211–239, SEQ ID NO:27)

5'-GTCTCACTCTCTCTTCTGCATCTCTACTC-3', and the corresponding sense siRNA (SEQ ID NO:28)

5'-GUCUCACUCUCUCUUCUGCAUCUCUACUC-3';
and so on as set forth herein.

A set of siRNAs/shRNAs are designed based on CD24-coding sequence (see, for example, SEQ ID NO:6, GenBank Accession No. NM_013230).

As described herein for CTSZ and CD24, oligos also are designed based on a set criteria. A 29 bps 'sense' sequence (for example, a target region starting at base position number 3 of the CD24-coding sequence) containing a 'C' at the 3' end are selected from the CD24-coding sequence. A termination sequence (for example, AAAAAA, SEQ ID NO:15), the corresponding antisense sequence (for example, the antisense sequence of the base position numbers 15–43 of the CD24-coding sequence), a loop (for example, GAAGCTTG, SEQ ID NO:16), and a reverse primer (for example, U6 reverse primer, GGTGTTTCGTCCTTTCCACAA, SEQ ID NO:17) are subsequently added to the 29 bps sense strands to construct CD24 PCR primers (see, for example, the model shRNA structure as shown above) (see, for example, Paddison et al., *Genes & Dev.* 16: 948–958, 2002). Of course, other sense and anti-sense sequences can be selected from a target molecule to develop siRNAs for that molecule.

Examples of oligos designed and the targeted base position numbers of the 29 nt sense sequence of the CD24-coding sequence (see, for example, SEQ ID NO:6, GenBank Accession No. NM_013230) are shown below:

SEQ ID NO:29: Primer containing a target region (starting base position number 15 of the CD24-coding sequence):

AAAAAAGCAGCAGCCCCAGCCCCAGCCTGGCCACCCAAGCTTCGGTGGCC
AGGCTGGGGCTGGGGCTGCTGCGGTGTTTCGTCCTTTCCACAA-3',
and the cDNA targeted CD24-coding region is (coding region base position numbers 15–43, SEQ ID NO:21) 5'-GGTGGCCAGGCTGGGGCTGGGGCTGCTGC-3';

SEQ ID NO:30: Primer containing a target region (starting base position number 18 of the CD24-coding sequence):

AAAAAAGCAGCAGCAGCCCCAGCCCCAGCCTGGCCCAAGCTTCGGCCAGG
CTGGGGCTGGGGCTGCTGCTGCGGTGTTTCGTCCTTTCCACAA-3',
and the cDNA targeted CD24-coding region is (coding region base position numbers 18–46, SEQ ID NO:23) 5'-GGCCAGGCTGGGGCTGGGGCTGCTGCTGC-3';

SEQ ID NO:31: Primer containing a target region (starting base position number 34 of the CD24-coding sequence):

AAAAAAGTGCCAGCAGCAGCAGCCCCAGCCCCAGCCAAGCTTCGCTGGGG
CTGGGGCTGCTGCTGCTGGCACGGTGTTTCGTCCTTTCCACAA-3',
and the cDNA targeted CD24-coding region is (coding region base position numbers 34–62, SEQ ID NO:25) 5'-GCTGGGCCTGGGGCTGCTGCTGCTGGCAC-3'; and SEQ ID NO:32: Primer containing a target region (starting base position number 211 of the CD24-coding sequence):

AAAAAAGAGTAGAGATGCAGAAGAGAGAGTGAGACCAAGCTTCCTCTCAC
TCTCTCTTCTGCATCTCTACTCGGTGTTTCGTCCTTTCCACAA-3',
and the cDNA targeted CD24-coding region is (coding region base position numbers 211–239, SEQ ID NO:27) 5'-GTCTCACTCTCTCTTCTGCATCTCTACTC-3'.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

SEQ ID NO:1. Human CTSZ Sequence (1501 bps): The GenBank Accession No. for *Homo sapiens* cathepsin Z (CTSZ) is NM_001336:

```
  1 GGGGTCGGCC GGGTGCTAGG CCGGGGCCGA GGCCGAGGCC GGGGCGGGAT CCAGAGCGGG

61 AGCCGGCCCG GGATCTGGGA CTCGGAGCGG GATCCGGAGC GGGACCCAGG AGCCGGCGCG

121 GGGCCATGGC GAGGCGCGGG CCAGGGTGGC GGCCGCTTCT GCTGCTCGTG CTGCTGGCGG

181 GCGCGGCGCA GGGCGGCCTC TACTTCCGCC GGGGACAGAC CTGCTACCGG CCTCTGCGGG

241 GGGACGGGCT GGCTCCGCTG GGGCGCAGCA CATACCCCCG GCCTCATGAG TACCTGTCCC
```

-continued

```
 301 CAGCGGATCT GCCCAAGAGC TGGGACTGGC GCAATGTGGA TGGTGTCAAC TATGCCAGCA
 361 TCACCCGGAA CCAGCACATC CCCCAATACT GCGGCTCCTG CTGGGCCCAC GCCAGCACCA
 421 GCGCTATGGC GGATCGGATC AACATCAAGA GGAAGGGAGC GTGGCCCTCC ACCCTCCTGT
 481 CCGTGCAGAA CGTCATCGAC TGCGGTAACG CTGGCTCCTG TGAAGGGGGT AATGACCTGT
 541 CCGTGTGGGA CTACGCCCAC CAGCACGGCA TCCCTGACGA GACCTGCAAC AACTACCAGG
 601 CCAAGGACCA GGAGTGTGAC AAGTTTAACC AATGTGGGAC ATGCAATGAA TTCAAAGAGT
 661 GCCACGCCAT CCGGAACTAC ACCCTCTGGA GGGTGGGAGA CTACGGCTCC CTCTCTGGGA
 721 GGGAGAAGAT GATGGCAGAA ATCTACGCAA ATGGTCCCAT CAGCTGTGGA ATAATGGCAA
 781 CAGAAAGACT GGCTAACTAC ACCGGAGGCA TCTATGCCGA ATACCAGGAC ACCACATATA
 841 TAAACCATGT CGTTTCCGTG GCTGGGTGGG GCATCAGTGA TGGGACTGAG TACTGGATTG
 901 TCCGGAATTC ATGGGGTGAA CCATGGGGCG AGAGAGGCTG CCTGAGGATC GTGACCAGCA
 961 CCTATAAGGA TGGGAAGGGC GCCAGATACA ACCTTGCCAT CGAGGAGCAC TGTACATTTG
1021 GGGACCCCAT CGTTTAAGGC CATGTCACTA GAAGCGCAGT TTAAGAAAAG CATGGTGAC
1081 CCATGACCAG AGGGGATCCT ATGGTTATGT GTGCCAGGCT GGCTGGCAGG AACTGGGGTG
1141 GCTATCAATA TTGGATGGCG AGGACAGCGT GGTACTGGCT GCGAGTGTTC CTGAGAGTTG
1201 AAAGTGGGAT GACTTATGAC ACTTGCACAG CATGGCTCTG CCTCACAATG ATGCAGTCAG
1261 CCACCTGGTG AAGAAGTGAC CTGCAACACA GGAAACGATG GGACCTCAGT CTTCTTCAGC
1321 AGAGGACTTG ATATTTTGTA TTTGGCAACT GTGGGCAATA ATATGGCATT TAAGAGGTGA
1381 AAGAGTTCAG ACTTATCACC ATTCTTATGT CACTTTAGAA TCAAGGGTGG GGGAGGGAGG
1441 GAGGGAGTTG GCAGTTTCAA ATCGCCCAAG TGATGAATAA AGTATCTGGC TCTGCACGAG
1501 A
```

SEQ ID NO:2. Human CTSZ polypeptide sequence (303 amino acids): The protein_id number is NP_001327.2:

```
NH2- MARRGPGWEPLLLLVLLAGAAQGGLYFRRGQTCYRPLRGDGLAP
LGRSTYPRPHEYLSPADLPKSWDWRNVDGVNYASITRNQHIPQYCGSCWAHASTSAMA
DRINIKEKGAWPSTLLSVQNVIDCGNAGSCEGGNDLSVWDYAHQHGIPDETCNNYQAK
DQECDKFNQCGTCNEFKECHAIRNYTLWRVGDYGSLSGREKMMAEIYANGPISCGIMA
TERLANYTGGIYAEYQDTTYINHVVSVAGWGISDGTEYWIVRNSWGEPWGERGWLRIV
TSTYKDGKGARYNLAIEEHCTFGDPIV -COOH
```

SEQ ID NO:3. *Homo sapiens* CTSZ coding sequence (912 bps). The GenBank Accession No. for human CTSZ is NM_001336.

```
  1 ATGGCGAGGC GCGGGCCAGG GTGGCGGCCG CTTCTGCTGC TCGTGCTGCT GGCGGGCGCG
 61 GCGCAGGGCG GCCTCTACTT CCGCCGGGGA CAGACCTGCT ACCGGCCTCT GCGGGGGGAC
121 GGCCTGGCTC CGCTGGGCCG CAGCACATAC CCCCGGCCTC ATGAGTACCT GTCCCCAGCG
181 GATCTGCCCA AGAGCTGGGA CTGGCGCAAT GTGGATGGTG TCAACTATGC CAGCATCACC
241 CGGAACCAGC ACATCCCCCA ATACTGCGGC TCCTGCTGGG CCCACGCCAG CACCAGCGCT
301 ATGGCGGATC GGATCAACAT CAAGAGGAAG GGAGCGTGGC CCTCCACCCT CCTGTCCGTG
```

-continued

```
361 CAGAACGTCA TCGACTGCGG TAACGCTGGC TCCTGTGAAG GGGGTAATGA CCTGTCCGTG

421 TGGGACTACG CCCACCAGCA CGGCATCCCT GACGAGACCT GCAACAACTA CCAGGCCAAG

481 GACCAGGAGT GTGACAAGTT TAACCAATGT GGGACATGCA ATGAATTCAA AGAGTGCCAC

541 GCCATCCGGA ACTACACCCT CTGGAGGGTG GGAGACTACG GCTCCCTCTC TGGGAGGGAG

601 AAGATGATGG CAGAAATCTA CGCAAATGGT CCCATCAGCT GTGGAATAAT GGCAACAGAA

661 AGACTGGCTA ACTACACCGG AGGCATCTAT GCCGAATACC AGGACACCAC ATATATAAAC

721 CATGTCGTTT CCGTGGCTGG GTGGGGCATC AGTGATGGGA CTGAGTACTG GATTGTCCGG

781 AATTCATGGG GTGAACCATG GGGCGAGAGA GGCTGGCTGA GGATCGTGAC CAGCACCTAT

841 AAGGATGGGA AGGGCGCCAG ATACAACCTT GCCATCGAGG AGCACTGTAC ATTTGGGGAC

901 CCCATCGTTT AA
```

SEQ ID NO:4. *Homo sapiens* CD24 sequence (2116 bps). The GenBank Accession No. for human CD24 is NM_013230.

```
   1 CGGTTCTCCA AGCACCCAGC ATCCTGCTAG ACGCGCCGCG CACCGACGGA GGGGACATGG

61 GCAGAGCAAT GGTGGCCAGG CTGGGGCTGG GGCTGCTGCT GCTGGCACTG CTCCTACCCA

121 CGCAGATTTA TTCCAGTGAA ACAACAACTG GAACTTCAAG TAACTCCTCC CACAGTACTT

181 CCAACTCTGC GTTGGCCCCA AATCCAACTA ATGCCACCAC CAAGGCGGCT GGTGGTGCCC

241 TGCAGTCAAC AGCCAGTCTC TTCGTGGTCT CACTCTCTCT TCTGCATCTC TACTCTTAAG

301 AGACTCAGGC CAAGAAACGT CTTCTAAATT TCCCCATCTT CTAAACCCAA TCCAAATGGC

361 GTCTGGAAGT CCAATGTGGC AAGGAAAAAC AGGTCTTCAT CGAATCTACT AATTCCACAC

421 CTTTTATTGA CACAGAAAAT GTTGAGAATC CCAAATTTGA TTGATTTGAA GAACATGTGA

481 GAGGTTTGAC TAGATGATGA ATGCCAATAT TAAATCTGCT GGAGTTTCAT GTACAAGATG

541 AAGGAGAGGC AACATCCAAA ATAGTTAAGA CATGATTTCC TTGAATGTGG CTTGAGAAAT

601 ATGGACACTT AATACTACCT TGAAAATAAG AATAGAAATA AAGGATGGGA TTGTGGAATG

661 GAGATTCAGT TTTCATTGGT TCATTAATTC TATAAGGCCA TAAAACAGGT AATATAAAAA

721 GCTTCCATCG ATCTATTTAT ATGTACATGA GAAGGAATCC CCAGGTGTTA CTGTAATTCC

781 TCAACGTATT GTTTCGACGG CACTAATTTA ATGCCGATAT ACTCTAGATG AATGTTTACA

841 TTGTTGAGCT ATTGCTGTTC TCTTGGGAAC TGAACTCACT TTCCTCCTGA GGCTTTGGAT

901 TTGACATTGC ATTTGACCTT TTAGGTAGTA ATTGACATGT GCCAGGGCAA TGATGAATGA

961 GAATCTACCC CAGATCCAAG CATCCTGAGC AACTCTTGAT TATCCATATT GAGTCAAATG

1021 GTAGGCATTT CCTATCACCT GTTTCCATTC AACAAGAGCA CTACATTCTT TTAGCTAAAC

1081 GGATTCCAAA GAGTAGAATT GCATTGACCA CGACTAATTT CAAAATGCTT TTTATTATTA

1141 TTATTTTTTA GACAGTCTCA CTTTGTCGCC CAGGCCGGAG TGCAGTGGTG CGATCTCAGA

1201 TCAGTGTACC ATTTGCCTCC CGGGCTCAAG CGATTCTCCT GCCTCAGCCT CCCAAGTAGC

1261 TGGGATTACA GGCACCTGCC ACCATGCCCG GCTAATTTTT GTAATTTTAG TAGAGACAGG

1321 GTTTCACCAT GTTGCCCAGC CTGGTTTAGA ACTCCTGACC TCAGGTGATC CACCCGCCTC

1381 GGCCTCCCAA AGTGCTGGGA TTACAGGCTT GAGCCCCGC GCCCAGCCAT CAAAATGCTT

1441 TTTATTTCTG CATATGTTTG AATACTTTTT ACAATTTAAA AAAATGATCT GTTTTGAAGG

1501 CAAAATTGCA AATCTTGAAA TTAAGAAGGC AAAATGTAAA GGAGTCAAAC TATAAATCAA

1561 GTATTTGGGA AGTGAAGACT GGAAGCTAAT TTGCATAAAT TCACAAACTT TTATACTCTT
```

-continued

```
1621 TCTGTATATA CATTTTTTTT CTTTAAAAAA CAACTATGGA TCAGAATAGC AACATTTAGA

1681 ACACTTTTTG TTATCAGTCA ATATTTTTAG ATAGTTAGAA CCTGGTCCTA AGCCTAAAAG

1741 TGGGCTTGAT TCTGCAGTAA ATCTTTTACA ACTGCCTCGA CACACATAAA CCTTTTTAAA

1801 AATAGACACT CCCCGAAGTC TTTTGTTTGT ATGGTCACAC ACTGATGCTT AGATGTTCCA

1861 GTAATCTAAT ATGGCCACAG TAGTCTTGAT GACCAAAGTC CTTTTTTTCC ATCTTTAGAA

1921 AACTACATGG GAACAAACAG ATCGAACAGT TTTGAAGCTA CTGTGTGTGT GAATGAACAC

1981 TCTTGCTTTA TTCCAGAATC CTGTACATCT ATTTTGGATT GTATATTGTG GTTGTGTATT

2041 TACGCTTTGA TTCATAGTAA CTTCTTATGG AATTGATTTG CATTGAACGA CAAACTGTAA

2101 ATAAAAAGAA ACGGTG
```

SEQ ID NO:5. Human CD24 polypeptide sequence (80 amino acids). The protein_id number is NP_037362.1.

NH$_2$-

MGRAMVARLGLGLLLLALLLPTQIYSSETTTGTSSNSSQSTSNSGLAPNPTNATTKAAGGALQSTASLFV

VSLSLLHLYS -COOH

SEQ ID NO:6. *Homo sapiens* CD24 coding sequence (243 bps). The GenBank Accession No. for human CD24 is NM_013230.

```
  1 ATGGGCAGAG CAATGGTGGC CAGGCTGGGG CTGGGGCTGC TGCTGCTGGC ACTGCTCCTA

61 CCCACGCAGA TTTATTCCAG TGAAACAACA ACTGGAACTT CAAGTAACTC CTCCCAGAGT

121 ACTTCCAACT CTGGGTTGGC CCCAAATCCA ACTAATGCCA CCACCAAGGC GGCTGGTGGT

181 GCCCTGCAGT CAACAGCCAG TCTCTTCGTG GTCTCACTCT CTCTTCTGCA TCTCTACTCT

241 TAA
```

We claim:

1. A method for diagnosing a cancer in a human, comprising:
   a) determining Cathepsin Z(CTSZ) gene copy number in a test biological subject from a region of the human that is suspected to be precancerous or cancerous, thereby generating data for a test gene copy number; and
   b) comparing the data for the test gene copy number to data for a control gene copy number, wherein an amplification of the gene in the test biological subject relative to the control indicates the presence of a precancerous lesion or a cancer in the human.

2. The method according to claim 1, wherein the cancer is a colon cancer, an ovarian cancer or a breast cancer.

3. The method according to claim 1, wherein at least one of the data for the test gene copy number and the data for the control gene copy number is stored in an electronic or a paper format.

4. The method according to claim 1, wherein the test gene copy number is determined by a hybridization- and/or an amplification-based assay.

5. The method according to claim 1, wherein the test gene copy number is determined by ligase chain reaction (LCR).

6. The method according to claim 1, wherein the test gene copy number is determined by polymerase chain reaction (PCR).

7. The method according to claim 1, wherein the test gene copy number is determined by real-time quantitative RT-PCR.

8. The method according to claim 1, wherein the test gene copy number is determined by fluorescence in situ hybridization (FISH).

9. The method according to claim 1, wherein the test gene copy number is determined by comparative genomic hybridization (CGH).

10. The method according to claim 1, wherein the test gene copy number is determined by microarray-based CGH.

* * * * *

SEQUENCE LISTING

<160> NUMBER OF SEQ ID NOS: 32

<210> SEQ ID NO 1
<211> LENGTH: 1501
<212> TYPE: DNA
<213> ORGANISM: Homo sapiens

<400> SEQUENCE: 1

```
ggggtcggcc gggtgctagg ccggggccga ggccgaggcc ggggcgggat ccagagcggg      60
agccggcgcg ggatctggga ctcggagcgg gatccggagc gggacccagg agccggcgcg     120
gggccatggc gaggcgcggg ccaggtggc ggccgcttct gctgctcgtg ctgctggcgg     180
gcgcggcgca gggcggcctc tacttccgcc ggggacagac ctgctaccgg cctctgcggg     240
gggacgggct ggctccgctg gggcgcagca cataccccg gcctcatgag tacctgtccc     300
cagcggatct gcccaagagc tgggactggc gcaatgtgga tggtgtcaac tatgccagca     360
tcacccggaa ccagcacatc ccccaatact gcggctcctg ctgggcccac gccagcacca     420
gcgctatggc ggatcggatc aacatcaaga ggaagggagc gtggcctcc accctcctgt      480
```

```
ccgtgcagaa cgtcatcgac tgcggtaacg ctggctcctg tgaagggggt aatgacctgt    540
ccgtgtggga ctacgcccac cagcacggca tccctgacga gacctgcaac aactaccagg    600
ccaaggacca ggagtgtgac aagtttaacc aatgtgggac atgcaatgaa ttcaaagagt    660
gccacgccat ccggaactac accctctgga gggtgggaga ctacggctcc ctctctggga    720
gggagaagat gatggcagaa atctacgcaa atggtcccat cagctgtgga ataatggcaa    780
cagaaagact ggctaactac accggaggca tctatgccga ataccaggac accacatata    840
taaaccatgt cgtttccgtg gctgggtggg gcatcagtga tgggactgag tactggattg    900
tccggaattc atgggggtgaa ccatgggggcg agagaggctg gctgaggatc gtgaccagca    960
cctataagga tgggaagggc gccagataca accttgccat cgaggagcac tgtacatttg   1020
gggaccccat cgtttaaggc catgtcacta gaagcgcagt ttaagaaaag gcatggtgac   1080
ccatgaccag aggggatcct atggttatgt gtgccaggct ggctggcagg aactggggtg   1140
gctatcaata ttggatggcg aggacagcgt ggtactggct gcgagtgttc ctgagagttg   1200
aaagtgggat gacttatgac acttgcacag catggctctg cctcacaatg atgcagtcag   1260
ccacctggtg aagaagtgac ctgcaacaca ggaaacgatg ggacctcagt cttcttcagc   1320
agaggacttg atattttgta tttggcaact gtgggcaata atatggcatt taagaggtga   1380
aagagttcag acttatcacc attcttatgt cactttagaa tcaagggtgg gggagggagg   1440
gagggagttg gcagtttcaa atcgcccaag tgatgaataa agtatctggc tctgcacgag   1500
a                                                                  1501

<210> SEQ ID NO 2
<211> LENGTH: 303
<212> TYPE: PRT
<213> ORGANISM: Homo sapiens

<400> SEQUENCE: 2

Met Ala Arg Arg Gly Pro Gly Trp Arg Pro Leu Leu Leu Val Leu
  1               5                  10                  15

Leu Ala Gly Ala Ala Gln Gly Gly Leu Tyr Phe Arg Arg Gly Gln Thr
                 20                  25                  30

Cys Tyr Arg Pro Leu Arg Gly Asp Gly Leu Ala Pro Leu Gly Arg Ser
             35                  40                  45

Thr Tyr Pro Arg Pro His Glu Tyr Leu Ser Pro Ala Asp Leu Pro Lys
         50                  55                  60

Ser Trp Asp Trp Arg Asn Val Asp Gly Val Asn Tyr Ala Ser Ile Thr
 65                  70                  75                  80

Arg Asn Gln His Ile Pro Gln Tyr Cys Gly Ser Cys Trp Ala His Ala
                 85                  90                  95

Ser Thr Ser Ala Met Ala Asp Arg Ile Asn Ile Lys Arg Lys Gly Ala
            100                 105                 110

Trp Pro Ser Thr Leu Leu Ser Val Gln Asn Val Ile Asp Cys Gly Asn
        115                 120                 125

Ala Gly Ser Cys Glu Gly Gly Asn Asp Leu Ser Val Trp Asp Tyr Ala
    130                 135                 140

His Gln His Gly Ile Pro Asp Glu Thr Cys Asn Asn Tyr Gln Ala Lys
145                 150                 155                 160

Asp Gln Glu Cys Asp Lys Phe Asn Gln Cys Gly Thr Cys Asn Glu Phe
                165                 170                 175

Lys Glu Cys His Ala Ile Arg Asn Tyr Thr Leu Trp Arg Val Gly Asp
            180                 185                 190
```

```
Tyr Gly Ser Leu Ser Gly Arg Glu Lys Met Met Ala Glu Ile Tyr Ala
            195                 200                 205
Asn Gly Pro Ile Ser Cys Gly Ile Met Ala Thr Glu Arg Leu Ala Asn
        210                 215                 220
Tyr Thr Gly Gly Ile Tyr Ala Glu Tyr Gln Asp Thr Thr Tyr Ile Asn
225                 230                 235                 240
His Val Val Ser Val Ala Gly Trp Gly Ile Ser Asp Gly Thr Glu Tyr
                245                 250                 255
Trp Ile Val Arg Asn Ser Trp Gly Pro Trp Gly Glu Arg Gly Trp
            260                 265                 270
Leu Arg Ile Val Thr Ser Thr Tyr Lys Asp Gly Lys Gly Ala Arg Tyr
            275                 280                 285
Asn Leu Ala Ile Glu Glu His Cys Thr Phe Gly Asp Pro Ile Val
            290                 295                 300
```

```
<210> SEQ ID NO 3
<211> LENGTH: 912
<212> TYPE: DNA
<213> ORGANISM: Homo sapiens

<400> SEQUENCE: 3
atggcgaggc gcgggccagg gtggcggccg cttctgctgc tcgtgctgct ggcgggcgcg    60
gcgcagggcg gcctctactt ccgccgggga cagacctgct accggcctct gcgggggggac   120
gggctggctc cgctggggcg cagcacatac ccccggcctc atgagtacct gtccccagcg   180
gatctgccca gagctgggga ctggcgcaat gtggatggtg tcaactatgc cagcatcacc   240
cggaaccagc acatccccca atactgcggc tcctgctggg cccacgccag caccagcgct   300
atggcggatc ggatcaacat caagaggaag ggagcgtggc cctccaccct cctgtccgtg   360
cagaacgtca tcgactgcgg taacgctggc tcctgtgaag ggggtaatga cctgtccgtg   420
tgggactacg cccaccagca cggcatccct gacgagacct gcaacaacta ccaggccaag   480
gaccaggagt gtgacaagtt taaccaatgt gggacatgca atgaattcaa agagtgccac   540
gccatccgga actacaccct ctggagggtg ggagactacg gctccctctc tggggaggag   600
aagatgatgg cagaaatcta cgcaaatggt cccatcagct gtggaataat ggcaacagaa   660
agactggcta actacaccgg aggcatctat gccgaatacc aggacaccac atatataaac   720
catgtcgttt ccgtggctgg gtggggcatc agtgatggga ctgagtactg gattgtccgg   780
aattcatggg gtgaaccatg gggcgagaga ggctggctga ggatcgtgac cagcacctat   840
aaggatggga agggcgccag atacaacctt gccatcgagg agcactgtac atttggggac   900
cccatcgttt aa                                                         912
```

```
<210> SEQ ID NO 4
<211> LENGTH: 2116
<212> TYPE: DNA
<213> ORGANISM: Homo sapiens

<400> SEQUENCE: 4
cggttctcca agcacccagc atcctgctag acgcgccgcg caccgacgga ggggacatgg    60
gcagagcaat ggtggccagg ctgggctgg ggctgctgct gctggcactg ctcctaccca   120
cgcagattta ttccagtgaa acaacaactg gaacttcaag taactcctcc cagagtactt   180
ccaactctgg gttggcccca aatccaacta atgccaccac caaggcggct ggtggtgccc   240
tgcagtcaac agccagtctc ttcgtggtct cactctctct tctgcatctc tactcttaag   300
```

```
agactcaggc caagaaacgt cttctaaatt tccccatctt ctaaacccaa tccaaatggc      360
gtctggaagt ccaatgtggc aaggaaaaac aggtcttcat cgaatctact aattccacac      420
cttttattga cacagaaaat gttgagaatc ccaaatttga ttgatttgaa gaacatgtga      480
gaggtttgac tagatgatga atgccaatat aaatctgctg gagtttcat gtacaagatg       540 aaggagaggc aacatccaaa atagttaaga catgatttcc ttgaatgtgg cttgagaaat      600
atggacactt aatactacct tgaaaataag aatagaaata aggatggga ttgtggaatg       660 gagattcagt tttcattggt tcattaattc tataaggcca taaacaggt aatataaaaa       720 gcttccatcg atctatttat atgtacatga aaggaatcc ccaggtgtta ctgtaattcc       780
tcaacgtatt gtttcgacgg cactaattta atgccgatat actctagatg aatgtttaca      840
ttgttgagct attgctgttc tcttgggaac tgaactcact ttcctcctga ggctttggat      900
ttgacattgc atttgacctt ttaggtagta attgacatgt gccagggcaa tgatgaatga      960
gaatctaccc cagatccaag catcctgagc aactcttgat tatccatatt gagtcaaatg     1020
gtaggcattt cctatcacct gtttccattc aacaagagca ctacattctt ttagctaaac     1080
ggattccaaa gagtagaatt gcattgacca cgactaattt caaaatgctt tttattatta     1140
ttatttttta gacagtctca ctttgtcgcc caggccggag tgcagtggtg cgatctcaga     1200
tcagtgtacc atttgcctcc cgggctcaag cgattctcct gcctcagcct cccaagtagc     1260
tgggattaca ggcacctgcc accatgcccg gctaattttt gtaattttag tagagacagg     1320
gtttcaccat gttgcccagg ctggtttaga actcctgacc tcaggtgatc cacccgcctc     1380
ggcctcccaa agtgctggga ttacaggctt gagccccgc gcccagccat caaaatgctt      1440
tttatttctg catatgtttg aatacttttt acaatttaaa aaaatgatct gttttgaagg     1500
caaaattgca aatcttgaaa ttaagaaggc aaaatgtaaa ggagtcaaac tataaatcaa     1560
gtatttggga agtgaagact ggaagctaat ttgcataaat tcacaaactt ttatactctt     1620
tctgtatata cattttttt ctttaaaaaa caactatgga tcagaatagc aacatttaga      1680 acacttttg ttatcagtca atatttttag atagttagaa cctggtccta agcctaaaag      1740
tgggcttgat tctgcagtaa atcttttaca actgcctcga cacacataaa ccttttaaa      1800 aatagacact ccccgaagtc ttttgtttgt atggtcacac actgatgctt agatgttcca     1860
gtaatctaat atggccacag tagtcttgat gaccaaagtc cttttttcc atctttagaa      1920 aactacatgg gaacaaacag atcgaacagt tttgaagcta ctgtgtgtgt gaatgaacac     1980
tcttgcttta ttccagaatg ctgtacatct attttggatt gtatattgtg gttgtgtatt     2040
tacgctttga ttcatagtaa cttccttatgg aattgatttg cattgaacga caaactgtaa     2100
ataaaaagaa acggtg                                                     2116
```

<210> SEQ ID NO 5
<211> LENGTH: 80
<212> TYPE: PRT
<213> ORGANISM: Homo sapiens

<400> SEQUENCE: 5

Met Gly Arg Ala Met Val Ala Arg Leu Gly Leu Gly Leu Leu Leu Leu
 1               5                  10                  15

Ala Leu Leu Leu Pro Thr Gln Ile Tyr Ser Ser Glu Thr Thr Thr Gly
             20                  25                  30

Thr Ser Ser Asn Ser Ser Gln Ser Thr Ser Asn Ser Gly Leu Ala Pro
         35                  40                  45

```
Asn Pro Thr Asn Ala Thr Thr Lys Ala Ala Gly Gly Ala Leu Gln Ser
    50                  55                  60

Thr Ala Ser Leu Phe Val Val Ser Leu Ser Leu Leu His Leu Tyr Ser
65                  70                  75                  80

<210> SEQ ID NO 6
<211> LENGTH: 243
<212> TYPE: DNA
<213> ORGANISM: Homo sapiens

<400> SEQUENCE: 6
atgggcagag caatggtggc caggctgggg ctggggctgc tgctgctggc actgctccta      60
cccacgcaga tttattccag tgaaacaaca actggaactt caagtaactc ctcccagagt     120
acttccaact ctgggttggc cccaaatcca actaatgcca ccaccaaggc ggctggtggt     180
gccctgcagt caacagccag tctcttcgtg gtctcactct ctcttctgca tctctactct     240
taa                                                                    243

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcgcgggcca gggtggcggc cgcttctgc                                         29

<210> SEQ ID NO 8
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gcgcgggcca ggguggcggc cgcuucugc                                         29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggccagggtg gcggccgctt ctgctgctc                                         29

<210> SEQ ID NO 10
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ggccaggrug gcggccgcuu cugcugcuc                                         29

<210> SEQ ID NO 11
```

<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtggcggccg cttctgctgc tcgtgctgc                                    29

<210> SEQ ID NO 12
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
guggcggccg cuucugcugc ucgugcugc                                    29

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gatgggaagg gcgccagata caaccttgc                                    29

<210> SEQ ID NO 14
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gaugggaagg gcgccagaua caaccuugc                                    29

<210> SEQ ID NO 15
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 aaaaaa                                                              6

<210> SEQ ID NO 16
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 gaagcttg                                                            8

<210> SEQ ID NO 17
<211> LENGTH: 21

```
<212> TYPE: DNA
<213> ORGANISM: Artificial Sequence
<220> FEATURE:
<223> OTHER INFORMATION: Description of Artificial Sequence: Primer

<400> SEQUENCE: 17
ggtgtttcgt cctttccaca a                                              21

<210> SEQ ID NO 18
<211> LENGTH: 93
<212> TYPE: DNA
<213> ORGANISM: Artificial Sequence
<220> FEATURE:
<223> OTHER INFORMATION: Description of Artificial Sequence: Primer

<400> SEQUENCE: 18
aaaaaagcag aagcggccgc caccctggcc cgcgccaagc ttcgcgcggg ccagggtggc     60
ggccgcttct gcggtgtttc gtcctttcca caa                                 93

<210> SEQ ID NO 19
<211> LENGTH: 93
<212> TYPE: DNA
<213> ORGANISM: Artificial Sequence
<220> FEATURE:
<223> OTHER INFORMATION: Description of Artificial Sequence: Primer

<400> SEQUENCE: 19
aaaaaagcag cacgagcagc agaagcggcc gccaccaagc ttcgtggcgg ccgcttctgc     60
tgctcgtgct gcggtgtttc gtcctttcca caa                                 93

<210> SEQ ID NO 20
<211> LENGTH: 93
<212> TYPE: DNA
<213> ORGANISM: Artificial Sequence
<220> FEATURE:
<223> OTHER INFORMATION: Description of Artificial Sequence: Primer

<400> SEQUENCE: 20
aaaaaagcaa ggttgtatct ggcgccctta ccatccaagc ttcgatggga agggcgccag     60
atacaacctt gcggtgtttc gtcctttcca caa                                 93

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggtggccagg ctggggctgg ggctgctgc                                      29

<210> SEQ ID NO 22
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gguggccagg cuggggcugg ggcugcugc                                      29

<210> SEQ ID NO 23
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggccaggctg gggctggggc tgctgctgc                                  29

<210> SEQ ID NO 24
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ggccaggcug gggcuggggc ugcugcugc                                  29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gctggggctg gggctgctgc tgctggcac                                  29

<210> SEQ ID NO 26
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gcuggggcug gggcugcugc ugcuggcac                                  29

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtctcactct ctcttctgca tctctactc                                  29

<210> SEQ ID NO 28
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gucucacucu cucuucugca ucucuacuc                                  29

<210> SEQ ID NO 29
<211> LENGTH: 93
```

```
-continued

<212> TYPE: DNA
<213> ORGANISM: Artificial Sequence
<220> FEATURE:
<223> OTHER INFORMATION: Description of Artificial Sequence: Primer

<400> SEQUENCE: 29
aaaaaagcag cagccccagc cccagcctgg ccacccaagc ttcggtggcc aggctggggc      60
tggggctgct gcggtgtttc gtcctttcca caa                                  93

<210> SEQ ID NO 30
<211> LENGTH: 93
<212> TYPE: DNA
<213> ORGANISM: Artificial Sequence
<220> FEATURE:
<223> OTHER INFORMATION: Description of Artificial Sequence: Primer

<400> SEQUENCE: 30
aaaaaagcag cagcagcccc agccccagcc tggcccaagc ttcggccagg ctggggctgg      60
ggctgctgct gcggtgtttc gtcctttcca caa                                  93

<210> SEQ ID NO 31
<211> LENGTH: 93
<212> TYPE: DNA
<213> ORGANISM: Artificial Sequence
<220> FEATURE:
<223> OTHER INFORMATION: Description of Artificial Sequence: Primer

<400> SEQUENCE: 31
aaaaaagtgc cagcagcagc agccccagcc ccagccaagc ttcgctgggg ctggggctgc      60
tgctgctggc acggtgtttc gtcctttcca caa                                  93

<210> SEQ ID NO 32
<211> LENGTH: 93
<212> TYPE: DNA
<213> ORGANISM: Artificial Sequence
<220> FEATURE:
<223> OTHER INFORMATION: Description of Artificial Sequence: Primer

<400> SEQUENCE: 32
aaaaaagagt agagatgcag aagagagagt gagaccaagc ttcgtctcac tctctcttct      60
gcatctctac tcggtgtttc gtcctttcca caa                                  93
```